United States Patent
Debenham et al.

(10) Patent No.: US 10,864,211 B2
(45) Date of Patent: Dec. 15, 2020

(54) HYDROXY ISOXAZOLE COMPOUNDS USEFUL AS GPR120 AGONISTS

(71) Applicant: Merck Sharp & Dohme Corp., Rahway, NJ (US)

(72) Inventors: John S. Debenham, Scotch Plains, NJ (US); Jason M. Cox, Whitehouse Station, NJ (US); Ping Lan, Plainsboro, NJ (US); Zhongxiang Sun, Princeton, NJ (US); Zhe Feng, Hillsborough, NJ (US); Chunrui Sun, Westfield, NJ (US); W. Michael Seganish, Castro Valley, CA (US); Zhong Lai, East Brunswick, NJ (US); Cheng Zhu, Edison, NJ (US); Thomas Bara, Scotch Plains, NJ (US); Murali Rajagopalan, Edison, NJ (US); Qun Dang, Westfield, NJ (US); Hyunjin M. Kim, Livingston, NJ (US); Bin Hu, Shanghai (CN); Jinglai Hao, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/462,344

(22) PCT Filed: Dec. 11, 2017

(86) PCT No.: PCT/US2017/065499
§ 371 (c)(1),
(2) Date: May 20, 2019

(87) PCT Pub. No.: WO2018/111734
PCT Pub. Date: Jun. 21, 2018

(65) Prior Publication Data
US 2019/0269679 A1 Sep. 5, 2019

(30) Foreign Application Priority Data
Dec. 15, 2016 (CN) ............... PCT/CN2016/110054

(51) Int. Cl.
*A61K 31/497* (2006.01)
*A61K 31/4439* (2006.01)
*A61K 31/42* (2006.01)
*A61K 31/444* (2006.01)
*C07D 417/14* (2006.01)
*C07D 413/04* (2006.01)
*C07D 413/14* (2006.01)
*C07D 231/20* (2006.01)
*A61P 43/00* (2006.01)
*A61P 3/10* (2006.01)
*A61K 9/48* (2006.01)
*A61K 9/00* (2006.01)
*C07D 261/12* (2006.01)

(52) U.S. Cl.
CPC .......... *A61K 31/497* (2013.01); *A61K 9/0053* (2013.01); *A61K 9/4858* (2013.01); *A61K 31/42* (2013.01); *A61K 31/444* (2013.01); *A61K 31/4439* (2013.01); *A61P 3/10* (2018.01); *A61P 43/00* (2018.01); *C07D 231/20* (2013.01); *C07D 261/12* (2013.01); *C07D 413/04* (2013.01); *C07D 413/14* (2013.01); *C07D 417/14* (2013.01)

(58) Field of Classification Search
None
See application file for complete search history.

(56) References Cited

U.S. PATENT DOCUMENTS

| 8,367,708 B2 | 5/2013 | Hashimoto et al. |
| 2010/0130559 A1 | 5/2010 | Hashimoto et al. |
| 2011/0065739 A1 | 3/2011 | Ishikawa et al. |

FOREIGN PATENT DOCUMENTS

| EP | 2298750 A1 | 3/2011 |
| EP | 2495238 A1 | 9/2012 |

(Continued)

OTHER PUBLICATIONS

Cintra, Dennys, E. et al., Unsaturated Fatty Acids Revert Diet-Induced Hypothalamic Inflammation in Obesity, PLoS ONE, 2012, p. 1-15, vol. 7, Issue 1.

(Continued)

*Primary Examiner* — Kamal A Saeed
(74) *Attorney, Agent, or Firm* — Baerbel R. Brown; Catherine D. Fitch

(57) ABSTRACT

The present invention relates to a compound represented by formula (I): and pharmaceutically acceptable salts thereof are disclosed as useful for treating or preventing diabetes, hyperlipidemia, obesity, NASH, inflammation related disorders, and related diseases and conditions. The compounds are useful as agonists of the G-protein coupled receptor GPR120. Pharmaceutical compositions and methods of treatment are also included.

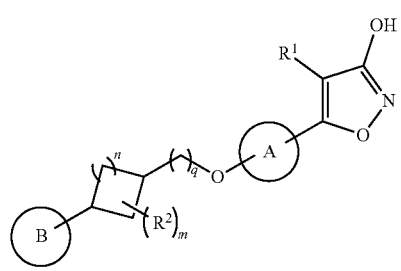

14 Claims, No Drawings

(56) References Cited

FOREIGN PATENT DOCUMENTS

| EP | 2098517 B1 | 12/2013 |
|---|---|---|
| JP | 2004262890 A | 9/2004 |
| WO | WO2004018428 A1 | 3/2004 |
| WO | 2008066131 A1 | 6/2008 |
| WO | 2009147990 A1 | 12/2009 |
| WO | 2014165827 A1 | 10/2014 |
| WO | WO2015125085 A1 | 8/2015 |
| WO | 2016012965 A2 | 1/2016 |

OTHER PUBLICATIONS

Hirasawa, Akira, et al., Free fatty acids regulate gut incretin glucagon-like peptide-1 secretion through GPR120, Nature Medicine, 2005, p. 90-94, vol. 11, No. 1.

Ichimura, Atsuhiko, et al., Dysfunction of lipid sensor GPR120 leads to obesity in both mouse and human, Nature, 2012, p. 350-357, vol. 483.

Oh, Da Young, et al., GPR120 is an Omega-3 Fatty Acid Receptor Mediating Potent Anti-Inflammatory and Insulin Sensitizing Effects, Cell, 2010, p. 687-698, vol. 142, No. 5.

Talukdar, Saswata, et al., Targeting GPR120 an dother fatty acid-sensing GPCRs ameliorates insulin resistance and inflammatory diseases, Trends in Pharmacological Sciences, 2011, p. 543-550, vol. 32, No. 9.

HYDROXY ISOXAZOLE COMPOUNDS USEFUL AS GPR120 AGONISTS

CROSS-REFERENCE TO RELATED APPLICATIONS

This application is a U.S. National Phase application under 35 U.S.C. § 371 of PCT Application No. PCT/US2017/065499, filed on Dec. 11, 2017, which claims priority from and the benefit of Chinese PCT Application Number PCT/CN2016/110054, filed Dec. 15, 2016.

BACKGROUND OF THE INVENTION

The present invention relates to substituted chromane derivatives that are useful in the pharmaceutical field. The compounds act as GPR120 receptor function regulating agents (modulators), which may be useful as drugs for treating and/or preventing diabetes, obesity, hyperlipidemia, and inflammation related disorders.

GPR120, a G protein-coupled receptor, causes intracellular signaling through binding with unsaturated long chain fatty acids, such as alpha-linoleic acid, to induce various biological reactions. Actions of GPR120 and its ligand(s) have been reported to promote secretion of glucagon-like-peptide-1 ("GLP-1") functions to reduce blood glucose level in gastrointestinal cell lines (see Nature Medicine, 2005, 11(1), 90-94). GLP-1, which is a peptide hormone, has been found to induce insulin secretion depending on a blood glucose level. GLP-1 is also suggested to be efficacious for delaying the apoptosis of beta cells in type II diabetes mellitus.

GPR120 is expressed in adipocytes. GPR120 has been found to be increasingly expressed by adipose differentiation induction. In addition, actions of GPR120 and its ligand have been reported to suppress lipolysis in adipose-differentiated cells. A high blood lipid level is known to be one of the causes of insulin resistance. Suppression of lipolysis by a GPR120 agonist is thus expected to decrease the levels of free fatty acids in blood to normalize blood lipid levels, and may result in improvement in insulin resistance.

GPR120 is also expressed in the pituitary gland, and a GPR120 ligand is reported to suppress adrenocorticotropic hormone secretion. Adrenocorticotropic hormone promotes glucocorticoid secretion downstream thereof to induce action such as promotion of gluconeogenesis in the liver, inhibitory action against glucose uptake in muscle and peripheral tissue, lipolysis in adipose tissue or release of fatty acids or glycerol. Accordingly, GPR120 is considered to exhibit hypoglycemic action or blood lipid lowering action via suppression action against adrenocorticotropic hormone secretion even in the center.

Recently, GPR120 has been shown to play a role in obesity in both mice and humans. GPR120 knockout mice fed a high fat diet developed obesity, glucose intolerance and fatty liver with decreased adipocyte differentiation and lipogenesis and enhanced hepatic lipogenesis. In the study, insulin resistance in such mice was associated with reduced insulin signaling and enhanced inflammation in adipose tissue. In humans, GPR120 expression in adipose tissue is significantly higher in obese individuals than in lean controls (See Ichimura, et al., Nature, 2012, 483, 350-54; and Cintra, et al., Plos One, 2012, 7(1), 1-15).

GPR120 has also been shown to play a role in inflammation. Wild-type mice treated with omega-3 fatty acids inhibited macrophage-induced tissue inflammation and enhanced systemic insulin sensitivity. However, this effect was not observed in GPR120 knockout mice (See Oh, et al., Cell, 2010, 142, 687; and Talukar, et al., Trends in Pharmacological Sciences, 2011, 32(9), 543-550).

In light of the above description, a compound having GPR120 agonist activity is considered to be useful as an agent for treating and/or preventing diabetes mellitus, obesity, hyperlipidemia, fatty liver (including non-alcoholic steatohepatitis or NASH), and inflammation related disorders.

Compounds having GPR120 activity are disclosed in WO 2008/066131 and WO 2009/147990, and U.S. Pat. No. 8,367,708. Cyclic ether compounds are disclosed in WO 2014/165827.

SUMMARY OF THE INVENTION

The present invention relates to compounds represented by formula I:

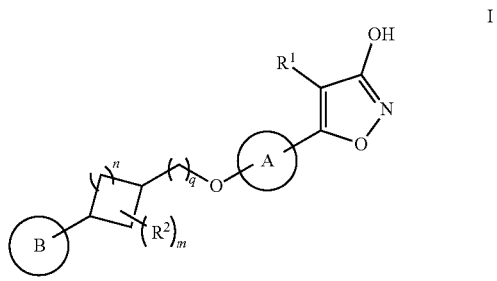

as well as pharmaceutically acceptable salts thereof, and pharmaceutical compositions comprising a compound of formula I.

The present invention further relates to methods of treating diabetes, obesity, hyperlipidemia, NASH, inflammation related disorders, and related diseases and conditions, comprising administering a compound of formula I to a patient in need thereof.

DETAILED DESCRIPTION OF THE INVENTION

The present invention relates to compounds represented by formula I:

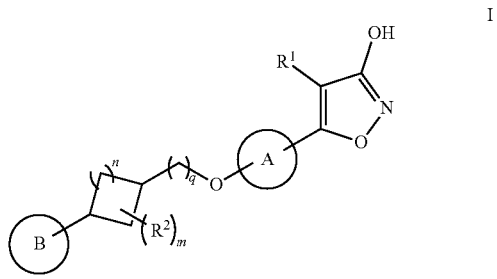

or a pharmaceutically acceptable salt thereof, wherein:
A is selected from:
 (1) aryl and
 (2) heteroaryl,
wherein each aryl and heteroaryl is unsubstituted or substituted with 1, 2, 3 or 4 substituents selected from $R^a$;

B is selected from:
  (1) aryl,
  (2) —O-aryl,
  (3) —$(CH_2)_p$—O-aryl,
  (4) —O—$(CH_2)_p$-aryl,
  (5) heteroaryl,
  (6) —O-heteroaryl,
  (7) —$(CH_2)_p$—O-heteroaryl,
  (8) —O—$(CH_2)_p$-heteroaryl,
  (9) —$C_{3-10}$cycloalkyl,
  (10) —$(CH_2)_p$—O—$C_{3-10}$cycloalkyl,
  (11) —O—$(CH_2)_p$—$C_{3-10}$cycloalkyl,
  (12) —$C_{2-10}$cycloheteroalkyl,
  (13) —$(CH_2)_p$—O—$C_{2-10}$cycloheteroalkyl, and
  (14) —O—$(CH_2)_p$—$C_{3-10}$cycloheteroalkyl,
wherein each —$CH_2$, cycloalkyl, cycloheteroalkyl, aryl, and heteroaryl is unsubstituted or substituted with 1, 2 or 3 or 4 substituents selected from $R^b$;
$R^1$ is selected from:
  (1) hydrogen, and
  (2) halogen;
$R^2$ is selected from:
  (1) halogen,
  (2) —$C_{1-6}$alkyl,
  (3) —$C_{2-6}$alkenyl,
  (4) —$C_{2-6}$alkynyl, and
  (5) —CN,
wherein each alkyl, alkenyl and alkynyl is unsubstituted or substituted with 1-3 substituents selected from: halogen, OH, —$NH_2$, —$NH(C_{1-6}alkyl)$, —$N(C_{1-6}alkyl)_2$ and —$OC_{1-6}alkyl$;
each $R^a$ is independently selected from:
  (1) halogen, and
  (2) —$C_{1-6}$alkyl,
wherein each alkyl is unsubstituted or substituted with 1-3 substituents selected from: —$C_{1-6}$alkyl and halogen;
each $R^b$ is independently selected from:
  (1) halogen,
  (2) —CN,
  (3) —OH,
  (4) —$C_{1-6}$alkyl,
  (5) —$C_{2-6}$alkenyl,
  (6) —$C_{2-6}$alkynyl,
  (7) —O—$C_{1-6}$alkyl,
  (8) —O—$C_{2-6}$alkenyl,
  (9) —O—$C_{2-6}$alkynyl,
  (10) —$C_{3-10}$cycloalkyl,
  (11) —$C_{3-10}$cycloalkenyl,
  (12) aryl,
  (13) heteroaryl,
  (14) —$OC_{3-10}$cycloalkyl,
  (15) —$OC_{3-6}$cycloheteroalkyl,
  (16) —O-aryl,
  (17) —O-heteroaryl,
  (18) —$NH_2$,
  (19) —$NHC_{1-6}$alkyl,
  (20) —$N(C_{1-6}alkyl)_2$,
  (21) —$SC_{1-6}$alkyl,
  (22) —$SOC_{1-6}$alkyl, and
  (23) —$SO_2C_{1-6}$alkyl,
wherein each alkyl, alkenyl, alkynyl, cycloalkyl, cycloalkenyl, cycloheteroalkyl, aryl and heteroaryl is unsubstituted or substituted with 1-3 substituents selected from: —$C_{1-6}$alkyl, —$OC_{1-6}$alkyl, —$CF_3$, —$OCF_3$, and halogen;
n is 1 or 2;
m is 0, 1, or 2;
p is 1, 2, or 3; and
q is 0 or 1.

In one embodiment of the present invention, A is selected from: aryl and heteroaryl, wherein A is unsubstituted or substituted with 1, 2, 3 or 4 substituents selected from $R^a$. In a class of this embodiment, A is selected from: phenyl, pyridine, pyrimidine, and pyrazine wherein A is unsubstituted or substituted with 1, 2, 3 or 4 substituents selected from $R^a$.

In another embodiment of the present invention, A is aryl, wherein aryl is unsubstituted or substituted with 1, 2, 3 or 4 substituents selected from $R^a$. In a class of this embodiment, A is phenyl, wherein phenyl is unsubstituted or substituted with 1, 2, 3 or 4 substituents selected from $R^a$.

In another embodiment of the present invention, A is heteroaryl, wherein heteroaryl is unsubstituted or substituted with 1, 2, 3 or 4 substituents selected from $R^a$. In a class of this embodiment, A is selected from: pyridine, pyrimidine, and pyrazine, wherein heteroaryl is unsubstituted or substituted with 1, 2, 3 or 4 substituents selected from $R^a$.

In another embodiment of the present invention, B is selected from: aryl, —O-aryl, —$(CH_2)_p$—O-aryl, —O—$(CH_2)_p$-aryl, heteroaryl, —O-heteroaryl, —O—$(CH_2)_p$-heteroaryl, —$C_{3-10}$cycloalkyl, and —O—$(CH_2)_p$—$C_{3-10}$cycloalkyl, wherein B is unsubstituted or substituted with 1, 2 or 3 or 4 substituents selected from $R^b$. In a class of this embodiment, B is selected from: phenyl, naphthalene, —O-phenyl, —$CH_2$—O-phenyl, —O—$CH_2$-phenyl, pyridine, thiazole, benzothiazole, —O-thiene, —O—$(CH_2)_p$-thiazole, benzodioxole, benzodioxine, cyclohexane, —O—$CH_2$-cyclohexane, and —O—$CH_2$-cyclopentane, wherein B is unsubstituted or substituted with 1, 2 or 3 or 4 substituents selected from $R^b$. In another class of this embodiment, B is selected from: phenyl, —O-phenyl, —$CH_2$—O-phenyl, —O—$CH_2$-phenyl, pyridine, thiazole, benzothiazole, —O-thiene, —O—$(CH_2)_p$-thiazole, cyclohexane, —O—$CH_2$-cyclohexane, and —O—$CH_2$-cyclopentane, wherein B is unsubstituted or substituted with 1, 2 or 3 or 4 substituents selected from $R^b$.

In another embodiment of the present invention, B is selected from: aryl, —O-aryl, —O—$(CH_2)_p$-aryl, and heteroaryl, wherein B is unsubstituted or substituted with 1, 2 or 3 substituents selected from $R^b$. In a class of this embodiment, B is selected from: phenyl, —O-phenyl, —O—$CH_2$-phenyl, pyridine, thiazole, and —O—$CH_2$-cyclohexane, wherein B is unsubstituted or substituted with 1, 2 or 3 substituents selected from $R^b$.

In another embodiment of the present invention, $R^1$ is hydrogen.

In another embodiment of the present invention, $R^1$ is halogen. In a class of this embodiment, $R^1$ is F.

In another embodiment of the present invention, $R^2$ is selected from: halogen, and —$C_{1-6}$alkyl, wherein each alkyl is unsubstituted or substituted with 1-3 substituents selected from: halogen, OH, —$NH_2$, —$NH(C_{1-6}alkyl)$, —$N(C_{1-6}alkyl)_2$ and —$OC_{1-6}alkyl$.

In a class of this embodiment, $R^2$ is selected from: F, Cl and $CH_3$, wherein each $CH_3$ is unsubstituted or substituted with 1-3 substituents selected from: halogen, OH, —$NH_2$, —$NH(C_{1-6}alkyl)$, —$N(C_{1-6}alkyl)_2$ and —$OC_{1-6}alkyl$.

In another class of this embodiment, $R^2$ is selected from: F, and $CH_3$, wherein each $CH_3$ is unsubstituted or substituted with 1-3 substituents selected from: halogen, OH, —$NH_2$, —$NH(C_{1-6}alkyl)$, —$N(C_{1-6}alkyl)_2$ and —$OC_{1-6}alkyl$.

In another embodiment of the present invention, $R^2$ is halogen. In a class of this embodiment, $R^2$ is selected from: F and Cl. In another class of this embodiment, $R^2$ is F.

In another embodiment of the present invention, each $R^a$ is independently selected from: halogen, and —$C_{1-6}$alkyl, wherein each alkyl is unsubstituted or substituted with 1-3 substituents selected from: —$C_{1-6}$alkyl and halogen. In a class of this embodiment, each $R^a$ is independently selected from: F, and $CH_3$, wherein each $CH_3$ is unsubstituted or substituted with 1-3 substituents selected from: —$C_{1-6}$alkyl and halogen.

In another embodiment of the present invention, each $R^a$ is halogen. In a class of this embodiment, each $R^a$ is F.

In another embodiment of the present invention, each $R^a$ is —$C_{1-6}$alkyl, wherein each alkyl is unsubstituted or substituted with 1-3 substituents selected from: —$C_{1-6}$alkyl and halogen. In a class of this embodiment, each $R^a$ is $CH_3$, wherein each $CH_3$ is unsubstituted or substituted with 1-3 substituents selected from: —$C_{1-6}$alkyl and halogen.

In another embodiment of the present invention, each $R^b$ is independently selected from: halogen, —CN, —$C_{1-6}$alkyl, —O—$C_{1-6}$alkyl, —$C_{3-6}$cycloalkyl, heteroaryl, and —$OC_{3-10}$cycloalkyl, wherein each alkyl, cycloalkyl, and heteroaryl is unsubstituted or substituted with 1-3 substituents selected from: —$C_{1-6}$alkyl, —$OC_{1-6}$alkyl, —$CF_3$, —$OCF_3$, and halogen. In a class of this embodiment, each $R^b$ is independently selected from: F, Br, Cl, —CN, —$CH_3$, —$CH_2CH_3$, —$CH_2F$, —$CHF_2$, —$CF_3$, —$OCH_3$, —$OCH_2CH_3$, —$OCH(CH_3)_2$, —O—$CHF_2$, —$OCF_3$, cyclopropyl, cyclobutyl, pyridine, oxazole, —O-cyclopropyl, and —O-cyclobutyl, wherein each alkyl, cycloalkyl, and heteroaryl is unsubstituted or substituted with 1-3 substituents selected from: —$C_{1-6}$alkyl, —$OC_{1-6}$alkyl, —$CF_3$, —$OCF_3$, and halogen. In another class of this embodiment, each $R^b$ is independently selected from: F, Br, Cl, —CN, —$CH_3$, —$CH_2CH_3$, —$CH_2F$, —$CHF_2$, —$CF_3$, —$OCH_3$, —$OCH_2CH_3$, —$OCH(CH_3)_2$, —O—$CHF_2$, —$OCF_3$, cyclopropyl, cyclobutyl, pyridine, oxazole, —O-cyclopropyl, and —O-cyclobutyl, wherein each cycloalkyl, and heteroaryl is unsubstituted or substituted with 1-3 substituents selected from: —$C_{1-6}$alkyl, —$OC_{1-6}$alkyl, —$CF_3$, —$OCF_3$, and halogen. In another class of this embodiment, each $R^b$ is independently selected from: F, Br, Cl, —CN, —$CH_3$, —$CH_2CH_3$, —$CH_2F$, —$CHF_2$, —$CF_3$, —$OCH_3$, —$OCH_2CH_3$, —$OCH(CH_3)_2$, —O—$CHF_2$, —$OCF_3$, cyclopropyl, cyclobutyl, pyridine, oxazole, —O-cyclopropyl, and —O-cyclobutyl.

In another embodiment of the present invention, each $R^b$ is independently selected from: F, Br, Cl, —$C_{1-6}$alkyl, —O—$C_{1-6}$alkyl, and —$OC_{3-10}$cycloalkyl, wherein each alkyl, cycloalkyl, and heteroaryl is unsubstituted or substituted with 1-3 substituents selected from: —$C_{1-6}$alkyl, —$OC_{1-6}$alkyl, —$CF_3$, —$OCF_3$, and halogen. In a class of this embodiment, each $R^b$ is independently selected from: F, Br, Cl, —$CH_3$, —$CH_2CH_3$, —$CH_2F$, —$CHF_2$, —$CF_3$, —$OCH_3$, —$OCH_2CH_3$, —$OCH(CH_3)_2$, —O—$CHF_2$, —$OCF_3$, —O-cyclopropyl, and —O-cyclobutyl, wherein each alkyl, cycloalkyl, and heteroaryl is unsubstituted or substituted with 1-3 substituents selected from: —$C_{1-6}$alkyl, —$OC_{1-6}$alkyl, —$CF_3$, —$OCF_3$, and halogen. In another class of this embodiment, each $R^b$ is independently selected from: F, Cl, —$CHF_2$, —$CF_3$, —O—$CHF_2$, —$OCF_3$, —O-cyclopropyl, and —O-cyclobutyl, wherein each alkyl and cycloalkyl is unsubstituted or substituted with 1-3 substituents selected from: —$C_{1-6}$alkyl, —$OC_{1-6}$alkyl, —$CF_3$, —$OCF_3$, and halogen. In another class of this embodiment, each $R^b$ is independently selected from: F, Cl, —$CHF_2$, —$CF_3$, —O—$CHF_2$, —$OCF_3$, —O-cyclopropyl, and —O-cyclobutyl, wherein each cycloalkyl is unsubstituted or substituted with 1-3 substituents selected from: —$C_{1-6}$alkyl, —$OC_{1-6}$alkyl, —$CF_3$, —$OCF_3$, and halogen. In another class of this embodiment, each $R^b$ is independently selected from: F, Cl, —$CHF_2$, —$CF_3$, —O—$CHF_2$, —$OCF_3$, —O-cyclopropyl, and —O-cyclobutyl.

In another embodiment of the present invention, n is 1 or 2. In a class of this embodiment, n is 1. In another class of this embodiment, n is 2.

In another embodiment of this invention, m is 0, 1 or 2. In a class of this embodiment, m is 1 or 2. In another class of this embodiment, m is 0 or 1. In another class of this embodiment, m is 0 or 2. In another class of this embodiment, m is 0. In another class of this embodiment, m is 1. In another class of this embodiment, m is 2.

In another embodiment of this invention, p is 0, 1, 2 or 3. In a class of this embodiment, p is 1, 2 or 3. In another class of this embodiment, p is 0, 1 or 3. In another embodiment of this invention, p is 0, 1 or 2. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3.

In another embodiment of the present invention, q is 1 or 2. In a class of this embodiment, q is 1. In another class of this embodiment, q is 2.

Another embodiment of the present invention relates to compounds of structural formula I wherein:
A is selected from:
  (1) aryl, and
  (2) heteroaryl,
wherein each aryl and heteroaryl is unsubstituted or substituted with 1, 2, 3 or 4 substituents selected from $R^a$;
B is selected from:
  (1) aryl,
  (2) —O-aryl,
  (3) —$(CH_2)_p$—O-aryl,
  (4) —O—$(CH_2)_p$-aryl,
  (5) heteroaryl,
  (6) —O-heteroaryl,
  (7) —O—$(CH_2)_p$-heteroaryl,
  (8) —$C_{3-10}$cycloalkyl, and
  (9) —O—$(CH_2)_p$—$C_{3-10}$cycloalkyl,
wherein B is unsubstituted or substituted with 1, 2 or 3 or 4 substituents selected from $R^b$;
$R^1$ is selected from:
  (1) hydrogen, and
  (2) halogen;
$R^2$ is selected from:
  (1) halogen, and
  (2) —$C_{1-6}$alkyl,
wherein each alkyl is unsubstituted or substituted with 1-3 substituents selected from: halogen, OH, —$NH_2$, —NH($C_{1-6}$alkyl), —N($C_{1-6}$alkyl)$_2$ and —$OC_{1-6}$alkyl;
n is 1 or 2;
m is 0, 1, or 2;
p is 1, 2, or 3;
q is 0 or 1; and
wherein $R^a$, and $R^b$ are as described above;
or a pharmaceutically acceptable salt thereof.

Another embodiment of the present invention relates to compounds of structural formula I wherein:
A is selected from:
  (1) aryl, and
  (2) heteroaryl,
wherein each aryl and heteroaryl is unsubstituted or substituted with 1, 2, 3 or 4 substituents selected from $R^a$;

B is selected from:
  (1) aryl,
  (2) —O-aryl,
  (3) —O—(CH$_2$)$_p$-aryl, and
  (4) heteroaryl,
wherein B is unsubstituted or substituted with 1, 2 or 3 substituents selected from R$^b$;
R$^1$ is hydrogen;
R$^2$ is halogen;
n is 1;
m is 0, or 1;
p is 1, 2, or 3;
q is 0 or 1; and
wherein R$^a$, and R$^b$ are as described above;
or a pharmaceutically acceptable salt thereof.

In another embodiment of the present invention, the invention relates to compounds of structural formula Ia:

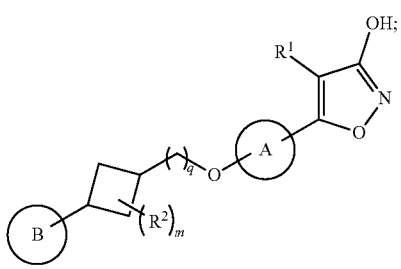

or a pharmaceutically acceptable salt thereof.

In another embodiment of the present invention, the invention relates to compounds of structural formula Ib:

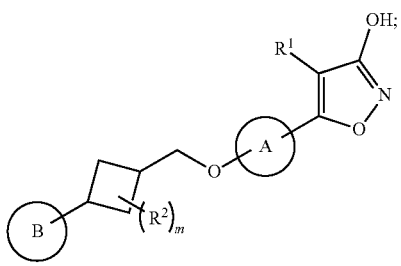

or a pharmaceutically acceptable salt thereof.

In another embodiment of the present invention, the invention relates to compounds of structural formula Ic:

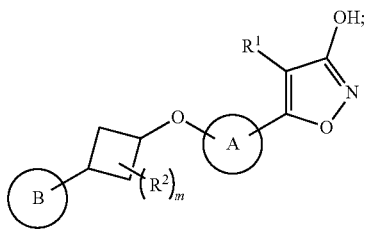

or a pharmaceutically acceptable salt thereof.

In another embodiment of the present invention, the invention relates to compounds of structural formula Id:

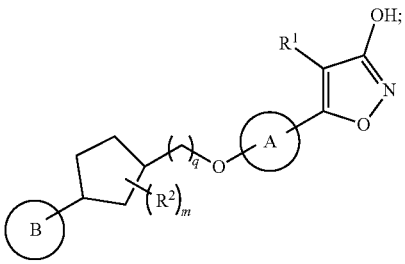

or a pharmaceutically acceptable salt thereof.

In another embodiment of the present invention, the invention relates to compounds of structural formula Ie:

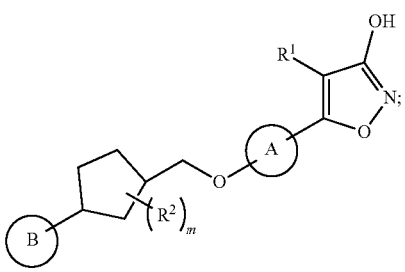

or a pharmaceutically acceptable salt thereof.

In another embodiment of the present invention, the invention relates to compounds of structural formula If:

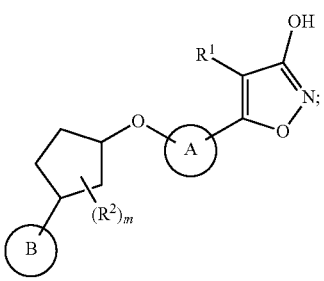

or a pharmaceutically acceptable salt thereof.

The compound of structural formula I, includes the compounds of structural formulas Ia, Ib, Ic, Id, Ie and If, and pharmaceutically acceptable salts, hydrates and solvates thereof.

Illustrative, but non-limiting, examples of the compounds of the present invention that are useful as GPR120 agonists are the following compounds:

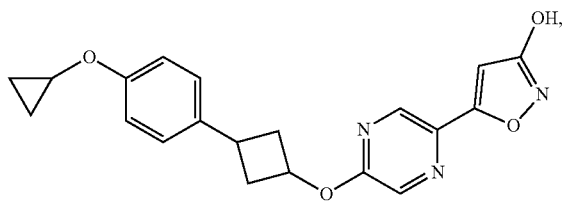

-continued

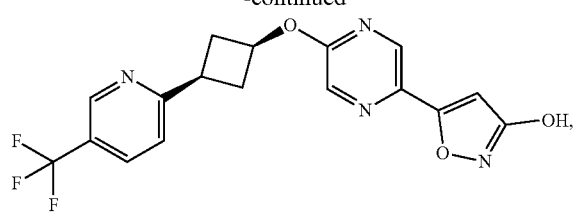
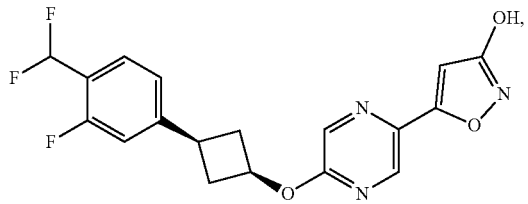
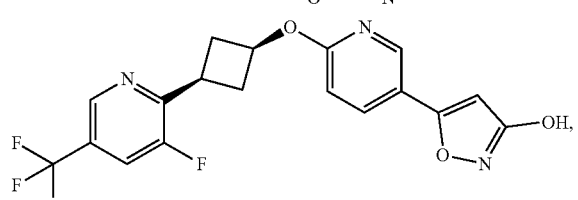
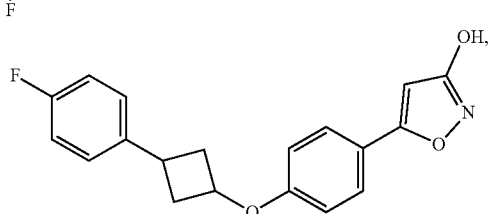
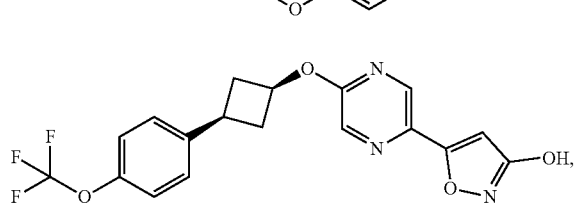
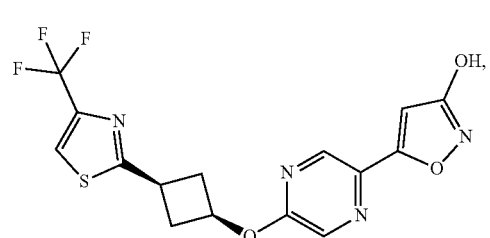
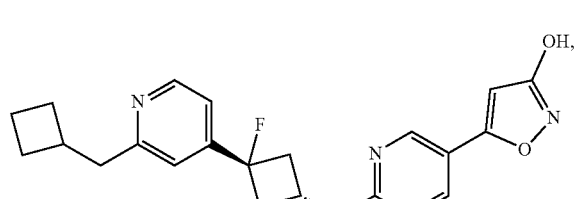
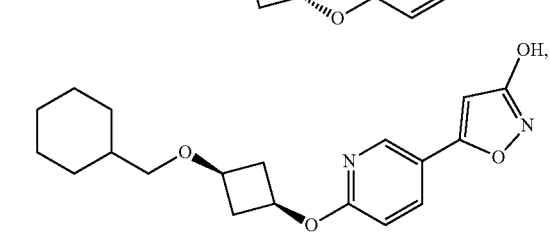

-continued

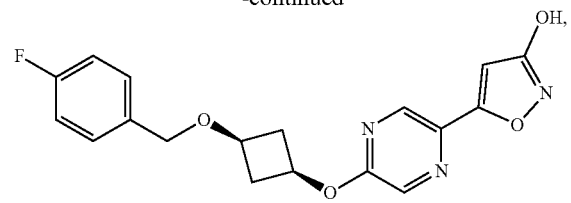
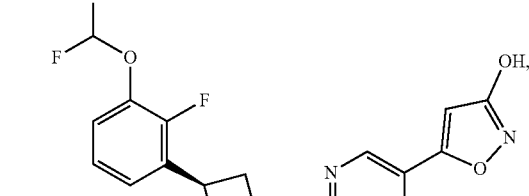
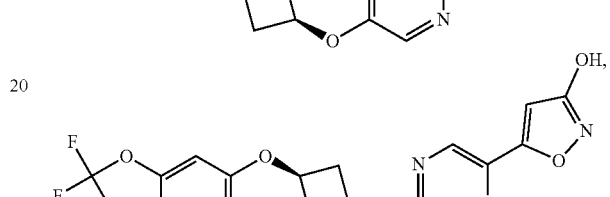
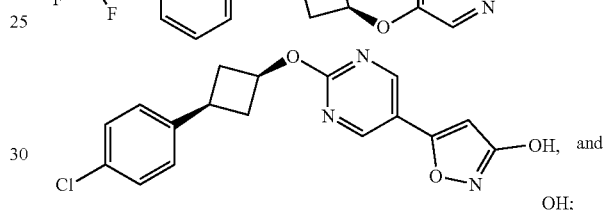
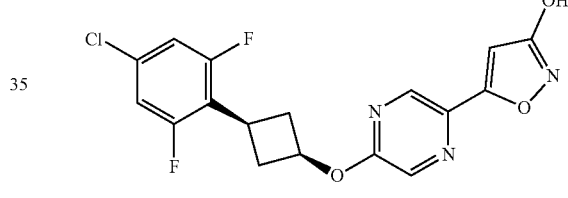

and pharmaceutically acceptable salts thereof.

The invention is described herein in detail using the terms defined below unless otherwise specified.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains up to 10 carbons which contain at least one carbon-carbon triple bond, and which may be linear or branched or combinations thereof. In one. embodiment, $C_{2-8}$alkynyl means a carbon chain with 2 to 8 carbons that contains one carbon-carbon triple bond. Examples of alkynyl include ethynyl, propargyl, 3-methyl-1-pentynyl, 2-heptynyl and the like.

"Cycloalkyl" means mono- or bicyclic, spiro or bridged saturated carbocyclic rings, each having from 3 to 10 carbon atoms. Examples of cycloalkyl include cyclopropyl, cyclobutyl, cyclopentyl, cyclohexyl, cycloheptyl, cyclooctyl, and decahydronaphthyl, and the like. In one embodiment, —C$_{3-10}$cycloalkyl is cyclohexane, cyclopentane, cyclopropyl, or cyclobutyl. In another embodiment, C$_{3-10}$cycloalkyl is cyclohexane. In another embodiment, C$_{3-10}$cycloalkyl is cyclohexane or cyclopentane. In another embodiment, C$_{3-10}$cycloalkyl is cyclopropyl or cyclobutyl.

"Cycloalkenyl" means nonaromatic, mono- or bicyclic, spiro or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, and the like.

"Cycloheteroalkyl" means nonaromatic, monocyclic, bicyclic, spiro or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens.

"Cycloheteroalkenyl" means nonaromatic monocyclic, bicyclic, spiro or bridged rings each having from 2 to 14 carbon atoms containing at least one double bond and containing 1, 2, 3, 4 or 5 heteroatoms selected from N, NH, O and S.

"Aryl" means a monocyclic or bicyclic ring system containing 5-10 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydro-naphthalene, and the like. In one embodiment of the present invention, aryl is phenyl and naphthalene. In one class of this embodiment, aryl is phenyl. In another class of this embodiment, aryl is naphthalene. In one embodiment, aryl is phenyl or naphthalene. In another embodiment, aryl is phenyl. In another embodiment, aryl is naphthalene.

"Heteroaryl" means a monocyclic or bicyclic ring system containing 5-10 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as a cycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, benzodioxane, oxazole, furan, benzoxazole, isoxazole, indoline, isoindoline, tetrazole, imidazole, oxadiazole, thiadiazole, triazole, benzothiazole, benzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydropyrrolopyrazole, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment, heteroaryl is pyridine, thiazole, oxazole, thiophene, benzodioxole, benzothiazole, and benzodioxine. In another embodiment, heteroaryl is pyridine, pyrimidine, pyrazine thiazole, benzothiazole, thiene or oxazole. In another embodiment, heteroaryl is pyridine, pyrimidine or pyrazine. In another embodiment, heteroaryl is pyridine, thiazole or benzothiazole. In another embodiment, heteroaryl is thiene. In another embodiment, heteroaryl is thiazole. In another embodiment, heteroaryl is pyridine or oxazole.

"Halogen" includes fluorine, chlorine, bromine and iodine. In one embodiment of the present invention, halogen is selected from fluorine, chlorine, and bromine. In another embodiment of the present invention, halogen is selected from fluorine, and chlorine. In another embodiment of the present invention, halogen is fluorine. In another embodiment of the present invention, halogen is chlorine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

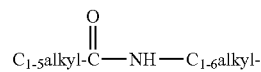

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Optical Isomers-Diastereomers-Geometric Isomers-Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Examples of tautomers include, but are not limited to:

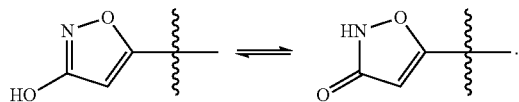 [SMILES: *c1cc(O)no1 ; *c1cc(=O)[nH]o1]

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I can be prepared without undue experimentation by conventional techniques well known to those skilled in the art or by processes analogous to those described in the Schemes and Examples herein using appropriate isotopically-enriched reagents and/or intermediates.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide, trifluoro acetate, and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like. It will be understood that, as used herein, references to the compounds of Formula I are meant to also include the pharmaceutically acceptable salts.

A pharmaceutical composition may also comprise a prodrug, or a pharmaceutically acceptable salt thereof, if a prodrug is administered.

The present invention also relates to a GPR120 function regulating agent containing a compound represented by formula I or a pharmaceutically acceptable salt thereof as an active ingredient. Particularly, the present invention relates to a GPR120 agonist containing a compound represented by formula I or a pharmaceutically acceptable salt thereof as an active ingredient.

The present invention also relates to an agent for treating and/or preventing diabetes, obesity, hyperlipidemia, NASH, or an inflammation related disorder, containing a compound represented by formula I or the pharmaceutically acceptable salt thereof, as an active ingredient.

Furthermore, the present invention relates to a pharmaceutical composition containing the compound represented by formula I and the pharmaceutically acceptable carrier.

The present also relates a compound represented by formula I for use as a medicament.

The present invention relates to the use of a compound represented by formula I or a pharmaceutically acceptable salt thereof, in the manufacture of a medicament for use in treating a condition selected from the group consisting of diabetes, hyperlipidemia, obesity, NASH, and inflammation related disorders.

The present invention relates to the treatment of a condition selected from the group consisting of diabetes, hyperlipidemia, obesity, NASH, and inflammation related disorders comprising administering to an individual in need of such treatment a pharmaceutical composition comprising the compound represented by formulas I to I-I.

A compound according to an embodiment of the present invention or the pharmaceutically acceptable salt thereof has a strong GPR120 function regulating action, particularly an agonist action, and may be useful for treating and/or preventing diabetes, obesity, hyperlipidemia, NASH, or an inflammation related disorder.

Compounds of the present invention are potent agonists of the GPR120 receptor. These compounds and pharmaceutically acceptable salts thereof are modulators of the receptor known as GPR120, and therefore may be useful in the treatment of diseases that are modulated by GPR120 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) Hyperapobetalipoproteinemia;
(11) atherosclerosis;
(12) inflammation related disorders;
(13) type 1 diabetes;
(14) insulin resistance;
(15) fatty liver; and
(16) non-alcoholic steatohepatitis (NASH).

Because the compounds are agonists of the GPR120 receptor, the compounds may be useful for lowering glucose, lipids, and insulin resistance and increasing insulin sensitivity in diabetic patients and in non-diabetic patients who have impaired glucose tolerance and/or are in a pre-diabetic condition. The compounds may be useful to ameliorate hyperinsulinemia, which often occurs in diabetic or pre-diabetic patients, by modulating the swings in the level of serum glucose that often occurs in these patients. The compounds may be useful for treating or reducing insulin resistance. The compounds may be useful for increasing insulin sensitivity. The compounds are useful for treating or preventing gestational diabetes.

Additionally, by keeping hyperglycemia under control, the compounds may be useful to delay or for preventing vascular restenosis and diabetic retinopathy.

The compounds of this invention may be useful in improving or restoring β-cell function, so that they may be useful in treating type 1 diabetes or in delaying or preventing a patient with type 2 diabetes from needing insulin therapy.

The compounds of this invention may be useful in treating inflammation related disorders such as obesity, diabetes, NASH, cancer, and cardiovascular disease.

The compounds, compositions, and medicaments as described herein may be further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds may be useful in treating neurological disorders such as Alzheimer's disease, multiple sclerosis, and schizophrenia. One aspect of the invention provides a method for the treatment and control of mixed or diabetic dyslipidemia, hypercholesterolemia, atherosclerosis, low HDL levels, high LDL levels, hyperlipidemia, NASH, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, rosuvastatin and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat,) or a monoamine neurotransmitter uptake inhibitor (e.g., sibutramine or phentermine). The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension, (22) fatty liver, (23) non-alcoholic steatohepatitis (NASH) and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors (e.g., sitagliptin, alogliptin, omarigliptin, linagliptin, vildagliptin);

(b) insulin sensitizers selected from the group consisting of (i) PPAR agonists and (ii) biguanides;

(c) insulin and insulin mimetics (e.g., insulin degludec, insulin glargine, insulin lispro);

(d) sulfonylureas and other insulin secretagogues;

(e) α-glucosidase inhibitors;

(f) glucagon receptor antagonists;

(g) GLP-1, GLP-1 mimetics, and GLP-1 receptor agonists (e.g., dulaglutide, exenatide, semaglutide, albiglutide, liraglutide, lixisenatide, taspoglutide);

(h) GIP,GIP mimetics, and GIP receptor agonists;

(i) PACAP, PACAP mimetics, and PACAP receptor 3 agonists;

(j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPAR α/γdual agonists, (vi) inhibitors of cholesterol absorption, (vii) acyl CoA:cholesterol acyltransferase inhibitors, and (viii) anti-oxidants;

(k) PPARδ agonists;

(l) SGLT inhibitors (e.g., empagliflozin, dapagliflozin, canagliflozin, BI-10773, tofogliflozin, ipragliflozin, LX-4211, PF-4971729, remogloflozin, TS-071, ertugliflozin);

(m) anti-obesity compounds;

(n) ileal bile acid transporter inhibitors;

(o) anti-inflammatory agents excluding glucocorticoids;

(p) protein tyrosine phosphatase-1B (PTP-1B) inhibitors;

(q) antihypertensives including those acting on the angiotensin or renin systems, such as angiotensin converting enzyme inhibitors, angiotensin II receptor antagonists or renin inhibitors, (e.g., lisinopril, losartan); and (r) GPR-40 agonists; said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of formula I or the other drugs may have utility, where the combination of the drugs together are safer or more effective than either drug alone. Such other drug(s) may be administered, by a route and in an amount commonly used therefore, contemporaneously or sequentially with a compound of formula I. When a compound of formulas I is used contemporaneously with one or more other drugs, a pharmaceutical composition in unit dosage form containing such other drugs and the compound of formula I are preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, omarigliptin, linagliptin, vildagliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., MK-3577, MK-0893, LY-2409021 and KT6-971);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, cerivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof;

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, ertugliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab); and

(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), omarigliptin, SYR-472, teneligliptin, KRP104, TS021, AMG222, SK0403, LC15-0444, vildagliptin, saxagliptin, alogliptin, melogliptin, linagliptin, and pharmaceutically acceptable salts thereof, and fixed-dose combinations of these compounds with metformin hydrochloride, pioglitazone, rosiglitazone, simvastatin, atorvastatin, rosuvastatin, ertugliflozin, ipragliflozin, or a sulfonylurea.

Antiobesity compounds that can be combined with compounds of formulas I to I-I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); O3 adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents,* 11: 1677-1692 (2001); D. Spanswick and K. Lee, "Emerging antiobesity drugs," *Expert Opin. Emerging Drugs,* 8: 217-237 (2003); J. A. Fernandez-Lopez, et al., "Pharmacological Approaches for the Treatment of Obesity," *Drugs,* 62: 915-944 (2002); and K. M. Gadde, et al., "Combination pharmaceutical therapies for obesity," *Exp. Opin. Pharmacother.,* 10: 921-925 (2009).

In another aspect of the invention, a pharmaceutical composition is disclosed which comprises one or more of the following agents:

(a) a compound of structural formulas I to I-I;

(b) one or more compounds selected from the group consisting of:

(1) dipeptidyl peptidase-IV (DPP-4) inhibitors;

(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;

(3) sulfonylurea and non-sulfonylurea insulin secretagogues, (e.g., tolbutamide, glyburide, glipizide, glimepiride, mitiglinide, and meglitinides, such as nateglinide and repaglinide);

(4) α-glucosidase inhibitors (e.g., acarbose, voglibose and miglitol);

(5) glucagon receptor antagonists;

(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe);
(7) HDL-raising drugs;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);
(11) glucokinase activators (GKAs) (e.g., AZD6370);
(12) inhibitors of 11β-hydroxysteroid dehydrogenase type 1 (e.g., such as those disclosed in U.S. Pat. No. 6,730,690; WO 03/104207; and WO 04/058741);
(13) inhibitors of cholesteryl ester transfer protein (CETP), (e.g., torcetrapib and anacetripib);
(14) inhibitors of fructose 1,6-bisphosphatase (e.g., such as those disclosed in U.S. Pat. Nos. 6,054,587; 6,110,903; 6,284,748; 6,399,782; and 6,489,476);
(15) inhibitors of acetyl CoA carboxylase-1 or 2 (ACC1 or ACC2);
(16) AMP-activated Protein Kinase (AMPK) activators;
(17) agonists of the G-protein-coupled receptors: (i) GPR-109, (ii) GPR-119 (e.g., MBX2982, and PSN821), and (iii) GPR-40;
(18) SSTR3 antagonists (e.g., such as those disclosed in WO 2009/011836);
(19) neuromedin U receptor agonists (e.g., such as those disclosed in WO2009/042053, including, but not limited to, neuromedin S (NMS));
(20) inhibitors of stearoyl-coenzyme A delta-9 desaturase (SCD);
(21) GPR-105 antagonists (e.g., such as those disclosed in WO 2009/000087);
(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin, ertugliflozin, ipragliflozin and remogliflozin; and SGLT-3);
(23) inhibitors of acyl coenzyme A:diacylglycerol acyltransferase 1 and 2 (DGAT-1 and DGAT-2);
(24) inhibitors of fatty acid synthase;
(25) inhibitors of acyl coenzyme A:monoacylglycerol acyltransferase 1 and 2 (MGAT-1 and MGAT-2);
(26) agonists of the TGR5 receptor (also known as GPBAR1, BG37, GPCR19, GPR131, and M-BAR);
(27) bromocriptine mesylate and rapid-release formulations thereof, and
(28) IL-1b antibodies (e.g., XOMA052, and canakinumab); and
(c) a pharmaceutically acceptable carrier.

When a compound of the present invention is used contemporaneously with one or more other drugs, a pharmaceutical composition containing such other drugs in addition to the compound of the present invention may be employed. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The following abbreviations may be used in the synthetic schemes, intermediates or Examples: ACN is acetonitrile; AcOH is acetic acid; Ac$_2$O is acetic anhydride; anhyd. or anhydr. is anhydrous; aq. is aqueous; Ar is aryl; atm is atmosphere; BINAP is (2,2'-bis(diphenyl-phosphino)-1,1'-binaphthyl); (BOC)$_2$O is boc anhydride or di-tert-butyl dicarbonate; n-BuLi is n-butyl lithium; tert-BuOH or t-BuOH is tert-butanol; (t-Bu)$_3$PHBF$_4$ is tri-tert-butylphosphine tetrafluoroborate; t-Busphos precatalyst is chloro(2-ditert-butyl-2',6'-dimethoxy-1,1'-biphenyl) [2-(2-aminoethyl-phenyl)]palladium(II)dichloromethane adduct; Bu$_4$NI is tetrabutyl ammonium iodide; $^t$BuOK is potassium tert-butoxide; $^t$BuONa is sodium tert-butoxide; ° C. is degree Celsius; CataCXium A is di(1-adamantyl)-n-butylphosphine; CDCl$_3$ is deuterated chloroform; CD$_3$OD is deuterated methanol; Celite™ is diatomaceous earth; conc. is concentrated; d is day or days; DAST is diethylaminosulfur trifluoride; DCM is dichloromethane; DEA is N,N-diisopropylethylamine; DEAD diethyl azodicarboxylate; DIAD is diisopropyl azodicarboxylate; DIBAL is diisobutylaluminum hydride; DIEA is diisopropylethylamine; DMA is N,N-dimethylacetamide; DMF is dimethylformamide; DMP is Dess-Martin periodinane; DMS is dimethyl sulfide; DMSO is dimethylsulfoxide; Et is ethyl; EA or EtOAc is ethyl acetate; Et$_2$O is diethyl ether; EtOH is ethanol; Et$_2$Zn is diethylzinc; eq is equivalent; g is grams; Et$_3$N is triethylamine; Et$_3$SiH is triethylsilane; iPrOH is isopropyl alcohol; g is gram; h is hour; HATU is 1-[bis(dimethylamino)methylene]-1H-1,2,3-triazolo-[4,5-b]pyridinium 3-oxide-hexafluoro-phosphate); HPLC is high performance liquid chromatography; [Ir(COD)Cl]$_2$ is bis(1,5-cyclooctadiene)-diiridium(I) dichloride; IPA is isopropyl alcohol; KHMDS is potassium hexamethyldisilizide; KOTMS is potassium trimethylsiloxide; LAH is lithium aluminum hydride; LC-MS or LCMS is liquid chromatography mass spectrum; LDA is lithium diisopropylamide; LHMDS or LiHMDS is lithium bis(trimethylsilyl)amide; LiTMP is lithium tetramethylpiperidide; M is molar; m-CPBA or mCPBA is meta-chloroperoxybenzoic acid; Me is methyl; MeCN is acetonitrile; MeI is methyl iodide; MeOH is methanol; mg is milligram; MHz is megaHertz; min is minute(s); mmol is millimoles; ml or mL is milliliter; MOM is methoxymethyl; mPa is millipascal; N is normal; NaBH$_4$ is sodium borohydride; NaHCO$_3$ is sodium bicarbonate; NaHMDS is sodium bis(trimethylsily) amide; nBuLi is n-butyllithium; NBS is N-bromosuccinimide; NCS is N-chlorosuccinimide; NMP is N-methylpyrrolidone; NMR is nuclear magnetic resonance; PCC is pyridinium chlorochromate; Pd—C or Pd/C is palladium(0) on carbon; $PdCl_2$(dtbpf) is [1,1'-Bis(di-tert-butylphosphino)-ferrocene]-dichloropalladium(II); PE is petroleum ether; $Pd(PPh_3)_4$ is tetrakis(triphenyl-phosphine)palladium (0); $PdCl_2$(dppf) or $Pd(dppf)Cl_2$ is [1,1'-Bis(diphenyl-phosphino)ferrocene] dichloropalladium (II); $Pd(OAc)_2$ is palladium (II) acetate; $Pd_2(dba)_3$ is tris(dibenzylideneacetone) dipalladium(0); $Pd(OH)_2$/C is palladium(II)hydroxide on carbon; $PPh_3$ is triphenyl phosphine; Prep-HPLC is preparative high performance liquid chromatography; psi is pounds per square inch; PTLC or prep tlc is preparative thin layer chromatography; rac is racemic; rt or RT or r.t. is room temperature; $Rh(acac)(C_2H_4)$ is acetylacetonatobis(ethylene)rhodium(I); RuPhos precatalyst is 2-dicyclohexylphosphono-2',6'-diisopropoxy-biphenyl; sat. or satd. is saturated; soln. is solution; SelectFluor is 1-chloromethyl-4-fluoro-1,4-diazoniabicyclo-[2.2.2]-octane bis(tetrafluoroborate); SFC is supercritical fluid chromatography; SPHOS precatalyst is 2-dicyclohexylphosphino-2',6'-dimethoxybiphenyl; TBAB is tetrabutylammonium bromide; TBAF is tetra-n-butyl-ammonium fluoride; TBAI is tetra-n-butyl-ammonium iodide; TBS is tert-butyldimethyl-silyl; TEA is triethylamine; $Tf_2O$ is triflic anhydride or tri-fluoromethanesulfonic anhydride; TFA is trifluoroacetic acid; TFAA is trifluoroacetic anhydride: THF is tetrahydrofuran; TIPS-Cl is triisopropyl silylchloride; TLC is thin layer chromatography; TMP is tetramethyl-piperidine; TMSCl or TMS-Cl is trimethylsilyl chloride; TRIXIEPHOS is 2-Di-t-butylphosphino-1,1'-binaphthyl; PTLC or prep-TLC is preparative thin layer chromatography; μL or μl is microliter(s); μmmol is micromole(s); XantPhos is 4,5-bis(diphenylphosphino)-9,9-dimethyl-xanthene; and XPHOS, XPhos or Xphos precatalyst is 2-dicyclohexylphosphino-2' 4'6'-triisopropylbiphenyl.

Compounds were named using either ACD/NAME (version 11.02) or ChemBioDraw Ultra (version 13.0.2.3021) software.

GENERAL SCHEMES

The compounds of the invention can be prepared using the synthetic schemes described herein as well as any of several alternate methods which will be apparent to a chemist skilled in the art.

Scheme 1

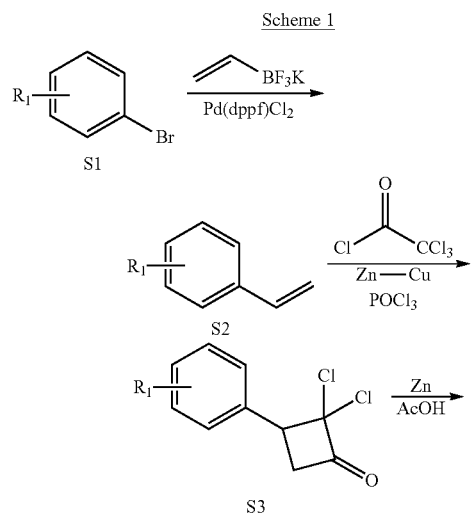

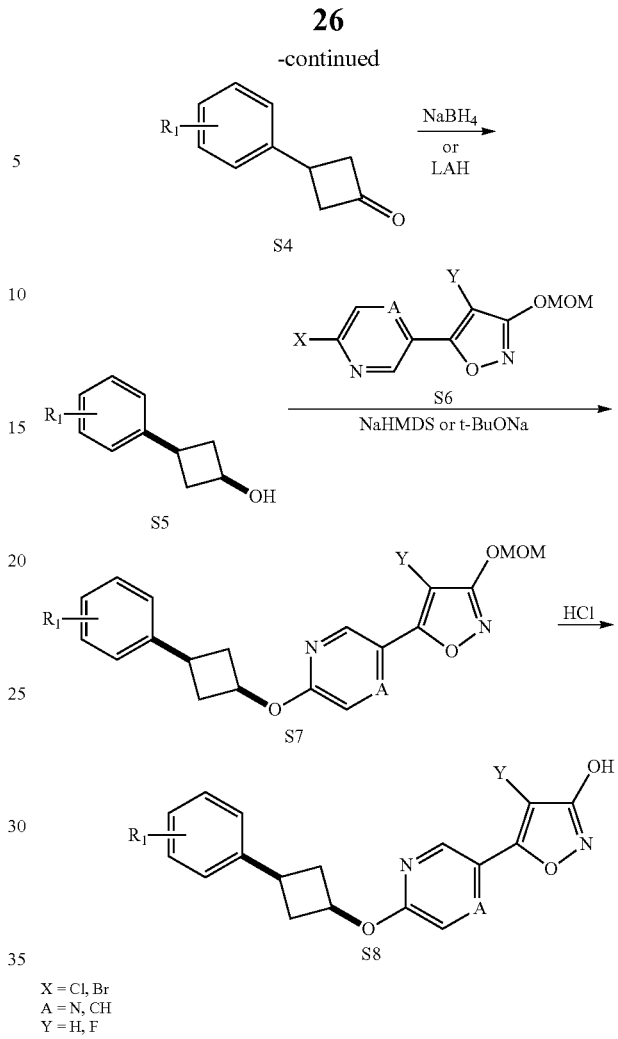

X = Cl, Br
A = N, CH
Y = H, F

Compounds such as S8 can be obtained by first reacting aryl bromide derivative S1 with potassium trifluoro(vinyl) borate using a palladium catalyst to give S2, which can undergo a [2+2] cycloaddition reaction with 2,2,2-trichloroacetyl chloride to yield 2,2-dichloro-3-phenyl cyclobutanone derivative S3. A ketone reduction reaction using a reducing agent like $NaBH_4$ or LAH can generate cis-3-phenyl cyclobutanol S5. S5 then undergoes a nucleophilic aromatic substitution reaction with S6 to afford S7 and S8 is obtained after treating S7 with an acid, such as HCl.

Scheme 2

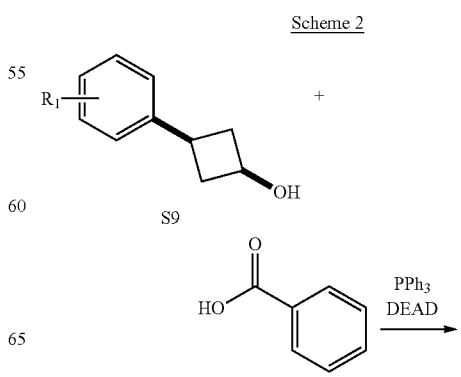

-continued

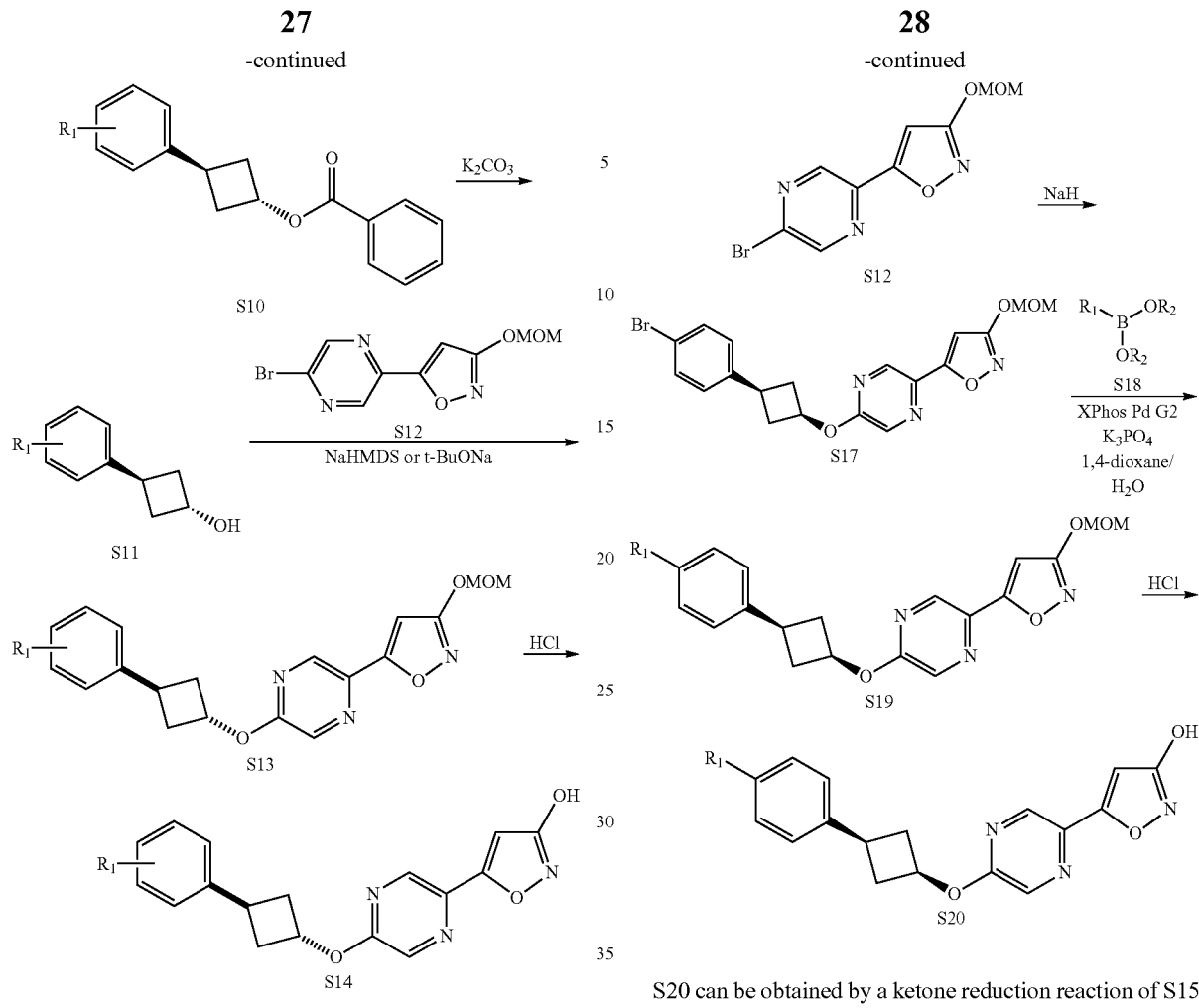

Intermediates such as S9 can be synthesized according the procedure in Scheme 1. S14 can be obtained by a Mitsunobu reaction of S9 with benzoic acid to give S10, followed by the removal of benzoyl group with $K_2CO_3$ to yield S11 as a trans stereoisomer. S11 can then undergo a nucleophilic aromatic substitution reaction with 5-(5-bromopyrazin-2-yl)-3-(methoxymethoxy)-isoxazole S12 to afford S13. S14 is obtained after treating S13 with an acid, such as HCl.

S20 can be obtained by a ketone reduction reaction of S15 to give S16 as a cis stereoisomer, which then can undergo a nucleophilic aromatic substitution reaction with 5-(5-bromopyrazin-2-yl)-3-(methoxymethoxy)isoxazole S12 to afford S17. A Suzuki reaction with boronic ester derivative S18 in the presence of a palladium catalyst can yield S19. S19 can be deprotected under acidic condition to yield S20.

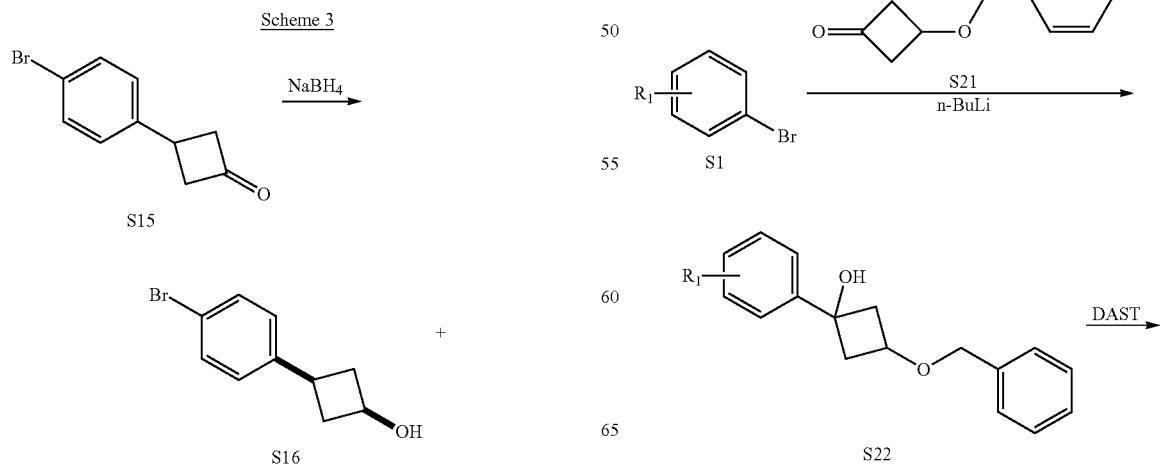

-continued

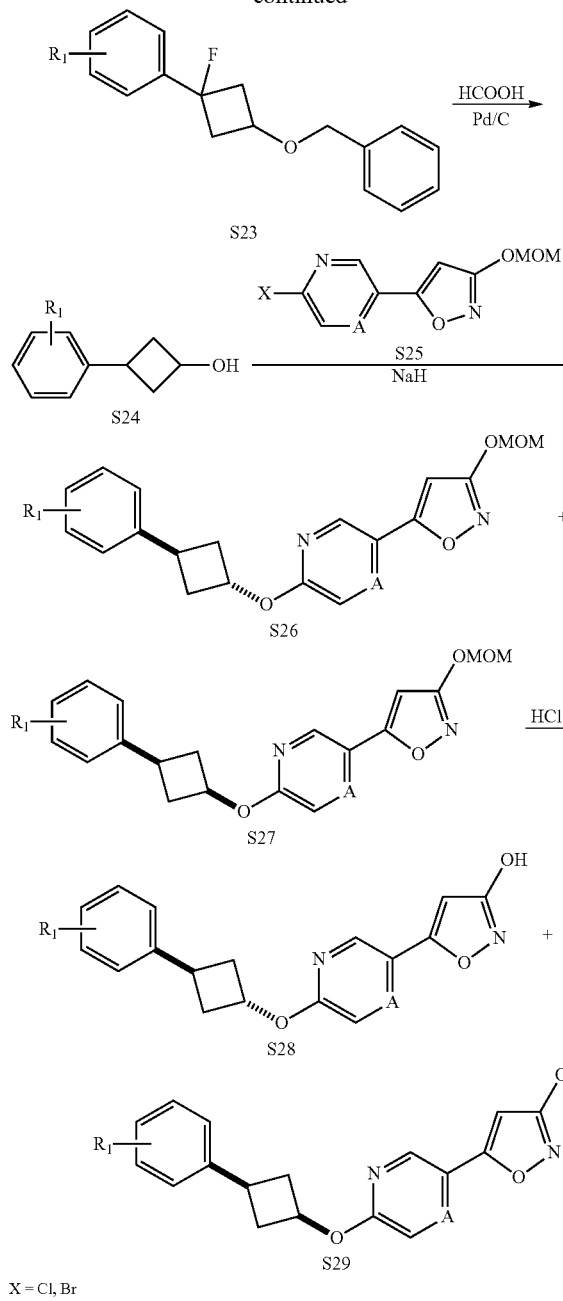

X = Cl, Br
A = N, CH

S28 and S29 can be obtained by first reacting the lithiated aryl bromide S1 with cyclobutanone S21 to give S22 as a mixture of stereoisomers, which can be fluorinated with DAST to generate S23 as a mixture of 2 stereoisomers. Defluorination and deprotection reactions can be achieved in one pot via the hydrogenation of S23 to yield S24 as a mixture of cis and trans stereoisomers in the presence of palladium on carbon and ammonium formate. The mixture of S24 can then be taken on for a nucleophilic aromatic substitution reaction with S25 using a base like NaH to afford a mixture of S26 and S27, which can be separated on normal phase column chromatography. S26 and S27 can then be treated with acid, such as HCl, to afford S28 and S29 respectively.

Scheme 5

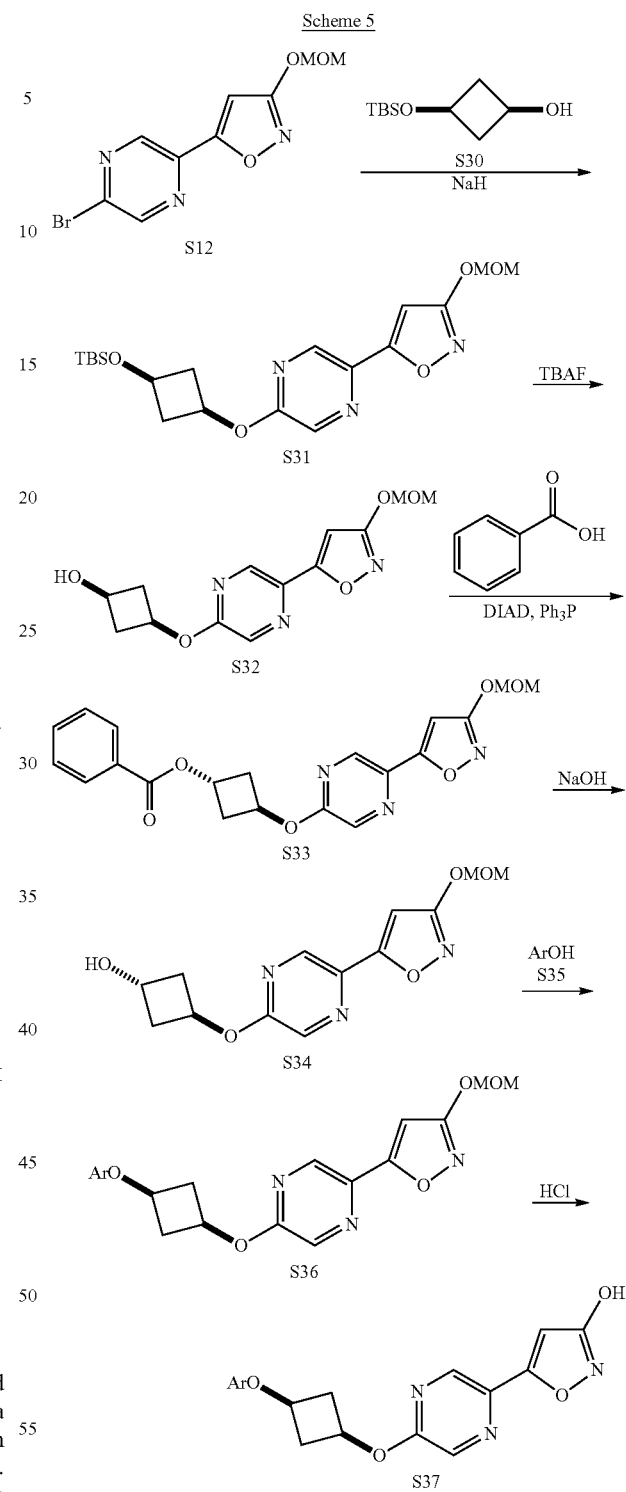

S37 can be obtained via a nucleophilic aromatic substitution reaction of S12 with cyclobutanol derivative S30 using a base like NaH to afford S31. TBS protecting group of S31 can be removed by TBAF followed by a Mitsunobu reaction of the resulting alcohol S32 with benzoic acid to yield S33. The removal of the benzoyl group of S33 can be done using NaOH followed by a subsequent aryl ether formation under Mitsunobu condition generated S36 with stereochemistry inversion to give cis stereoisomer in S36, which can then be treated with an acid, like HCl, to afford S37.

Scheme 6

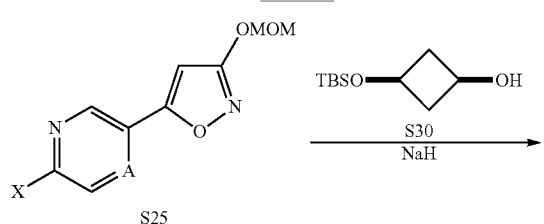

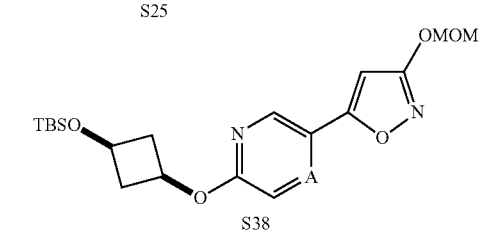

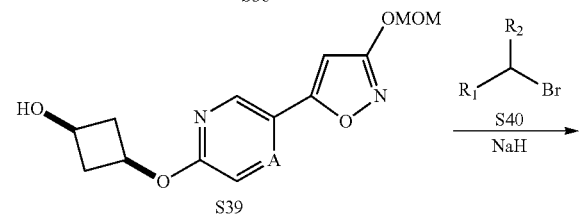

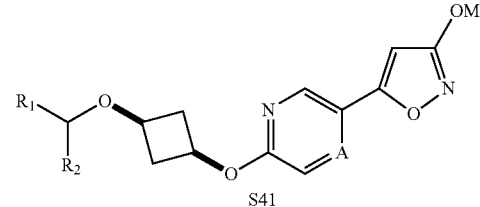

X = Cl, Br
A = N, CH

S42 can be obtained via a nucleophilic aromatic substitution reaction of S25 with cyclobutanol derivative S30 using a base like NaH to afford S38. The TBS protecting group of S38 can be removed by TBAF followed by an alkylation reaction of the resulting alcohol S39 with benzyl bromide S40 to yield S41. S41 can then be treated with an acid like HCl solution to afford S42.

Scheme 7

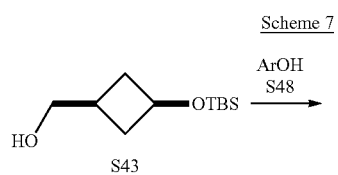

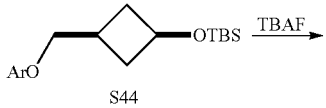

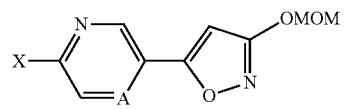

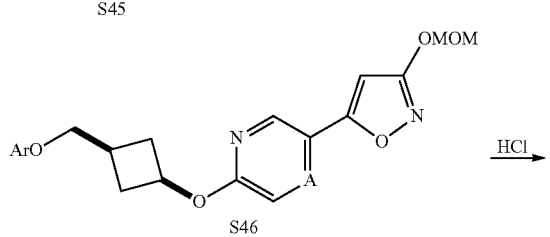

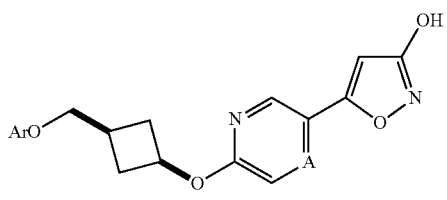

X = Cl, Br
A = N, CH

S47 can be obtained by a Mitsunobu reaction of alcohol S43 with phenol S48 to give S44, which is then deprotected with a reagent like TBAF to yield the secondary alcohol S45. S45 can undergo a nucleophilic aromatic substitution reaction with S25 using a base like NaH to generate S46. S46 can then be treated with an acid like HCl to afford S47.

Scheme 8

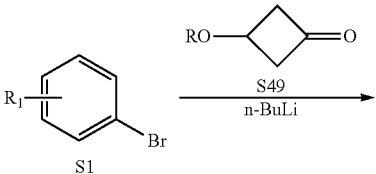

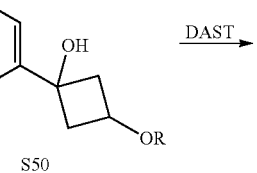

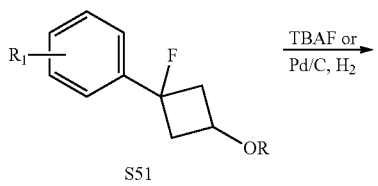

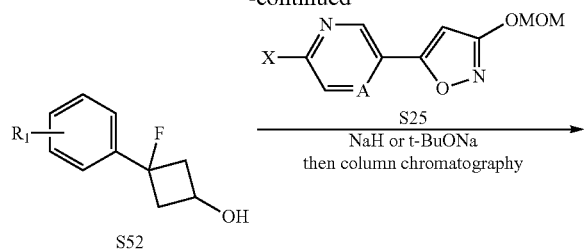
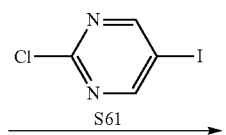
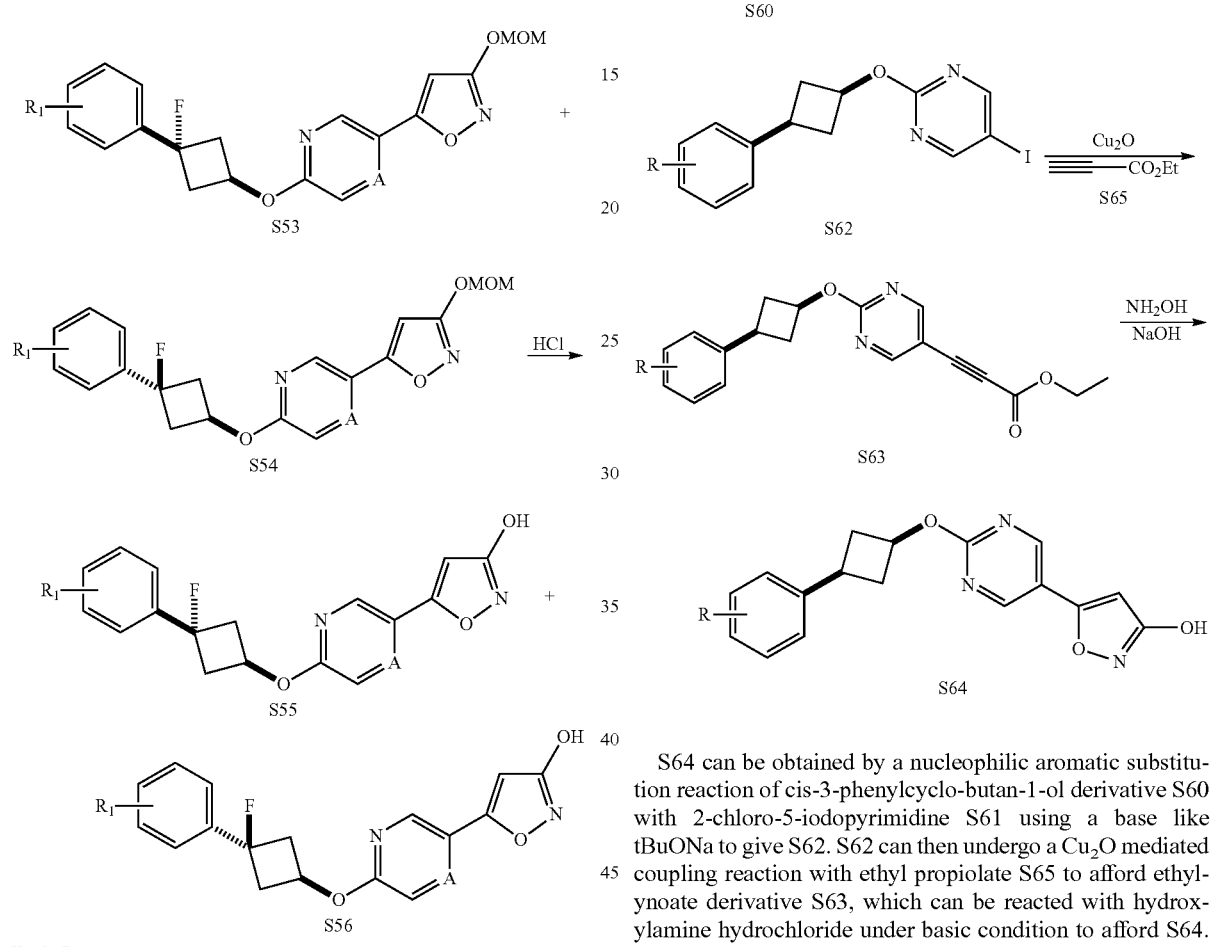

X = Cl, Br
A = N, CH
R = TBS or Bn

S55 and S56 can be obtained by first reacting aryl lithium reagent derived from aryl bromide S1 with either TBS protected or benzyl protected 3-hydroxycyclobutan-1-one S49 to give S50 as a mixture of cis and trans stereoisomers. The tertiary alcohol in S50 can then be converted to fluoride using DAST as the fluorination reagent, followed by a deprotection condition such as TBAF to remove the TBS protecting group, or hydrogenation to remove the benzyl protecting group, to afford S52 as a mixture of cis and trans stereoisomers. The mixture of S52 can then undergo a nucleophilic aromatic substitution reaction with S25 to afford a mixture of S53 and S54, which can be separated by either normal phase or reverse phase column chromatography. S55 and S56 can be obtained by treating S53 and S54 with an acid like HCl to remove the MOM protecting group.

S64 can be obtained by a nucleophilic aromatic substitution reaction of cis-3-phenylcyclo-butan-1-ol derivative S60 with 2-chloro-5-iodopyrimidine S61 using a base like tBuONa to give S62. S62 can then undergo a Cu$_2$O mediated coupling reaction with ethyl propiolate S65 to afford ethylynoate derivative S63, which can be reacted with hydroxylamine hydrochloride under basic condition to afford S64.

Scheme 10

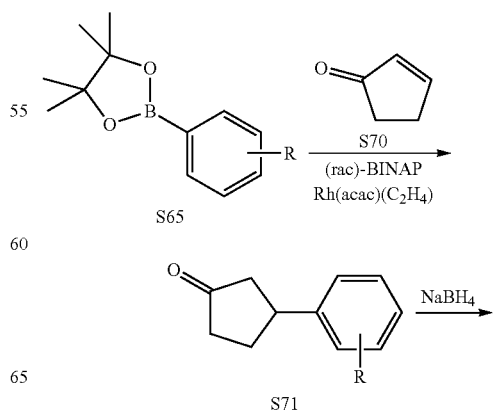

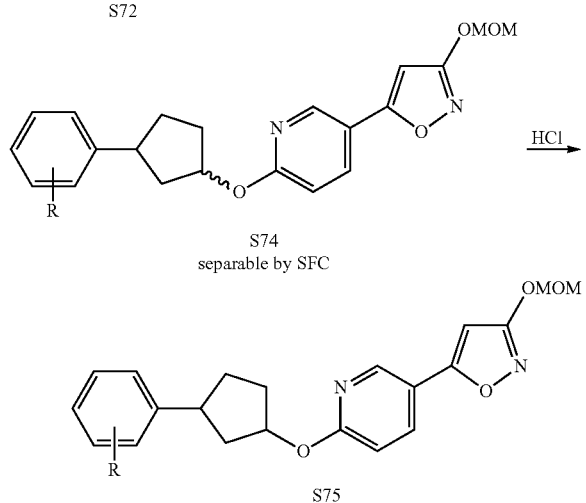

S75 can be obtained by a rhodium catalyzed conjugated addition of aryl boronate S65 with cyclopent-2-en-1-one S70 using racemic BINAP as the ligand to give a mixture of enantiomers of S71. The ketone in S71 can then be reduced to alcohol S72, non-selectively to yield a mixture of 4 stereoisomers. The mixture of S72 can be reacted with 5-(6-chloropyridin-3-yl)-3-(methoxymethoxy)isoxazole S73 via a nucleophilic aromatic substitution reaction using a base like NaHMDS to generate S74 as a mixture of 4 stereoisomers, which can be separated by SFC to give 4 single stereoisomers. The four different single stereoisomers of S74 can be converted to the final product S75 by treating with an acid like HCl.

Intermediate 1

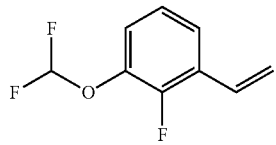

1-(difluoromethoxy)-2-fluoro-3-vinylbenzene

Step A: 1-bromo-3-(difluoromethoxy)-2-fluorobenzene. To a solution of 3-bromo-2-fluorophenol (5 g, 26.2 mmol) and sodium 2-chloro-2,2-difluoroacetate (4.79 g, 31.4 mmol) in DMF (50 ml) was added $Cs_2CO_3$ (17.06 g, 52.4 mmol). The resultant mixture was stirred at 100° C. for 4 h, then the reaction was diluted with $H_2O$ (30 mL) and extracted with EA (3×30 ml). The combined organic layers were washed with brine (30 mL), dried over $Na_2SO_4$, filtered and concentrated to provide the title compound, which was used in the next step without further purification.

Step B: 1-(difluoromethoxy)-2-fluoro-3-vinylbenzene. To a solution of 1-bromo-3-(difluoromethoxy)-2-fluorobenzene (3 g, 12.45 mmol), potassium trifluoro-(vinyl)borate (3.33 g, 24.90 mmol) and $Na_2CO_3$ (3.96 g, 37.3 mmol) in 1,4-dioxane (50.0 ml) and water (10 ml) was added $PdCl_2(dppf)$ (0.911 g, 1.245 mmol). The resultant mixture was stirred at 100° C. for 12 h, then diluted with $H_2O$ (30 ml) and extracted with EA (3×30 ml). The combined organic layers were washed with brine (30 ml), dried over $Na_2SO_4$, filtered and concentrated. The resulting residue was purified by column chromatography ($SiO_2$ eluting with PE) to give the title compound.

Intermediate 2

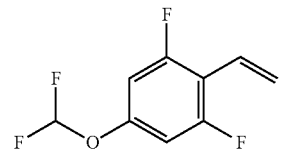

5-(difluoromethoxy)-1,3-difluoro-2-vinylbenzene

Step A: 2-bromo-5-(difluoromethoxy)-1,3-difluorobenzene. $Cs_2CO_3$ (2339 mg, 7.18 mmol) was added to a mixture of 4-bromo-3,5-difluorophenol (1000 mg, 4.78 mmol) and sodium 2-chloro-2,2-difluoroacetate (1459 mg, 9.57 mmol) in DMF (9570 μl) at 90° C. and then stirred for 2 h. Then the mixture was filtered to remove the solid, and washed with $Et_2O$. The filtrate was concentrated to remove solvent. The resulting residue was purified by silica gel column chromatography to give the title compound.

Step B: 5-(difluoromethoxy)-1,3-difluoro-2-vinylbenzene. To a solution of 2-bromo-5-(difluoromethoxy)-1,3-difluorobenzene (1000 mg, 3.86 mmol), potassium vinyltrifluroborate (776 mg, 5.79 mmol) and $Na_2CO_3$ (818 mg, 7.72 mmol) in dioxane (11.700 ml) and water (1.170 ml) was added [1,1'-bis(diphenylphoshino)ferrocene]dichloropalladium(II) (PdCl2(dppf)) (283 mg, 0.386 mmol). The reaction mixture was stirred at 100° C. overnight, then poured into water (100 mL), and extracted with ether (×4). The combined organic layers were dried over $Na_2SO_4$, and filtered. The filtrate was concentrated to give a residue, which was purified with normal phase silica chromatography to give the title compound.

Intermediate 3

2-(difluoromethoxy)-1,3-difluoro-5-vinylbenzene

Step A: 5-bromo-2-(difluoromethoxy)-1,3-difluorobenzene. $Cs_2CO_3$ (2339 mg, 7.18 mmol) was added to a mixture of 4-bromo-2,6-difluorophenol (1000 mg, 4.78 mmol) and sodium 2-chloro-2,2-difluoroacetate (1459 mg, 9.57 mmol) in DMF (9570 μl) at 90° C. and then stirred for 2 h. After 2 h, the mixture was filtered to remove the solid, washed with $Et_2O$. The filtrate was concentrated to remove solvent. The afforded residue was purified by silica gel column chromatography to give the title compound.

Step B: 2-(difluoromethoxy)-1,3-difluoro-5-vinylbenzene. To a solution of 5-bromo-2-(difluoromethoxy)-1,3-difluorobenzene (900 mg, 3.47 mmol), potassium vinyltrifluoroborate (698 mg, 5.21 mmol) and $Na_2CO_3$ (737 mg, 6.95 mmol) in dioxane (13.80 ml) and water (1.38 ml) was added [1,1'-bis(diphenylphoshino)ferrocene]dichloropalladium(II) (PdCl$_2$(dppf)) (254 mg, 0.347 mmol). The reaction mixture was stirred at 100° C. overnight, then poured into water (100 mL), and extracted with ether (×4). The combined organic layers were dried over Na$_2$SO$_4$, and filtered. The filtrate was concentrated, and the resulting residue was purified with normal phase silica gel chromatography to give the title compound.

Intermediate 4

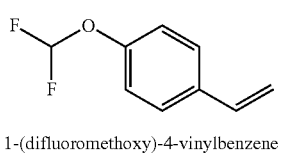

1-(difluoromethoxy)-4-vinylbenzene

To a solution of 4-vinylphenol (500 mg, 4.16 mmol) and sodium 2-chloro-2,2-difluoroacetate (1269 mg, 8.32 mmol) in DMF (25 ml) was added Cs$_2$CO$_3$ (2034 mg, 6.24 mmol). The reaction was stirred at 80° C. overnight, then cooled, diluted with EA(80 ml), and washed with water (2×40 mL). The organic layer was dried over Na$_2$SO$_4$ and filtered. The filtrate was evaporated under reduced pressure and the resulting residue was purified by flash column chromatography on silica gel (eluting with EA/Hexane) to afford the title compound.

Intermediate 5

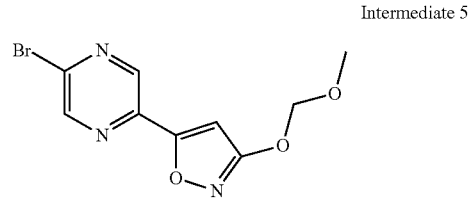

2-bromo-5-[3-(methoxymethoxy)-1,2-oxazol-5-yl]pyrazine

Step A: 2-bromo-5-iodopyrazine. Into a 20-L 4-necked round-bottom flask was placed a solution of 5-bromopyrazin-2-amine (400 g, 2.30 mol) in ethylene glycol dimethyl ether (8 L), iodocopper (131 g, 687.84 mmol), diiodane (293 g, 1.15 mol), iodopotassium (380 g, 2.29 mol) and 3-methylbutyl nitrite (1800 mL, 11.5 mol). The resulting solution was stirred for 30 min at 60° C., then extracted with 2×10 L of ethyl acetate. The combined organic layers were dried over anhydrous sodium sulfate and concentrated under vacuum to afford the title compound.

Step B: ethyl 3-(5-bromopyrazin-2-yl)prop-2-ynoate. Into a 20-L 4-necked round-bottom flask was placed a solution of TEA (682.5 g, 6.74 mol) in 1,4-dioxane (8.5 L), dibromozinc (374.5 g, 1.69 mol), tetrakis(triphenylphosphane) palladium (82.5 g, 71.39 mmol), ethyl prop-2-ynoate (345 g, 3.52 mol), and a solution of 2-bromo-5-iodopyrazine (400 g, 1.40 mol) in 1,4-Dioxane (500 mL). The resulting mixture was stirred for 10 min at 80° C., then diluted with 30 L of water/ice, and extracted with 2×10 L of ethyl acetate. The combined organic layers were dried in an oven under reduced pressure and concentrated under vacuum. The resulting residue was purified on a silica gel column with ethyl acetate/petroleum ether (1:30) to provide the title compound.

Step C: 5-(5-bromopyrazin-2-yl)-1,2-oxazol-3-ol. Into a 20-L 4-necked round-bottom flask, was placed a solution of hydroxylamine (161 g, 2.33 mol) in ethanol (9500 mL) and NaOH (181 g, 4.53 mol) in water (500 mL). To this was added dropwise a solution of ethyl 3-(5-bromo-pyrazin-2-yl)-prop-2-ynoate (500 g, 1.96 mol) in ethanol (500 mL) with stirring at −48° C. for 1 hr, followed by −40° C. for 40 min. To the reaction mixture was added TEA (990 g, 9.80 mol). The resulting mixture was stirred for 2 h at 40° C. then additional 2 h at 60° C. Then the reaction mixture was diluted with 15 L of water/ice, and the pH of the solution was adjusted to pH 6 with hydrogen chloride/H$_2$O. The resulting solution was extracted with ethyl acetate (2×10 mL). The combined organic layers were dried over anhydrous sodium sulfate and concentrated under vacuum to afford the title compound.

Step D: 2-bromo-5-[3-(methoxymethoxy)-1,2-oxazol-5-yl]pyrazine. Into a 5-L 4-necked round-bottom flask, was placed a solution of 5-(5-bromopyrazin-2-yl)-1,2-oxazol-3-ol (300 g, 1.24 mol) in tetrahydrofuran (3000 mL), and TEA (1252 g, 12.37 mol). Then bromo(methoxy)-methane (387 g, 3.10 mol) was added dropwise with stirring at 0° C. The reaction mixture was stirred for 10 min at 0° C., then diluted with 30 L of water/ice. The resulting solids were collected by filtration to afford the title compound. $^1$H NMR (300 MHz, CDCl$_3$) δ 3.59 (3H, s), 5.39 (2H, s), 6.69 (1H, s), 8.73 (1H, s), 8.86 (1H, s). LC-MS (ES, m/z): 286 [M+H]$^+$.

Intermediate 6

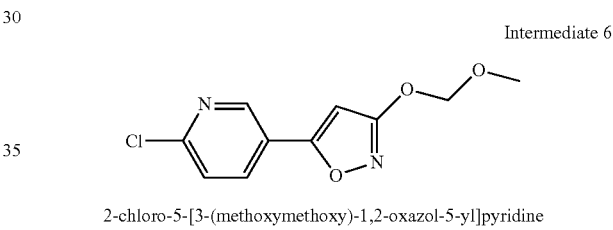

2-chloro-5-[3-(methoxymethoxy)-1,2-oxazol-5-yl]pyridine

Step A: 3-(6-chloropyridin-3-yl)prop-2-ynoate. Into a 20-L 4-necked round-bottom flask, purged and maintained with an inert atmosphere of nitrogen, was placed 2-chloro-5-iodopyridine (900 g, 3.76 mol), ethyl prop-2-ynoate (1107 g, 11.28 mol), and N,N-dimethylformamide (12000 mL). Then Cu$_2$O (540 g, 3.77 mol) was added in portions at 100° C. The reaction mixture was stirred overnight at 110° C., then cooled to room temperature, and diluted with 5000 mL of EA. The resulting solids were filtered out and the filtrate was washed with 2×3000 mL of H$_2$O. The mixture was concentrated under vacuum and the resulting residue was purified via silica gel column eluting with ethyl acetate/petroleum ether (1:20-1:5) to afford the title compound.

Step B: 5-(6-chloropyridin-3-yl)-1,2-oxazol-3-ol. Into a 2 L 4-necked round-bottom flask, purged and maintained with an inert atmosphere of nitrogen, was placed ethyl 3-(6-chloropyridin-3-yl)-prop-2-ynoate 950 g, 4.53 mol), H$_2$NOH.HCl (950 g, 13.77 mol,), ethanol (6000 mL) and tetrahydrofuran (1500 mL). Then sodium hydroxide (4500 mL, 5 mol/L) was added dropwise with stirring at 5° C. The reaction mixture was stirred for 0.5 h at room temperature. Then the pH of the mixture was adjusted to pH 5 with hydrogen chloride (5 mol/L) at 5° C. The resulting solids were collected by filtration. Into a 20 L 4-necked round-bottom flask, purged and maintained with an inert atmosphere of nitrogen, were placed the solids, ethanol (6000 mL), and tetrahydrofuran (1500 mL). Then sodium hydroxide (2000 mL, 5 mol/L) was added dropwise with stirring at 5° C. The resulting mixture was stirred for 3 h at 60° C., then concentrated under vacuum. The reaction mixture was cooled to 5° C. with a water/ice bath, and the pH of the mixture was adjusted to pH 5 with HCl (5 mol/L). The resulting solids were collected by filtration and purified by re-crystallization from ether to afford the title compound.

Step C: 2-chloro-5-[3-(methoxymethoxy)-1,2-oxazol-5-yl]pyridine. Into a 20 L 4-necked round-bottom flask, purged and maintained with an inert atmosphere of nitrogen, was placed a solution of 5-(6-chloropyridin-3-yl)-1,2-oxazol-3-ol (560 g, 2.85 mol) in tetrahydrofuran (5000 mL) and triethylamine (862.4 g, 8.52 mol, 3.00 eq). Then bromo (methoxy)methane (531.6 g, 4.25 mol) was added dropwise with stirring at 0° C., and the reaction mixture was stirred for 0.5 h at room temperature. The reaction was then quenched by the addition of 5000 mL of sodium bicarbonate, and the resulting mixture was extracted with 2×2000 mL of ethyl acetate. The combined organic layers were dried over anhydrous sodium sulfate and concentrated under vacuum. The resulting residue was purified via silica gel chromatography eluting with ethyl acetate/petroleum ether (1:20-1:10) to afford the title compound. $^1$H NMR (300 MHz, CDCl$_3$) δ 3.58 (3H, s), 5.38 (2H, s), 6.33 (1H, s), 7.43-7.46 (1H, d), 7.98-8.01 (1H, d), 8.74-8.75 (1H, s). LC-MS (ES, m/z): 241 [M+H]$^+$.

Intermediate 7

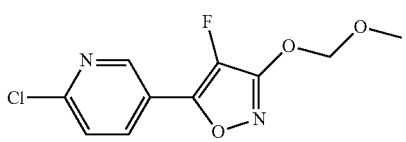

2-chloro-5-[4-fluoro-3-(methoxymethoxy)isoxazol-5-yl]pyridine

Into a 5000-mL 4-necked round-bottom flask, purged and maintained with an inert atmosphere of nitrogen, was placed tetrahydrofuran (1000 mL), and LDA (750 mL, 2 M in THF), followed by the dropwise addition of a solution of 2-chloro-5-[3-(methoxymethoxy)-1,2-oxazol-5-yl]pyridine (300 g, 1.25 mol) in tetrahydrofuran (1000 mL) with stirring at −78° C. The reaction mixture was stirred for 1.5 h at −65° C., then a solution of N-(benzenesulfonyl)-S-phenylfluorane-sulfonamido (472.5 g, 1.50 mol) in tetrahydrofuran (1000 mL) was added dropwise with stirring at −78° C. The mixture was stirred for an additional 0.5 h at room temperature, then quenched by the addition of 1000 mL of NH$_4$Cl. The resulting solution was diluted with 3000 mL of H$_2$O, and extracted with 3×1000 mL of ethyl acetate. The combined organic layers were dried over anhydrous sodium sulfate and concentrated under vacuum. The resulting residue was purified on a silica gel column eluting with ethyl acetate/petroleum ether (1:50-1:10) to afford the title compound. $^1$H NMR (300 MHz, DMSO-d$_6$) δ 3.52 (3H, s), 5.47 (2H, s), 7.75-7.78 (1H, d), 8.17-8.21 (1H, d), 8.80 (1H, s). LC-MS (ES, m/z): 259 [M+H]$^+$.

Intermediate 8

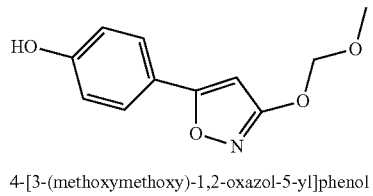

4-[3-(methoxymethoxy)-1,2-oxazol-5-yl]phenol

Step A: 1-(benzyloxy)-4-iodobenzene. Into a 5-L 4-necked round-bottom flask, purged and maintained with an inert atmosphere of nitrogen, was placed 4-iodophenol (300 g, 1.36 mol), N,N-dimethylformamide (3 L), and potassium carbonate (565 g, 4.09 mol), followed by the dropwise addition of (bromomethyl)benzene (232 g, 1.36 mol). The reaction was stirred overnight at room temperature, then the solids were filtered out. The filtrate was diluted with 500 mL of H$_2$O, and the mixture was extracted with 2×1000 mL of ethyl acetate. The combined organic layers were concentrated under vacuum. The resulting residue was purified on a silica gel column eluting with ethyl acetate/petroleum ether (1:10) to afford the title compound.

Step B: ethyl 3-[4-(benzyloxy)phenyl]prop-2-ynoate. Into a 5-L 4-necked round-bottom flask, purged and maintained with an inert atmosphere of nitrogen, was placed 1-(benzyloxy)-4-iodobenzene (228 g, 735.17 mmol), N,N-dimethylformamide (2300 mL) and Cu$_2$O (106 g, 740.79 mmol), followed by the dropwise addition of ethyl prop-2-ynoate (144 g, 1.47 mol). The reaction was stirred overnight at 110° C. and then cooled to room temperature. The resulting solids were filtered off. The filtrate was diluted with 500 mL of H$_2$O, and extracted with 2×1000 mL of ethyl acetate. The combined organic layers were concentrated under vacuum. The resulting residue was purified on a silica gel column eluting with ethyl acetate/petroleum ether (1:5) to afford the title compound.

Step C: 5-[4-(benzyloxy)phenyl]-1,2-oxazol-3-ol. Into a 3-L 4-necked round-bottom flask, purged and maintained with an inert atmosphere of nitrogen, was placed ethyl 3-[4-(benzyloxy)-phenyl]prop-2-ynoate (125 g, 445.92 mmol), methanol (1200 mL) and hydroxylamine hydrochloride (123 g, 1.77 mol). Then a solution of potassium hydroxide (150 g, 2.68 mol) in methanol (535 mL) was added dropwise. The resulting solution was stirred overnight at room temperature, then concentrated under vacuum and diluted with 500 mL of H$_2$O. The pH value of the solution was adjusted to pH 2 with HCl (2 mol/L), and the resulting solids were collected by filtration to afford the title compound.

Step D: 5-[4-(benzyloxy)phenyl]-3-(methoxymethoxy)-1,2-oxazole. Into a 3-L 4-necked round-bottom flask, purged and maintained with an inert atmosphere of nitrogen, was placed 5-[4-(benzyloxy)phenyl]-1,2-oxazol-3-ol (75 g, 280.61 mmol), tetrahydrofuran (1500 mL) and TEA (85 g, 840.00 mmol), followed by the dropwise addition of bromo (methoxy)methane (70 g, 560.16 mmol) at 0° C. The reaction was stirred for 30 min at 0° C., then diluted with 500 mL of H$_2$O, and extracted with 2×250 mL of ethyl acetate. The combined organic layers were concentrated under vacuum. The resulting residue was purified on a silica gel column eluting with ethyl acetate/petroleum ether (1:10) to afford the title compound.

Step E: 4-[3-(methoxymethoxy)-1,2-oxazol-5-yl]phenol. Into a 1-L round-bottom flask purged and maintained with an inert atmosphere of nitrogen, was placed 5-[4-(benzyloxy)-phenyl]-3-(methoxymethoxy)-1,2-oxazole (45 g, 144.54 mmol), methanol (500 mL) and Pd(OH)$_2$/C (4.5 g). The reaction was stirred for 4 h under a hydrogen balloon at room temperature. Then the solids were filtered off and the filtrate was concentrated under vacuum to afford the title compound. $^1$H NMR (300 MHz, CDCl$_3$) δ 3.52 (3H, s), 5.35 (2H, s), 5.91 (1H, br), 6.11 (1H, s), 6.94 (2H, d), 7.61 (2H, d). LC-MS (ES, m/z): 222 [M+H]$^+$.

Example 1

5-[5-({cis-3-[4-(difluoromethyl)-3-fluorophenyl] cyclobutyl}oxy)pyrazin-2-yl]isoxazol-3-ol

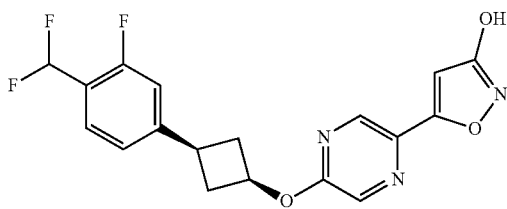 [SMILES: Oc1cc(-c2cnc(O[C@H]3C[C@@H](c4ccc(C(F)F)c(F)c4)C3)cn2)on1]

Step A: 1-(difluoromethyl)-2-fluoro-4-vinylbenzene. In 100 mL high pressure vessel was added 4-bromo-1-(difluoromethyl)-2-fluorobenzene (13.15 g, 58.4 mmol), sodium carbonate (12.39 g, 117 mmol), potassium trifluoro(vinyl) borate (7.83 g, 58.4 mmol) and dioxane. The reaction was purged with N$_2$ for 10 min, followed by the addition of [1,1'-Bis(diphenylphosphino)ferrocene]-dichloropalladium (II) (4.28 g, 5.84 mmol) and water. The reaction was sealed with a screw cap and heated to 100° C. overnight, then cooled to room temperature and filtered. The filtrate was concentrated to give a solid. Then hexanes was added and the mixture was filtered through a silica gel pad and washed 3 times with hexanes. The filtrate was concentrated to give the desired product, which is used in the next step without further purification.

Step B: 2,2-dichloro-3-(4-(difluoromethyl)-3-fluorophenyl)cyclobutanone. To a suspension of activated Zn-Cu dust in ether was added a chip of iodine. The reaction mixture was stirred for 10 min until the color of the iodine disappeared. Then a solution of 1-(difluoromethyl)-2-fluoro-4-vinylbenzene (Step A, 10.05 g, 58.4 mmol) in ether was added, followed by the addition of a mixture of phosphoryl trichloride (8.95 g, 58.4 mmol) and 2,2,2-trichloroacetyl chloride (10.62 g, 58.4 mmol) in ether. The reaction was purged with N$_2$, stirred at rt overnight, and then poured into water. Ethyl acetate was added, and the resulting organic layer was washed with water. The combined aqueous layers were extracted with EtOAc, washed with saturated aq. NaHCO$_3$, dried over Na$_2$SO$_4$ and concentrated under vacuum to give the title compound, which was taken on to the next step without further purification.

Step C: 3-(4-(difluoromethyl)-3-fluorophenyl)cyclobutanone. 2,2-dichloro-3-(4-(difluoro-methyl)-3-fluorophenyl)cyclobutanone (Step B) was dissolved in AcOH (15 mL) and zinc dust (15.27 g, 234 mmol) was added in one portion. The reaction was kept at 80° C. for 1 h, then cooled to room temperature and stirred overnight. Then the reaction mixture was poured into water and EtOAc was added. The aqueous layer was extracted with EtOAc. The combined organic layers were washed with aqueous NaHCO$_3$, dried over Na$_2$SO$_4$ and concentrated to give the title compound, which was used in the next step without further purification.

Step D: Cis-3-(4-(difluoromethyl)-3-fluorophenyl)cyclobutanol. 3-(4-(difluoromethyl)-3-fluoro-phenyl)cyclobutanone (Step C) was dissolved in MeOH and cooled to 0° C., and NaBH$_4$ was added slowly. Then the cooling bath was removed, and the reaction was stirred at room temperature for 1 h. The reaction mixture was carefully treated with HCl in dioxane (4.0 M, 3 mL), followed by filtration. The filtrate was concentrated, and the resulting residue was purified by normal phase column chromatography (SiO$_2$) using 20% of EtOAc in hexanes to give the title compound.

Step E: 5-(5-(cis-3-(4-(difluoromethyl)-3-fluorophenyl) cyclobutoxy)pyrazin-2-yl)-3 (methoxymethoxy)isoxazole. A solution of cis-3-(4-(difluoromethyl)-3-fluorophenyl)-cyclobutanol (Step D, 1.272 g, 5.88 mmol) in THF was purged with N$_2$ for 5 min, then NaHMDS (1.0 M in THF, 6.17 mL) was added at room temperature. After stirring for 10 min, a solution of 5-(5-bromopyrazin-2-yl)-3-(methoxymethoxy) isoxazole (1.683 g, 5.88 mmol) in THF was added and the reaction was stirred at room temperature overnight. The reaction was quenched by the addition of pH 7 buffer. Then the solvent was removed and the resulting residue was purified by normal phase column chromatography (SiO$_2$) using 20% EtOAc in hexanes to give the title compound.

Step F: 5-(5-(cis-3-(4-(difluoromethyl)-3-fluorophenyl) cyclobutoxy)pyrazin-2-yl)isoxazol-3-ol. 5-(5-(cis-3-(4-(difluoromethyl)-3-fluorophenyl)cyclobutoxy)pyrazin-2-yl)-3-(methoxymethoxy)isoxazole was dissolved in 1,4-dioxane and treated with HCl in 1,4-dioxane (4.0 M, 1.47 mL) and 1 mL of water. The reaction was stirred at 60° C. for 1 h, then the solvent was removed and the resulting solid was suspended in EA and treated with 50 mL of saturated aqueous NH$_4$Cl. The aqueous layer was extracted with 10% of IPA in EtOAc (5×). The combined organic layers were dried over Na$_2$SO$_4$ and concentrated to give the title compound. $^1$H NMR (500 MHz, CD$_3$OD) δ 2.35-2.28 (2H, m), 3.07-3.01 (2H, m), 3.34 (1H, m), 5.38-5.32 (1H, m), 6.45 (1H, s), 6.97 (1H, t, $^2J_{H-F}$=54.9 Hz), 7.19 (1H, d, J=11.6 Hz), 7.26 (1H, d, J=8.0 Hz), 7.57 (1H, t, J=7.7 Hz), 8.29 (1H, d, J=1.4 Hz), 8.63 (1H, d, J=1.4 Hz). MS (ES m/z) 378 [M+H]$^+$.

Example 1

Alternative Synthesis

5-[5-({cis-3-[4-(difluoromethyl)-3-fluorophenyl] cyclobutyl}oxy)pyrazin-2-yl]isoxazol-3-ol

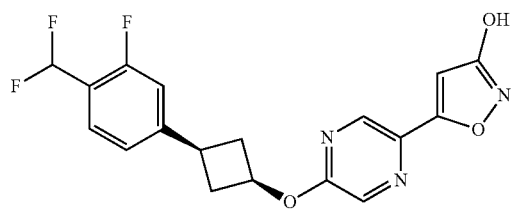 [SMILES: Oc1cc(-c2cnc(O[C@H]3C[C@@H](c4ccc(C(F)F)c(F)c4)C3)cn2)on1]

Step A: 4-bromo-1-(difluoromethyl)-2-fluorobenzene. To a solution of 4-bromo-2-fluoro-benzaldehyde (100 g, 493 mmol) in DCM (1000 mL) was added DAST (159 g, 985 mmol) at 0° C., and the resulting mixture was stirred at 25° C. for 2 h. Then the reaction mixture was poured into ice-water (600 mL) and extracted with DCM (3×300 mL). The combined organic layers were washed with brine (400 mL), dried over Na$_2$SO$_4$, and filtered. The filtrate was concentrated, and the resulting residue was purified using column chromatography (SiO$_2$, PE) to give the title compound.

Step B: 1-(difluoromethyl)-2-fluoro-4-vinylbenzene. To a solution of 4-bromo-1-(difluoro-methyl)-2-fluorobenzene (47.5 g, 211 mmol), potassium trifluoro(vinyl)borate (33.9 g, 253 mmol), and Et$_3$N (88 ml, 633 mmol) in EtOH (500 mL) was added PdCl$_2$(dppf) (7.72 g, 10.56 mmol) under a N$_2$ atmosphere. The resulting mixture was stirred at 80° C. under N$_2$ for 10 h.

Then the reaction mixture was poured into water (1000 mL), filtered and extracted with pentane (3×500 mL). The combined organic layers were washed with water (100 mL) and brine (100 mL), dried over Na$_2$SO$_4$, and filtered. The filtrate was concentrated (below 30° C.), and the resulting residue was purified using column chromatography (SiO$_2$, PE) to give the title compound.

Step C: 2,2-dichloro-3-(4-(difluoromethyl)-3-fluorophenyl)cyclobutanone. To a solution of 1-(difluoromethyl)-2-fluoro-4-vinylbenzene (36 g, 209 mmol) in ether (1500 ml) was added diacetoxycopper (3.80 g, 20.91 mmol) and zinc (27.3 g, 418 mmol). The mixture was stirred at 18-25° C. for 30 minutes, then 2,2,2-trichloroacetyl chloride (76 g, 418 mmol) was added in portions at 40° C. under N$_2$. The reaction mixture was filtered and concentrated to 200 ml, before it was quenched with H$_2$O (100 mL) and extracted with EA (3×300 mL). The combined organic layers were washed with brine (200 mL), dried over Na$_2$SO$_4$, and filtered. The filtrate was concentrated to afford the title compound, which was used in the next step without further purification.

Step D: 3-(4-(difluoromethyl)-3-fluorophenyl)cyclobutanone. To a solution of 2,2-dichloro-3-(4-(difluoromethyl)-3-fluorophenyl)cyclobutanone (40 g, 141 mmol) in MeOH (500 ml) was added NH$_4$Cl (76 g, 1413 mmol) and zinc (46.2 g, 707 mmol) in portions at 0° C. The reaction mixture was stirred at 18-25° C. for 10 h, then filtered, concentrated, quenched with water (50 mL) and extracted with EA (3×100 mL). The combined organic layers were washed with brine (100 mL), dried over Na$_2$SO$_4$, and filtered. The filtrate was concentrated, and the resulting residue was purified by column chromatography (SiO$_2$, PE:EA=5:1) to afford the title compound.

Step E: cis-3-[4-(difluoromethyl)-3-fluorophenyl]cyclobutanol. To a solution of 3-(4-(difluoromethyl)-3-fluorophenyl)cyclobutanone (30 g, 140 mmol) in THF (400 ml) was added LAH (6.38 g, 168 mmol) in portions at 0° C. The reaction mixture was stirred at 0° C. for 2 h, then H$_2$O (8 ml) was added slowly to quench the reaction. The reaction mixture was filtered, and the organic phase was separated, dried over Na$_2$SO$_4$, and filtered. The filtrate was concentrated to afford the title compound, which was used in the next step without further purification.

Step F: 2-({cis-3-[4-(difluoromethyl)-3-fluorophenyl]cyclobutyl}oxy)-5-[3-(methoxymethoxy)-isoxazol-5-yl]pyrazine. To a solution of cis-3-[4-(difluoromethyl)-3-fluorophenyl] cyclobutanol (13 g, 60.1 mmol) and 5-(5-bromopyrazin-2-yl)-3-(methoxymethoxy)isoxazole (20.64 g, 72.2 mmol) in THF (300 mL) was added a solution of sodium 2-methylpropan-2-olate (11.56 g, 120 mmol). The reaction was stirred at 40° C. for 3 h, then diluted with H$_2$O (200 ml) and extracted with EA (3×300 mL). The combined organic layers were washed with brine (200 mL), dried over Na$_2$SO$_4$, and filtered. The filtrate was concentrated to afford the title compound, which was used in the next step without further purification. MS (ESI) m/z: 422 [M+H]$^+$.

Step G: 5-[5-({cis-3-[4-(difluoromethyl)-3-fluorophenyl]cyclobutyl}oxy)pyrazin-2-yl]-isoxazol-3-ol. The mixture of 2-({cis-3-[4-(difluoromethyl)-3-fluorophenyl]cyclobutyl}oxy)-5-[3-(methoxymethoxy)isoxazol-5-yl]pyrazine (35 g, 83 mmol) in THF (500 mL) was adjusted to pH 3-4 with HCl (13.84 mL, 41.5 mmol). The resulting mixture was stirred at 40° C. for 1.5 h, then poured into aqueous NH$_4$Cl (300 mL), and extracted with EtOAc (3×300 mL). The combined organic layers were washed with brine (300 mL), dried over MgSO$_4$, and filtered. The filtrate was concentrated, and the resulting residue was suspended in MeOH (100 mL) and stirred for 20 min. The mixture was filtered and the solid was dried in vacuo to give the title compound. $^1$H-NMR (400 MHz, DMSO-d$_6$) δ 8.69 (s, 1H), 8.39 (s, 1H), 7.56 (t, J=7.72 Hz, 1H), 7.00-7.33 (m, 3H), 6.52 (s, 1H), 5.22 (q, J=7.33 Hz, 1H), 3.24-3.31 (m, 1H), 2.87-2.97 (m, 2H), 2.18-2.30 (m, 2H). MS m/z 378 [M+H]$^+$.

Example 2

5-[5-({trans-3-[4-(difluoromethyl)-3-fluorophenyl]cyclobutyl}oxy)pyrazin-2-yl]isoxazol-3-ol

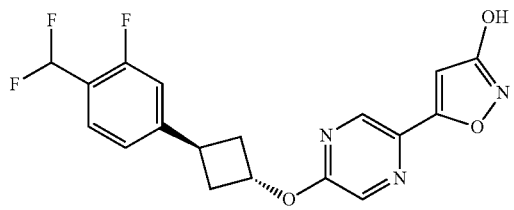 [SMILES: Oc1cc(-c2cnc(O[C@H]3C[C@H](c4ccc(C(F)F)c(F)c4)C3)cn2)on1]

Step A: trans-3-[4-(difluoromethyl)-3-fluorophenyl]cyclobutyl benzoate. To a solution of cis-3-[4-(difluoromethyl)-3-fluorophenyl]cyclobutanol (900 mg, 4.16 mmol), triphenylphosphine (1638 mg, 6.24 mmol) and benzoic acid (763 mg, 6.24 mmol) in anhydrous THF (30 mL) was added dropwise DEAD (0.989 ml, 6.24 mmol) at 0° C. The reaction mixture was stirred at 18-25° C. under N$_2$ for 10 h, then poured into water (30 mL) and extracted with EA (3×40 mL). The combined organic layers were washed with brine (3×10 mL), dried over Na$_2$SO$_4$, and filtered. The filtrate was concentrated, and the resulting residue was purified by column chromatography (SiO$_2$, PE:EA=10:1) to give the title compound.

Step B: trans-3-[4-(difluoromethyl)-3-fluorophenyl]cyclobutanol. To a solution of trans-3-[4-(difluoromethyl)-3-fluorophenyl]cyclobutyl benzoate (700 mg, 2.185 mmol) in MeOH (10 mL) and water (2 mL) was added K$_2$CO$_3$ (453 mg, 3.28 mmol). The resulting mixture was stirred at 70° C. for 2 h, then poured into water (10 mL) and extracted with EA (3×40 mL). The combined organic layers were washed with brine (3×10 mL), dried over Na$_2$SO$_4$, and filtered. The filtrate was concentrated, and the resulting residue was purified by column chromatography (SiO$_2$, PE:EA=10:1) to give the title compound.

Step C: 2-({trans-3-[4-(difluoromethyl)-3-fluorophenyl]cyclobutyl}oxy)-5-[3-(methoxy-methoxy)isoxazol-5-yl]pyrazine. To a solution of trans-3-[4-(difluoromethyl)-3-fluoro-phenyl]cyclobutanol (400 mg, 1.850 mmol) and 5-(5-bromopyrazin-2-yl)-3-(methoxy-methoxy)isoxazole (423 mg, 1.480 mmol) in THF (20 mL) was added a solution of sodium 2-methylpropan-2-olate (356 mg, 3.70 mmol). The reaction mixture was stirred at 40° C. for 3 h. Then the mixture was diluted with H$_2$O (20 mL) and extracted with EA (3×30 mL). The combined organic layers were washed with brine (30 mL), dried over Na$_2$SO$_4$, and filtered. The filtrate was concentrated to give the title compound, which was used in the next step without purification. MS (ESI) m/z: 422 [M+H]$^+$.

Step D: 5-[5-({trans-3-[4-(difluoromethyl)-3-fluorophenyl]cyclobutyl}oxy)-pyrazin-2-yl]-isoxazol-3-ol. A mixture of 2-({trans-3-[4-(difluoromethyl)-3-fluorophenyl]cyclobutyl}-oxy)-5-[3-(methoxymethoxy)isoxazol-5-yl]pyrazine (200 mg, 0.475 mmol) in THF (15 mL) was adjusted to pH 3-4 with HCl (3M, 0.079 mL, 0.237 mmol). The mixture was stirred at 40° C. for 1.5 h. The resulting mixture was poured into H$_2$O (20 mL), and extracted with EtOAc (3×30 mL). The combined organic layers were washed with brine (300 mL), dried over MgSO$_4$, and filtered. The filtrate was concentrated, and the resulting residue was suspended in MeOH (100 mL) and stirred for 20 min. Then the suspension was filtered and the solid was dried in vacuo to give the title compound. $^1$H-NMR (400 MHz, DMSO-d$_6$) δ 8.67 (s, 1H), 8.44 (s, 1H), 7.58 (t, J=7.72 Hz, 1H), 7.36 (d, J=11.91 Hz, 1H), 7.31 (m, 1H), 7.02-7.30 (m, 1H), 6.52 (s, 1H), 5.41 (t, J=5.73 Hz, 1H), 3.79 (t, J=7.72 Hz, 1H), 2.64 (t, J=6.84 Hz, 5H). MS (ESI) m/z: 378 [M+H]$^+$.

Example 3 ammonium 5-[5-({cis-3-[3-fluoro-5-(trifluoromethoxy)-phenyl]cyclobutyl}oxy)pyrazin-2-1]isoxazol-3-olate

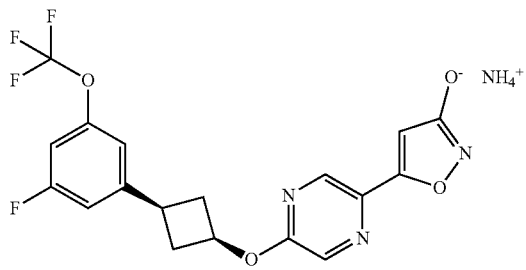 [SMILES: [O-]c1cc(-c2cnc(O[C@H]3C[C@@H](c4cc(F)cc(OC(F)(F)F)c4)C3)cn2)on1 ; [NH4+]]

Step A: 1-fluoro-3-(trifluoromethoxy)-5-vinylbenzene. To a solution of 3-fluoro-5-(trifluoromethoxy)benzaldehyde (13.6 g, 65.4 mmol) and methyltriphenylphosphonium bromide (28.0 g, 78 mmol) in THF (200 mL) was added in portions sodium 2-methyl-propan-2-olate (28.3 g, 294 mmol) at 0° C. The resultant mixture was stirred at ambient temperature for 12 h, then quenched with H$_2$O (20 mL) and extracted with EA (3×30 mL). The combined organic layers were washed with brine (20 mL), dried over Na$_2$SO$_4$, and filtered. The filtrate was concentrated, and the residue was purified by column chromatography (SiO$_2$ eluting with PE:EA=10:1) to give the title compound.

Step B: 2,2-dichloro-3-(3-fluoro-5-(trifluoromethoxy)phenyl)cyclobutanone. To a mixture of 1-fluoro-3-(trifluoromethoxy)-5-vinylbenzene (4 g, 19.40 mmol) and activated Zn-Cu (2.75 g, 21.35 mmol) in Et$_2$O (40 mL) was added dropwise a solution of 2,2,2-trichloro acetylchloride (7.06 g, 38.8 mmol) in Et$_2$O (10 mL) at 40° C. The resultant mixture was stirred at 40° C. for 12 h, then quenched with H$_2$O (30 mL) and extracted with EA (3×30 mL). The combined organic layers were washed with brine (50 mL), dried over Na$_2$SO$_4$, and filtered. The filtrate was concentrated to afford the title compound, which was used in the next step without further purification.

Step C: 3-(3-fluoro-5-(trifluoromethoxy)phenyl)cyclobutanone. To a solution of 2,2-dichloro-3-(3-fluoromethoxy)phenyl)cyclobutanone (2 g, 6.31 mmol) and NH$_4$Cl (3.37 g, 63.1 mmol) in methanol (30 mL) was added Zn (2.062 g, 31.5 mmol) in portions at 0° C. The resultant mixture was stirred at ambient temperature for 5 h. Then the mixture was filtered and the filtrate was concentrated under reduced pressure. The resulting residue was diluted with water (30 mL) and extracted with EA (3×30 mL). The combined organic layers were washed with brine (20 mL), dried over Na$_2$SO$_4$, and filtered. The filtrate was concentrated, and the resulting residue was purified by normal phase column chromatography (SiO$_2$ eluting with PE:EA=10:1) to afford the title compound.

Step D: cis-3-[3-fluoro-5-(trifluoromethoxy)phenyl]cyclobutanol. To a solution of 3-(3-fluoro-5-(trifluoromethoxy)phenyl)cyclobutanone (430 mg, 1.733 mmol) in THF (20 mL) was added LAH (79 mg, 2.08 mmol) at 0° C. in portions. The resultant mixture was stirred at 0° C. for 2 h. Then H$_2$O (0.5 mL) and aqueous sodium hydroxide (0.5 mL) were added, the mixture was diluted with EA (10 mL) and then filtered. The filtrate was concentrated to give the title compound, which was used in the next step without further purification.

Step E: 2-({cis-3-[3-fluoro-5-(trifluoromethoxy)phenyl]cyclobutyl}oxy)-5-[3-(methoxy-methoxy)isoxazol-5-yl]pyrazine. To a solution of cis-3-[3-fluoro-5-(trifluoromethoxy)-phenyl]cyclobutanol (131 mg, 0.524 mmol) and 5-(5-bromopyrazin-2-yl)-3-(methoxymethoxy)-isoxazole (100 mg, 0.350 mmol) in THF (20 mL) was added a solution of sodium 2-methylpropan-2-olate (101 mg, 1.049 mmol). The resultant mixture was stirred at 40° C. for 4 h, then quenched with H$_2$O (20 mL) and extracted with EA (3×30 mL). The combined organic layers were washed with brine (20 mL), dried over Na$_2$SO$_4$ and filtered. The filtrate was concentrated to afford the title compound, which was used in the next step without further purification.

Step F: Ammonium 5-[5-({cis-3-[3-fluoro-5-(trifluoromethoxy)phenyl]cyclobutyl}-oxy)-pyrazin-2-yl]isoxazol-3-olate. To a solution of 2-({cis-3-[3-fluoro-5-(trifluoromethoxy)-phenyl]cyclobutyl}oxy)-5-[3-(methoxymethoxy)isoxazol-5-yl]pyrazine (98 mg, 0.215 mmol) in THF (20 mL) was added 3 M aqueous HCl (1 mL). The resultant mixture was stirred at 40° C. for 4 h, then quenched with H$_2$O (20 mL) and extracted with EA (3×30 ml). The combined organic layers were washed with brine (30 mL), dried over Na$_2$SO$_4$ and filtered. The filtrate was concentrated, and the resulting residue was purified by prep-HPLC (NH$_3$OH modifier) to give to give the title compound. $^1$H NMR (400 MHz, DMSO-d$_6$) δ 8.62 (brs, 1H), 8.35 (s, 1H), 7.24 (d, J=9.39 Hz, 1H), 7.18 (d, J=7.04 Hz, 1H), 7.12 (br. s., 1H), 6.41 (br. s., 1H), 5.18 (t, J=7.04 Hz, 1H), 2.89 (d, J=7.04 Hz, 2H), 2.61 (br. s., 1H), 2.21 (d, J=8.61 Hz, 2H). MS(ESI) m/z: 412.0 [M+H]$^+$.

Example 4 sodium 5-[5-({cis-3-[4-(cyclopropyloxy)phenyl]cyclobutyl}-oxy)pyrazin-2-yl]isoxazol-3-olate

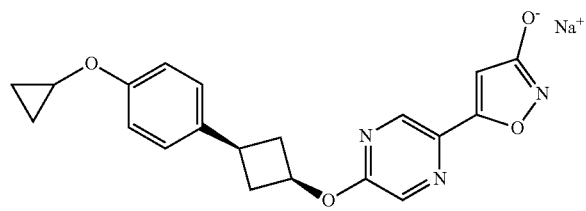 [SMILES: [O-]c1cc(-c2cnc(O[C@H]3C[C@@H](c4ccc(OC5CC5)cc4)C3)cn2)on1 ; [Na+]]

Step A: 1-bromo-4-(vinyloxy)benzene. To a solution of 4-bromophenol (100 g, 0.578 mol) in toluene (500 mL) was added vinyl acetate (107 mL, 1.156 mol), $Na_2CO_3$ (49 g, 0.462 mol) and $[Ir(cod)]Cl_2$ (1.94 g, 2.89 mmol) at 18° C. The reaction was stirred at 100° C. under a $N_2$ atmosphere for 12 h. Then the mixture was filtered, and the filtrate was concentrated to give a residue, which was purified by column chromatography over silica gel (PE) to give the title compound.

Step B: 1-bromo-4-cyclopropoxybenzene. To a solution of 1-bromo-4-(vinyloxy)benzene (75 g, 0.376 mol) in DCM (800 mL) was added $CH_2ICl$ (264.7 g, 1.504 mol) at 18° C. Then $Et_2Zn$ (750 mL, 1M in toluene) was added slowly at 0° C. under $N_2$. The reaction was warmed to 18° C. and stirred for 12 h under $N_2$. Then the reaction mixture was added slowly to aqueous $NH_4Cl$ (500 mL), extracted with PE (3×800 mL), dried over $Na_2SO_4$ and filtered. The filtrate was concentrated, and the resulting residue was purified by column chromatography over silica gel (PE) to afford the title compound.

Step C: 1-cyclopropoxy-4-vinylbenzene. To a solution of 1-bromo-4-cyclopropoxybenzene (60 g, 0.281 mol) in EtOH (600 mL) were added potassium trifluoro(vinyl)borate (56.4 g, 0.421 mmol), $Pd(dppf)Cl_2$ (10.3 g, 0.014 mol) and $Et_3N$ (56.8 g, 0.56 mol) under $N_2$ atmosphere. The reaction mixture was stirred at 80° C. for 12 h under $N_2$, then filtered and concentrated to give a residue, which was purified by column chromatography over silica gel (PE) to afford the title compound.

Step D: 2,2-dichloro-3-(4-cyclopropoxyphenyl)cyclobutanone. To a solution of 1-cyclo-propoxy-4-vinylbenzene (76 g, 0.47 mol) in diethyl ether (1500 mL) was added Zn (61 g, 0.94 mol) and copper acetate (8.5 g, 0.047 mol). The reaction was stirred at 18° C. for 30 min under $N_2$, then warmed to 40° C. and a solution of trichloroacetyl chloride (170 g, 0.94 mol) in ethyl ether (100 mL) was added slowly into the mixture. The reaction was cooled to 25° C. and stirred for 12 h under $N_2$. Then the reaction mixture was filtered, poured into water (400 mL), extracted with EA (3×400 mL) and dried over $Na_2SO_4$. The mixture was filtered and the filtrate was concentrated to give a residue, which was purified by column chromatography over silica gel (PE:EA=5:1) to give the title compound.

Step E: 3-(4-cyclopropoxyphenyl)cyclobutanone. To a solution of 2,2-dichloro-3-(4-cyclo-propoxyphenyl)cyclobutanone (100 g, 0.369 mol) and $NH_4Cl$ (195.6 g, 3.69 mol) in MeOH (1000 mL) was added slowly Zn (119.9 g, 1.845 mol) at 0° C. Then the resulting mixture was stirred at 18° C. for 12 h. The mixture was filtered, washed with EA and concentrated in vacuo. Then the mixture was poured into water (200 mL), extracted with EA (3×200 mL) and dried over $Na_2SO_4$. After filtration and concentration, the residue was purified by column chromatography over silica gel (PE:EA=10:1) to afford the title compound. $^1H$ NMR (400 MHz, $CDCl_3$) δ 7.20 (d, J=8.61 Hz, 2H), 7.02 (d, J=8.61 Hz, 2H), 3.67-3.75 (m, 1H), 3.56-3.66 (m, 1H), 3.37-3.53 (m, 2H), 3.12-3.26 (m, 2H), 0.72-0.78 (m, 4H).

Step F: cis-3-[4-(cyclopropyloxy)phenyl]cyclobutanol. To a solution of 3-(4-cyclopropoxy-phenyl)cyclobutanone (8 g, 39.6 mmol) in THF (100 mL) was added slowly LAH (1.96 g, 51.5 mmol) at 0° C. The resulting mixture was stirred at 0° C. for 1 h, then diluted with water (5 mL). The mixture was filtered and dried over $Na_2SO_4$, and filtered. The filtrate was concentrated afforded the title compound, which was used directly in the next step without additional purification.

Step G: 2-({cis-3-[4-(cyclopropyloxy)phenyl]cyclobutyl}oxy)-5-[3-(methoxymethoxy)-isoxazol-5-yl]pyrazine. To a solution of cis-3-[4-(cyclopropyloxy)phenyl]cyclobutanol (8 g, 39.2 mmol) in THF (250 mL) was added 5-(5-bromopyrazin-2-yl)-3-(methoxymethoxy)-isoxazole (9.35 g, 32.67 mmol) and tBuONa (7.84 g, 81.7 mmol). Then the resulting mixture was stirred at 40° C. for 2 h. Then the mixture was poured into water (50 mL), extracted with EA (3×50 mL) and dried over $Na_2SO_4$. The mixture was filtered and the filtrate was concentrated under reduced pressure to give the title compound, which was used directly in the next step without further purification. MS (ESI) m/z: 410 $[M+H]^+$.

Step H: sodium 5-[5-({cis-3-[4-(cyclopropyloxy)phenyl]cyclobutyl}oxy)pyrazin-2-yl]-isoxazol-3-olate. To a solution of 2-({cis-3-[4-(cyclopropyloxy)phenyl]cyclobutyl}oxy)-5-[3-(methoxymethoxy)isoxazol-5-yl]pyrazine (11 g, 26.9 mmol) in THF (250 mL) was added 3 N aqueous HCl (4 mL) to adjust the pH to 2-3. The mixture was stirred at 40° C. for 2 h, then poured into water (30 mL), extracted with EA (3×50 mL), dried over $Na_2SO_4$, and filtered. The filtrate was concentrated under vacuum. The resulting residue was added to MeOH (20 mL) and stirred at 15° C. for 1 h. Then the mixture was filtered and the filter cake was suspended in MeCN (500 mL). Then aqueous NaOH (49.8 mL, 1 g/50 mL water) was added dropwise to the suspension, which was freeze dried to afford the title compound. $^1H$-NMR (400 MHz, $CD_3OD$) δ 8.49 (s, 1H), 8.20 (s, 1H), 7.14-7.21 (m, 2H), 6.92-7.01 (m, 2H), 6.17 (s, 1H), 5.17-5.31 (m, 1H), 3.73 (m, 1H), 3.07-3.24 (m, 1H), 2.85-3.00 (m, 2H), 2.12-2.29 (m, 2H), 0.70-0.83 (m, 2H), 0.59-0.69 (m, 2H). MS(ESI) m/z: 366.1 $[M+H]^+$.

Example 5

5-[5-({cis-3-[4-(trifluoromethyl)-1,3-thiazol-2-yl]cyclobutyl}oxy)pyrazin-2-yl]isoxazol-3-ol

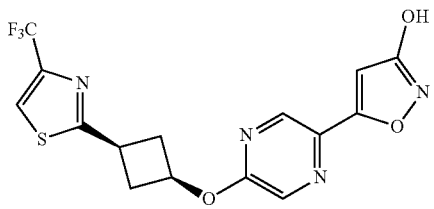 [SMILES: Oc1cc(-c2cnc(O[C@H]3C[C@@H](c4nc(C(F)(F)F)cs4)C3)cn2)on1]

Step A: 3-methylenecyclobutanecarbothioamide. To a solution of sodium hydrogen sulfide (45.2 g, 805 mmol) in anhydrous DMF (180 mL) and water (30 mL) was added ammonium chloride (43.1 g, 805 mmol) and 3-methylene cyclobutanecarbonitrile (15 g, 161 mmol). The resulting mixture was stirred at 40° C. under N₂ protection for 8 hours. Then the reaction mixture was filtered and washed with EA (200 mL). The organic layer was washed with water (5×80 mL), dried over Na₂SO₄, and filtered. The filtrate was concentrated, and the resulting residue was purified by column chromatography (SiO₂, PE:EA=20:1) to give the title compound.

Step B: 2-(3-methylenecyclobutyl)-4-(trifluoromethyl)-4,5-dihydrothiazol-4-ol. To a solution of 3-methylenecyclobutanecarbothioamide (1.27 g, 9.98 mmol) in anhydrous MeCN (20 mL) was added 3-bromo-1,1,1-trifluoropropan-2-one (1.906 g, 9.98 mmol). The resulting mixture was stirred at 80° C. under N₂ for 2 h, then concentrated to afford the title compound, which was used in the next step without additional purification. MS (ESI) m/z: 238.0 [M+H]⁺.

Step C: 2-(3-methylenecyclobutyl)-4-(trifluoromethyl)thiazole. A mixture of 2-(3-methylenecyclobutyl)-4-(trifluoromethyl)-4,5-dihydrothiazol-4-ol (900 mg, 3.79 mmol) and Et₃N (1.058 ml, 7.59 mmol) in DCM (20 mL) was cooled to 0° C., followed by the addition of TFAA (0.804 ml, 5.69 mmol). The reaction was stirred at 20° C. for 12 h, then poured into water (10 mL) and extracted with DCM (3×30 mL). The organic layer was separated, washed with brine (3×10 mL), dried over Na₂SO₄ and filtered. The filtrate was concentrated, and the resulting residue was purified by column chromatography (SiO₂, PE:EA=20:1) to give the title compound. MS (ESI) m/z: 220.0 [M+H]⁺.

Step D: 3-(4-(trifluoromethyl)thiazol-2-yl)cyclobutanone. Ozone was bubbled into a solution of 2-(3-methylenecyclobutyl)-4-(trifluoromethyl)thiazole (450 mg, 2.053 mmol) in DCM (30 mL) at −78° C. for 5 min. Then the ozone was purged by O₂, and Ph₃P (1077 mg, 4.11 mmol) was added at 20° C. The reaction was stirred for 1 h, then concentrated. The resulting residue was purified by column chromatography (SiO₂, PE:EA=10:1) to afford the title compound. MS (ESI) m/z: 222 [M+H]⁺.

Step E: cis-3-[4-(trifluoromethyl)-1,3-thiazol-2-yl]cyclobutanol. To a solution of 3-(4-(trifluoromethyl)thiazol-2-yl)cyclobutanone (150 mg, 0.678 mmol) in MeOH (6 ml) and DCM (3 ml) was added NaBH₄ (25.7 mg, 0.678 mmol) at 0° C. The mixture was stirred at 0° C. for 1 hour. Then the reaction mixture was poured into water (10 mL) and extracted with EA (3×30 mL). The organic layer was separated, washed with brine (3×10 mL), and dried over Na₂SO₄. After filtration and concentration, the residue was purified by column chromatography (SiO₂, PE:EA=4:1) to afford the title compound. ¹H NMR (400 MHz, CDCl₃) δ 7.64 (s, 1H), 4.33 (brs, 1H), 3.28-3.44 (m, 1H), 2.85-3.00 (m, 2H), 2.21-2.35 (m, 2H). MS (ESI) m/z: 224 [M+H]⁺.

Step F: 2-[3-(methoxymethoxy)isoxazol-5-yl]-5-({cis-3-[4-(trifluoromethyl)-1,3-thiazol-2-yl]-cyclobutyl}oxy)pyrazine. To a solution of 5-(5-bromopyrazin-2-yl)-3-(methoxymethoxy)-isoxazole (103 mg, 0.358 mmol) and cis-3-[4-(trifluoromethyl)-1,3-thiazol-2-yl]cyclobutanol (100 mg, 0.448 mmol) in anhydrous THF (10 mL) was added sodium 2-methylpropan-2-olate (86 mg, 0.896 mmol). The resulting mixture was stirred at 40° C. under N₂ protection for 12 hours, then poured into aq. NH₄Cl (20 mL), and extracted with EtOAc (3×20 mL). The combined organic layers were washed with brine (20 mL), dried over Na₂SO₄,and filtered. The filtrate was concentrated to afford the title compound. MS (ESI) m/z: 429.1 [M+H]⁺.

Step G: 5-[5-({cis-3-[4-(trifluoromethyl)-1,3-thiazol-2-yl]cyclobutyl}oxy)pyrazin-2-yl]-isoxazol-3-ol. To a solution of 2-[3-(methoxymethoxy)isoxazol-5-yl]-5-({cis-3-[4-(trifluoro-methyl)-1,3-thiazol-2-yl]cyclobutyl}oxy)pyrazine (100 mg, 0.233 mmol) in THF (10 ml) was added HCl (3M, 0.5 mL, 1.500 mmol). The resulting mixture was stirred at 40° C. for 5 hours, then concentrated. The resulting residue was washed with MeOH (5 mL), and filtered to give the title compound. ¹H NMR (400 MHz, DMSO-d₆) δ 8.60-8.78 (m, 1H), 8.40 (d, J=4.85 Hz, 2H), 6.52 (s, 1H), 5.17-5.42 (m, 1H), 3.63-3.81 (m, 1H), 2.91-3.09 (m, 2H), 2.37-2.45 (m, 2H). MS (ESI) m/z: 385 [M+H]⁺.

Example 6

5-[5-({cis-3-[5-(trifluoromethyl)-1,3-thiazol-2-yl]cyclobutyl}oxy)pyrazin-2-yl]isoxazol-3-ol

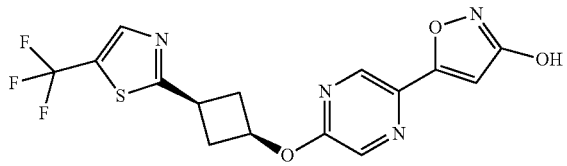 [SMILES: Oc1cc(-c2cnc(O[C@H]3C[C@@H](c4ncc(C(F)(F)F)s4)C3)cn2)on1]

Step A: 5-iodo-2-(3-methylenecyclobutyl)thiazole. Lithium diisopropylamide (4.30 mL, 8.60 mmol) was added to a solution of 2-(3-methylenecyclobutyl)thiazole (1.0 g, 6.61 mmol) in THF (25 mL) at −78° C., and then stirred for 1 h. To the mixture was added I₂ (1.846 g, 7.27 mmol) in THF (5 mL) and stirred for 1 h, The reaction mixture was quenched with water (30 mL), extracted with EA (3×20 mL). The organic layer was washed with water (30 ml), dried over Na₂SO₄. After filtration and concentration, the residue was purified by column (SiO₂, PE:EA=10:1) to give the title compound.

Step B: 3-(5-iodothiazol-2-yl)cyclobutanone. To a solution of ruthenium(III) chloride hydrate (21.96 mg, 0.097 mmol) and 5-iodo-2-(3-methylenecyclobutyl)thiazole (900 mg, 3.25 mmol) in DCM (6 mL), acetonitrile (6 mL) and water (9 mL) was added sodium periodate (2779 mg, 12.99 mmol) in portions at 0° C. The resulting mixture was stirred at 20° C. for 1 hour. Then the reaction mixture was poured into water (20 mL), filtered and extracted with DCM (3×15 mL). The organic layer was dried over Na₂SO₄. After filtration and concentration, the residue was purified by column chromatography (SiO₂, PE:EA=10:1) to afford the title compound.

Step C: 3-(5-(trifluoromethyl)thiazol-2-yl)cyclobutanone. Copper(I) iodide (512 mg, 2.69 mmol) was added to a mixture of methyl 2,2-difluoro-2-(fluorosulfonyl)acetate (1721 mg, 8.96 mmol) and 3-(5-iodothiazol-2-yl)cyclobutanone (250 mg, 0.896 mmol) in DMF (5 ml). The mixture was stirred at 65° C. for 16 h, then diluted with water (15 mL), and extracted with EA (2×15 mL). The organic layer was washed with water (30 mL), dried over Na₂SO₄. After filtration and concentration, the residue was purified by column chromatography (SiO₂, PE:EA=10:1) to the title compound.

Step D: cis-3-[5-(trifluoromethyl)-1,3-thiazol-2-yl]cyclobutanol. Sodium tetrahydroborate (37.6 mg, 0.995 mmol) was added to a mixture of 3-(5-(trifluoromethyl)thiazol-2-yl)-cyclobutanone (110 mg, 0.497 mmol) in MeOH (5 mL). The mixture was stirred at 0° C. for 1 h, then diluted with water (15 mL), and extracted with EA (2×15 mL). The organic layer was washed with water (20 mL), and dried over Na$_2$SO$_4$. After filtration and concentration, the residue was purified by prep-TLC (SiO$_2$, PE:EA=5:1) to afford the title compound.

Step E: 2-[3-(methoxymethoxy)isoxazol-5-yl]-5-({cis-3-[5-(trifluoromethyl)-1,3-thiazol-2-yl]-cyclobutyl}oxy)pyrazine. Sodium 2-methylpropan-2-olate (101 mg, 1.049 mmol) was added to a solution of cis-3-[5-(trifluoromethyl)-1,3-thiazol-2-yl]cyclobutanol (94 mg, 0.419 mmol) and 5-(5-bromopyrazin-2-yl)-3-(methoxymethoxy)isoxazole (100 mg, 0.350 mmol) in THF (3 mL). The mixture was stirred at 40° C. for 2 h, then quenched with water (10 mL), The pH of the mixture was adjusted to pH 4-5 with 2N aqueous HCl, and extracted with EA (2×10 mL). The organic layer was separated, washed with water (20 ml), and dried over Na$_2$SO$_4$. After filtration and concentration, the residue was purified by prep-HPLC to afford the title compound.

Step F: 5-[5-({cis-3-[5-(trifluoromethyl)-1,3-thiazol-2-yl]cyclobutyl}oxy)pyrazin-2-yl]-isoxazol-3-ol. A solution of 2-[3-(methoxymethoxy)isoxazol-5-yl]-5-({cis-3-[5-(trifluoro-methyl)-1,3-thiazol-2-yl]cyclobutyl}oxy)pyrazine (40 mg, 0.093 mmol) in THF (4 mL) and 3N HCl (1 mL) was stirred at 25° C. for 2 h. Then the reaction mixture was concentrated and lyophilized in MeOH to give the title compound. $^1$H NMR (400 MHz, CD$_3$OD) δ 8.60 (s, 1H), 8.29 (s, 1H), 8.14 (s, 1H), 6.44 (s, 1H), 5.34-5.37 (m, 1H), 3.68-3.74 (m, 1H), 3.09-3.11 (m, 2H), 2.57-2.59 (m, 2H). MS(ESI) m/z: 385.0[M+H]$^+$.

Example 7 ammonium 5-(5-{[cis-3-(4-bromophenyl)cyclobutyl]oxy}pyrazin-2-yl)isoxazol-3-olate

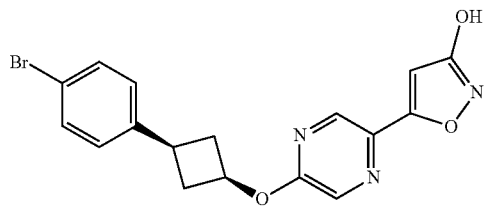 [SMILES: Oc1cc(-c2cnc(O[C@H]3C[C@@H](c4ccc(Br)cc4)C3)cn2)on1]

Step A: cis-3-(4-bromophenyl)cyclobutan-1-ol. To a solution of 3-(4-bromophenyl)cyclo-butanone (2.00 g, 8.89 mmol) in methanol (20 ml) at 0° C. under N$_2$ was added NaBH$_4$ (0.374 g, 9.77 mmol). The reaction mixture was stirred at 0° C. under N$_2$. After 90 min, the reaction was quenched by addition of saturated aqueous NaHCO$_3$ (50 mL) at 0° C. The reaction mixture was stirred at rt for 30 min, then concentrated under vacuum, and extracted with EtOAc (3×50 mL). The EtOAc extracts were combined, dried over Na$_2$SO$_4$, filtered and concentrated. The resulting residue was purified by column chromatography using EtOAc/hexanes as eluents (RediSep Gold 80 g HP silica gel) to afford the title compound.

Step B: 5-(5-(cis-3-(4-bromophenyl)cyclobutoxy)pyrazin-2-yl)-3-(methoxymethoxy)isoxazole. To a solution of cis-3-(4-bromophenyl)cyclobutanol (0.873 g, 3.85 mmol) in DMF (20 mL) at 0° C. was added NaH (0.182 g, 4.54 mmol). The reaction mixture was stirred at 0° C. under N$_2$ for 5 min. Then the reaction mixture was treated with 5-(5-bromopyrazin-2-yl)-3-(methoxymethoxy)-isoxazole (1 g, 3.50 mmol) at 0° C. The reaction mixture was stirred at 0° C. under N$_2$ for 10 min and then at RT for 2 h. Then the reaction mixture was cooled to 0° C. and quenched by addition of saturated NaHCO$_3$ (10 mL). The mixture was diluted with H$_2$O (50 mL) and extracted with EtOAc (3×50 mL). The organic extracts were combined, washed with H$_2$O (4×50 mL), dried over Na$_2$SO$_4$, filtered and concentrated. The resulting residue was purified by column chromatography using EtOAc/hexanes as eluents (RediSep Gold 80 g HP silica gel) to afford the title compound.

Step C: ammonium 5-(5-{[cis-3-(4-bromophenyl)cyclobutyl]oxy}pyrazin-2-yl)isoxazol-3-olate. To a solution of 5-(5-((cis-3-(4-bromophenyl)cyclobutoxy)pyrazin-2-yl)-3-(methoxymethoxy)-isoxazole (20 mg, 0.046 mmol) in THF (1 mL) and MeOH (250 μL) was added a solution of HCl (116 μL, 0.463 mmol, 4.0 M in 1,4-dioxane) at rt. The reaction mixture was stirred at rt under N$_2$ for 1 h, then concentrated. The resulting residue was purified by prep-HPLC (NH$_4$OH modifier) to afford the title compound. $^1$H NMR (500 MHz, DMSO-d$_6$): δ 8.70 (s, 1H), 8.40 (s, 1H), 7.50 (d, J=8.1 Hz, 2H), 7.27 (d, J=8.1 Hz, 2H), 6.53 (s, 1H), 5.24 (m, 1H), 3.22 (m, 1H), 2.92 (m, 2H), 2.19 (m, 2H). MS (ESI) m/z: 388.2 [M+H]$^+$.

Example 8 sodium 5-[6-({trans-3-[3-fluoro-5-(trifluoromethyl)pyridin-2-yl]-cyclobutyl}oxy)pyridin-3-yl]isoxazol-3-olate

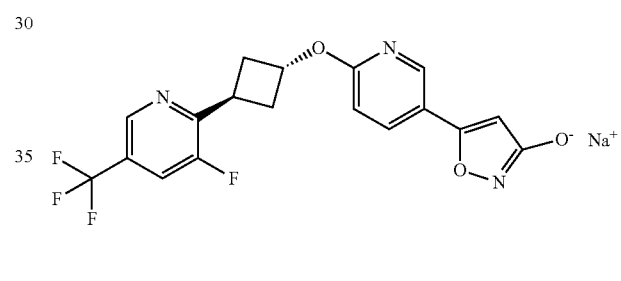

Example 9 sodium 5-[6-({cis-3-[3-fluoro-5-(trifluoromethyl)pyridin-2-yl]-cyclobutyl}oxy)pyridin-3-yl]isoxazol-3-olate

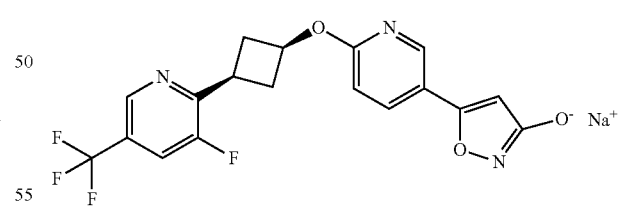

Step A: 3-(benzyloxy)-1-[3-fluoro-5-(trifluoromethyl)pyridin-2-yl]cyclobutanol. To a solution of 2-bromo-3-fluoro-5-(trifluoromethyl)pyridine (2 g, 8.20 mmol) in toluene (82 ml) was added dropwise n-BuLi (6.15 ml, 9.84 mmol) at −78° C. The mixture was stirred at at −78° C. for 40 min, then 3-(benzyloxy)cyclobutanone (1.878 g, 10.66 mmol) in toluene (10 mL) was added dropwise. The reaction mixture was stirred at −78° C. for 1 h, then warmed to 0° C. and quenched with 40 mL of saturated aqueous NH$_4$Cl. The organic layer was separated and concentrated. The resulting residue was purified by a SiO₂ column (0-40% EtOAc/hexanes) to afford the title compound. MS (ESI) m/z: 342.3 [M+H]⁺.

Step B: 2-[3-(benzyloxy)-1-chlorocyclobutyl]-3-fluoro-5-(trifluoromethyl)pyridine. SOCl₂ (0.545 mL, 7.47 mmol) was added to a stirred mixture of 3-(benzyloxy)-1-[3-fluoro-5-(trifluoro-methyl)pyridin-2-yl]cyclobutanol (510 mg, 1.494 mmol) in CH₂Cl₂ (14.6 mL). The reaction was stirred at rt overnight. Then water (10 mL) was added and the mixture was extracted with DCM (2×10 mL). The combined organic layers were washed with brine (10 mL), dried (Na₂SO₄), filtered and concentrated. The resulting residue was purified by column chromatography on silica gel (ISCO 40 g column), eluting with 0-50% EtOAc/hexane, to afford the title compound. MS (ESI) m/z: 360.3 [M+H]⁺.

Step C: 3-[3-fluoro-5-(trifluoromethyl)pyridin-2-yl]cyclobutanol. To a solution of the 2-[3-(benzyloxy)-1-chlorocyclobutyl]-3-fluoro-5-(trifluoromethyl)pyridine (300 mg, 0.834 mmol) in MeOH (7 mL) and formic acid (1.919 ml, 50.0 mmol) was added palladium on carbon (887 mg, 0.834 mmol). The reaction was stirred vigorously under N₂ for 3 h. Then the reaction mixture was filtered through Celite™ and concentrated. The resulting residue was purified by flash column chromatography on silica gel (ISCO 40 g column, gradient elution from 0-10% MeOH in CH₂Cl₂) to afford the title compound. MS (ESI) m/z: 236.1 [M+H]⁺.

Step D: 3-fluoro-2-[trans-3-({5-[3-(methoxymethoxy)isoxazol-5-yl]pyridin-2-yl}oxy)cyclo-butyl]-5-(trifluoromethyl)pyridine and 3-fluoro-2-[cis-3-({5-[3-(methoxymethoxy)isoxazol-5-yl]-pyridin-2-yl}oxy)cyclobutyl]-5-(trifluoromethyl)pyridine. Into a 100 mL flask was added 3-[3-fluoro-5-(trifluoromethyl)pyridin-2-yl]cyclobutanol (39.1 mg, 0.166 mmol) in THF (1039 µL), followed by the portionwise addition of NaH (19.94 mg, 0.499 mmol). The reaction mixture stirred at rt for 15 min, then a solution of 2-chloro-5-[3-(methoxymethoxy)isoxazol-5-yl]pyridine (40 mg, 0.166 mmol) in THF (1 mL) was added. The reaction mixture stirred at 50° C. for 30 min, then diluted with water, and extracted with EtOAc (2×15 mL). The organic layer was collected and dried over Na₂SO₄, filtered, and the filtrate was concentrated under reduced pressure. The resulting residue was purified by flash column chromatography on silica gel (ISCO 40 g column, eluting with 0-80% EtOAc in hexane) to afford a mixture of cis and trans stereoisomers. The mixture was separated by ChiralPak IC column (30×250 mm), 40% MeOH (0.2% NH₄OH)/CO₂ to afford the title compounds. MS (ESI) m/z: 440.3 [M+H+]. Cis isomer. MS (ESI) m/z: 440.3 [M+H+]. Trans isomer.

Example 8. sodium 5-[6-({trans-3-[3-fluoro-5-(trifluoromethyl)pyridin-2-yl]-cyclobutyl}-oxy)-pyridin-3-yl]-isoxazol-3-olate HCl (0.068 ml, 0.273 mmol) was added to a stirred, room temperature mixture of 5-[6-({trans-3-[3-fluoro-5-(trifluoromethyl)pyridin-2-yl]-cyclobutyl}-oxy)pyridin-3-yl]isoxazol-3-ol (15 mg, 0.034 mmol) in CH₂Cl₂ (0.8 mL) and MeOH (0.8 mL). The mixture was stirred at room temperature for 2 h, then dried under vacuum to remove the solvent. The resulting residue was dissolved in DMSO and purified by Gilson HPLC under basic conditions (NH₄OH), and the fractions containing the desired compound were dried in vacuo. NaOH (0.086 mL, 8.60 µmol) was added to a stirred, room temperature mixture of the desired compound 5-[6-({trans-3-[3-fluoro-5-(trifluoromethyl)pyridin-2-yl]-cyclobutyl}oxy)-pyridin-3-yl]isoxazol-3-ol (3.4 mg, 8.60 µmol) in acetonitrile (0.2 mL) and water (0.200 mL). The mixture was stirred at room temperature for 30 minutes, then dried in vacuo to afford the title compound. MS (ESI) m/z: 396.3 [M+H]⁺.

Example 9. sodium 5-[6-({cis-3-[3-fluoro-5-(trifluoromethyl)pyridin-2-yl]cyclobutyl}-oxy)pyridine HCl (0.109 mL, 0.437 mmol) was added to a stirred, room temperature mixture of 5-[6-({cis-3-[3-fluoro-5-(trifluoromethyl)pyridin-2-yl]cyclobutyl}oxy)pyridin-3-yl]isoxazol-3-ol (24 mg, 0.055 mmol) in CH₂Cl₂ (0.8 mL) and MeOH (0.8 mL). The mixture was stirred at room temperature for 2 h, then dried under vacuum, and the resulting residue was dissolved in DMSO and purified by Gilson HPLC under basic conditions (NH₄OH). The fractions containing the desired compound were dried in vacuo. NaOH (0.301 mL, 0.03 mmol) was added to a stirred, cooled room temperature mixture of the desired compound 5-[6-({cis-3-[3-fluoro-5-(trifluoromethyl)pyridin-2-yl]cyclobutyl}oxy)pyridin-3-yl]isoxazol-3-ol (11.9 mg, 0.03 mmol) in acetonitrile (0.2 mL) and water (0.200 mL). The mixture was stirred at room temperature for 30 min, then dried in vacuo to afford the title compound. MS (ESI) m/z: 396.3 [M+H]⁺.

Example 10 sodium 5-(5-{[cis-3-(4-fluorophenyl)cyclobutyl]oxy}pyrazin-2-yl)isoxazol-3-olate

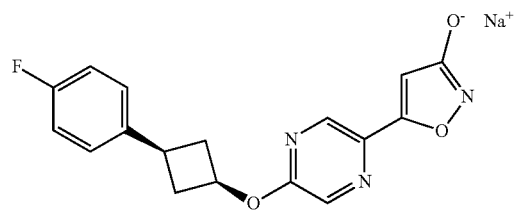 [SMILES: [O-]c1cc(-c2cnc(O[C@H]3C[C@@H](c4ccc(F)cc4)C3)cn2)on1 ; [Na+]]

Step A: 2,2-dichloro-3-(4-fluorophenyl)cyclobutanone. To a solution of 1-fluoro-4-vinyl-benzene (30 g, 246 mmol) in anhydrous Et₂O (900 mL) were added activated zinc (32.1 g, 491 mmol, washed with 1% aq HCl) and copper (II) acetate (4.46 g, 24.56 mmol) at 20° C. under nitrogen. The mixture was stirred for 30 min, followed by the dropwise addition of a solution of 2,2,2-trichloroacetyl chloride (89 g, 491 mmol) in anhydrous Et₂O (400 mL). The mixture was stirred at 20° C. for 14 h, then washed with water (500 mL), saturated NaHCO₃ (500 mL) and extracted with EA (3×300 mL). The combined organic layers were washed with brine (3×100 mL) and dried over Na₂SO₄. After filtration and concentration, the resulting residue was purified by column chromatography (SiO₂, PE:EA=10:1) to give the title compound.

Step B: 3-(4-fluorophenyl)cyclobutanone. To a mixture of ammonium chloride (92 g, 1716 mmol) and 2,2-dichloro-3-(4-fluorophenyl)cyclobutanone (40 g, 172 mmol) in MeOH (500 mL) was added portionwise zinc (56.1 g, 858 mmol) at 0° C. The mixture was stirred at 20° C. for 12 h, then filtered and the filtrate was concentrated. The resulting residue was purified by silica gel chromatography (SiO₂, PE:EtOAc=20:1, v/v) to afford the title compound.

Step C: cis-3-(4-fluorophenyl)cyclobutanol. To a mixture of 3-(4-fluorophenyl)cyclobutanone (20 g, 122 mmol) in Et₂O (250 mL) was added LAH (6.94 g, 183 mmol) at −40° C. The reaction was stirred for 2 h, then diluted by the dropwise addition of water (8 mL), dried over Na₂SO₄, and filtered. The filtrate was concentrated in vacuo to afford the title compound.

Step D: 2-{[cis-3-(4-fluorophenyl)cyclobutyl]oxy}-5-[3-(methoxymethoxy)isoxazol-5-yl]-pyrazine. To a mixture of cis-3-(4-fluorophenyl)cyclobutanol (13.25 g, 80 mmol) and 5-(5-bromopyrazin-2-yl)-3-(methoxymethoxy)isoxazole (15.2 g, 53.1 mmol) in THF (550 mL) was added sodium 2-methylpropan-2-olate (15.32 g, 159 mmol). The mixture was stirred at 60° C. for 2 h. Then the mixture was poured into aqueous NH₄Cl (200 mL), and extracted with EtOAc (3×100 mL). The combined organic layers were washed with brine (200 mL), dried over Na₂SO₄, and filtered. The filtrate was concentrated to afford the title compound. MS (ESI) m/z: 372.1 [M+H]⁺.

Step E: sodium 5-(5-{[cis-3-(4-fluorophenyl)cyclobutyl]oxy}pyrazin-2-yl)isoxazol-3-olate. A mixture of 2-{[cis-3-(4-fluorophenyl)cyclobutyl]oxy}-5-[3-(methoxymethoxy)-isoxazol-5-yl]-pyrazine (16 g, 43.1 mmol) in THF (500 mL) was adjusted to pH 3-4 with HCl (20 mL, 60.0 mmol). The mixture was stirred at 60° C. for 1.5 h, then poured into aq. NH₄Cl (300 mL), and extracted with EtOAc (5×100 mL). The combined organic layers were washed with brine (200 mL), dried over MgSO₄, and filtered. The filtrate was concentrated under vacuum. The resulting residue was suspended in MeOH (100 mL) and stirred for 20 min. Then the mixture was filtered and the solid was dried in vacuum to give the free form of the title compound. The solid was then suspended in MeCN (500 mL), and aqueous NaOH (58.2 mL, 1 g/50 mL water) was added dropwise. The mixture was freeze-dried to give the title compound. ¹H NMR (400 MHz, CD₃OD) δ 8.48 (s, 1H), 8.19 (s, 1H), 7.27 (dd, J=5.48, 8.22 Hz, 2H), 7.00 (t, J=8.80 Hz, 2H), 5.20-5.30 (m, 1H), 3.14-3.25 (m, 1H), 2.89-3.01 (m, 2H), 2.16-2.27 (m, 2H). MS (ESI) m/z: 328.1 [M+H]⁺.

Example 11 ammonium 5-[6-({cis-3-[2-fluoro-5-(trifluoromethoxy)phenyl]cyclo-butyl}oxy)pyridin-3-yl]isoxazol-3-olate

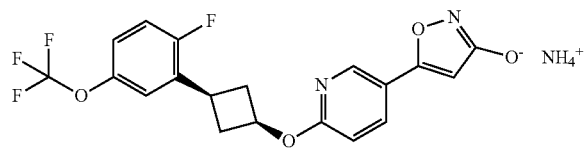 [SMILES: [O-]c1cc(-c2ccc(O[C@H]3C[C@@H](c4cc(OC(F)(F)F)ccc4F)C3)nc2)on1 ; [NH4+]]

Step A: 3-(benzyloxy)-1-(2-fluoro-5-(trifluoromethoxy)phenyl)cyclobutan-1-ol. A solution of 2-bromo-1-fluoro-4-(trifluoromethoxy)benzene (1.295 g, 5 mmol) in THF (10 mL) was purged with N₂ for 5 min, then isopropylmagnesium lithium chloride (3.85 mL, 5.00 mmol) was added at 0° C. The reaction was kept at 0° C. for 30 min, followed by the dropwise addition of a solution of 3-(benzyloxy)cyclobutanone (0.881 g, 5.00 mmol) in THF (5 mL). The reaction was allowed to warm to room temperature and stirred overnight. Then the reaction was quenched with a minimum amount of the saturated aqueous NH₄Cl. The mixture was dried over Na₂SO₄ and concentrated. The resulting residue was purified by normal phase column chromatography (SiO₂) using 25% of EtOAc in hexanes to give the title compound.

Step B: 2-(cis-3-(benzyloxy)cyclobutyl)-1-fluoro-4-(trifluoromethoxy)benzene. A suspension of sodium hydride (31.4 mg, 0.786 mmol) in diethyl ether (7.86 mL) was treated with a solution of 3-(benzyloxy)-1-(2-fluoro-5-(trifluoromethoxy)phenyl)cyclobutanol (140 mg, 0.393 mmol) in ether (1 mL) at 0° C. The reaction was stirred at 0° C. for 30 min and at room temperature for 30 min, and then cooled to 0° C. A solution of methanesulfonyl chloride (60.8 μL, 0.786 mmol) in ether (1 mL) was added, and the reaction was stirred for 1 hr at 0° C. Then the reaction was cooled to −78° C. and LAH (2.0 M in THF, 1.572 mL) was added drop wise. The cooling bath was removed and the reaction was allowed to warm to rt and stirred at room temperature overnight. The reaction mixture was slowly added to a saturated aqueous solution of Rochelle's salt, then EtOAc was added and the mixture was stirred for 1 hr until 2 layers were clearly separated. The aqueous layer was extracted 3 times with EtOAc, dried over Na₂SO₄ and concentrated to give the crude product, which was purified by normal phase column chromatography (SiO₂) using 10% EtOAc in hexanes to give the cis product as the major stereoisomer.

Step C: cis-3-(2-fluoro-5-(trifluoromethoxy)phenyl)cyclobutan-1-ol. To a solution of 2-(cis-3-(benzyloxy)cyclobutyl)-1-fluoro-4-(trifluoromethoxy)benzene (74 mg, 0.218 mmol) in MeOH (2.18 mL) was added 15% Pd/C (10% on C). The reaction was stirred at 1 atm of H₂ for 1 hr. Then the reaction was filtered and concentrated to afford the title compound, which was used in the next step without further purification.

Step D: ammonium 5-[6-({cis-3-[2-fluoro-5-(trifluoromethoxy) phenyl]cyclobutyl}oxy)-pyridin-3-yl]isoxazol-3-olate. A solution of cis-3-(2-fluoro-5-(trifluoromethoxy)phenyl)-cyclobutanol (55 mg, 0.220 mmol) in THF (2.2 mL) was purged with N₂ for 5 min and NaHMDS (1.0 M in THF, 0.242 mL) was added at rt. After stirring for 10 min, a solution of 5-(6-chloropyridin-3-yl)-3-(methoxymethoxy)isoxazole (52.9 mg, 0.220 mmol) in THF (1.0 M, 0.22 mL) was added, and the reaction was heated to 80° C. for 2 h. The reaction was quenched with several drops of pH 7 buffer and the solvent was removed. The resulting crude was purified by normal phase column chromatography (SiO₂) using 15% of EtOAc in hexanes to give the MOM protected product. The MOM protected product was dissolved in 1,4-dioxane and treated with HCl in 1,4-dioxane (4.0 M, 1 mL), stirred overnight and solvent was removed under reduced pressure. The resulting residue was purified by reverse phase column chromatography (NH₄OH modifier) to give the title compound. ¹H NMR (500 MHz, CD₃OD) δ 2.31-2.25 (2H, m), 3.06-3.01 (2H, m), 3.49-3.42 (1H, m), 5.35-5.29 (1H, m), 6.31 (1H, s), 6.91 (1H, dd, J=8.7, 0.8 Hz), 7.21-7.15 (2H, m), 7.26 (1H, d, J=6.2 Hz), 8.05 (1H, dd, J=8.7, 2.5 Hz), 8.57-8.56 (1H, m).

Example 12

5-(4-{[trans-3-(4-fluorophenyl)cyclobutyl]oxy}phenyl)isoxazol-3-ol

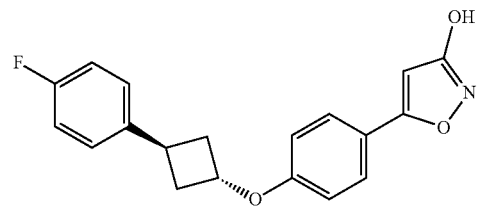 [SMILES: Oc1cc(-c2ccc(O[C@H]3C[C@H](c4ccc(F)cc4)C3)cc2)on1]

Step A: 5-(4-{[trans-3-(4-fluorophenyl)cyclobutyl]oxy}phenyl)-3-(methoxymethoxy)isoxazole. To a solution of cis-3-(4-fluorophenyl)cyclobutan-1-ol (83 mg, 0.497 mmol), 4-(3-(methoxymethoxy)isoxazol-5-yl)phenol (100 mg, 0.452 mmol) and triphenylphosphine (polymer-bound, 1.6 mmol/g loading, 452 mg, 0.723 mmol) in THF (6 mL) was added diisopropyl azodicarboxylate (137 mg, 0.678 mmol) at rt. The reaction was stirred at 60° C. overnight, then cooled, filtered, and washed with EA. The solvent was evaporated under reduced pressure to afford the title compound, which was used in the next step without purification. MS (ESI) m/z: 370 [M+H]$^+$.

Step B: 5-(4-{[trans-3-(4-fluorophenyl)cyclobutyl]oxy}phenyl)isoxazol-3-ol. To a solution of 5-(4-{[trans-3-(4-fluorophenyl)cyclobutyl]oxy}phenyl)-3-(methoxymethoxy)isoxazole (167 mg, 0.452 mmol) in MeOH (2 mL) was added 4N HCl in dioxane (1130 µl, 4.52 mmol). The mixture was stirred at rt for 1 h. Then the reaction was concentrated. The resulting residue was purified by prep-HPLC (TFA modifier) to afford the title compound. $^1$H NMR (500 MHz, Acetone-d$_6$) δ 2.73-2.64 (4H, m), 3.83-3.77 (1H, m), 5.09-5.04 (1H, m), 6.33 (1H, s), 7.03-7.00 (2H, m), 7.13-7.10 (2H, m), 7.43-7.40 (2H, m), 7.76-7.73 (2H, m). MS (ESI) m/z: 326 [M+H]$^+$.

Example 13 ammonium 5-(6-{[cis-3-(4-ethylphenyl)cyclobutyl]oxy}pyridin-3-yl)-4-fluoroisoxazol-3-olate

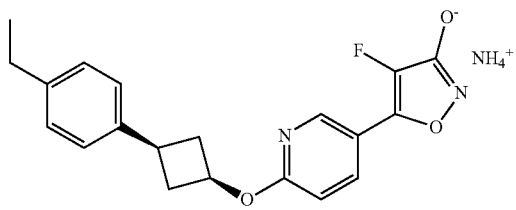 [SMILES: CCc1ccc([C@H]2C[C@@H](Oc3ccc(-c4onc([O-])c4F)cn3)C2)cc1 ; [NH4+]]

Step A: 3-(4-vinylphenyl)cyclobutan-1-one. To a solution of 3-(4-bromophenyl)-cyclobutan-1-one (3.93 g, 17.46 mmol), potassium vinyltrifluoroborate (3.51 g, 26.2 mmol), and sodium carbonate (3.70 g, 34.9 mmol) in 1,4-dioxane (120 mL) and water (13.33 mL) was added [1,1′-bis(diphenylphosphino)ferrocene]dichloropalladium(II) (1.278 g, 1.746 mmol) under N$_2$. The reaction was stirred at 120° C. overnight, then cooled, diluted with EA, and washed with water. The organic layer was dried over Na$_2$SO$_4$ and filtered. The filtrate was evaporated under reduced pressure and the resulting residue was purified by flash column chromatography on silica gel (eluting with EA/hexane) to afford the title compound.

Step B: cis-3-(4-ethenylphenyl)cyclobutanol. To a solution of 3-(4-vinylphenyl)cyclo-butan-1-one (707 mg, 4.11 mmol) in THF (13 mL) was added NaBH$_4$ (171 mg, 4.52 mmol) at 0° C. The reaction was stirred at rt. for 1 h. Then the reaction was quenched with saturated sodium bicarbonate and stirred at rt. for 1 h. The reaction was extracted with EA, and washed with brine. The organic layer was dried over Na$_2$SO$_4$ and filtered and concentrated. The resulting residue was purified by flash column chromatography on silica gel (eluting with EA/hexane) to afford the title compound.

Step C: cis-3-(4-ethylphenyl)cyclobutanol. To a solution of cis-3-(4-ethenylphenyl)cyclo-butanol (120 mg, 0.689 mmol) in MeOH (5 mL) was added Pd/C (73.3 mg, 0.069 mmol, 10% Wt). The reaction was stirred at r.t. under 1 atm of H$_2$ for 1 h. Then the reaction was filtered through Celite™, washed with EA, and the filtrate was evaporated under reduced pressure to afford the title compound.

Step D: 2-{[cis-3-(4-ethylphenyl)cyclobutyl]oxy}-5-[4-fluoro-3-(methoxymethoxy)-isoxazol-5-yl]pyridine. To a solution of cis-3-(4-ethylphenyl)cyclobutanol (47.7 mg, 0.271 mmol) in THF (1.5 mL) was added sodium hydride (13 mg, 0.541 mmol). The reaction was stirred at r.t. for 5 min, then a solution of 5-(6-chloropyridin-3-yl)-4-fluoro-3-(methoxymethoxy)isoxazole (70 mg, 0.271 mmol) in THF (1 mL) was added. The reaction mixture was stirred at rt. overnight, then quenched with H$_2$O and extracted with EA. The organic layer were dried over Na$_2$SO$_4$, filtered and concentrated to afford the title compound, which was used in the next step without further purification. MS (ESI) m/z: 399 [M+H]$^+$.

Step E: ammonium 5-(6-{[cis-3-(4-ethylphenyl)cyclobutyl]oxy}pyridin-3-yl)-4-fluoro-isoxazol-3-olate. To a solution of 2-{[cis-3-(4-ethylphenyl)cyclobutyl]oxy}-5-[4-fluoro-3-(methoxymethoxy)isoxazol-5-yl]pyridine (108 mg, 0.271 mmol) in DCM (1 mL) was added 4N HCl in dioxane (1 mL, 4 mmol). The mixture was stirred at rt. for 1 h. Then the reaction was concentrated and the resulting residue was purified by prep-HPLC (NH$_4$OH modifier) to afford the title compound. $^1$H NMR (500 MHz, Acetone-d$_6$) δ 1.21 (3H, t, J=7.6 Hz), 2.25-2.18 (2H, m), 2.62 (2H, q, J=7.6 Hz), 2.99-2.93 (2H, m), 3.27-3.20 (1H, m), 5.35-5.29 (1H, m), 6.99 (1H, dd, J=8.7, 0.8 Hz), 7.19 (2H, d, J=8.0 Hz), 7.24 (2H, d, J=8.0 Hz), 8.03 (1H, dd, J=8.7, 2.5 Hz), 8.56 (1H, d, J=2.5 Hz). MS (ESI) m/z: 355 [M+H]$^+$.

TABLE 1

The compounds of Examples 14-60 were prepared from the appropriate previously described or commercially available starting materials using procedures similar to those in the Examples herein

| Example | Structure | Name | Exact Mass [M + H]$^+$ |
|---|---|---|---|
| 14 | 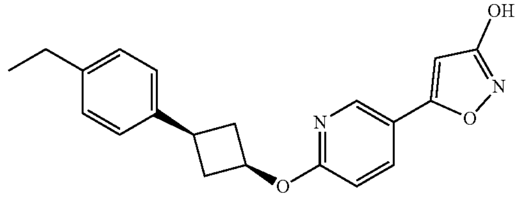 [SMILES: CCc1ccc([C@H]2C[C@@H](Oc3ccc(-c4cc(O)no4)cn3)C2)cc1] | 5-(6-{[cis-3-(4-ethylphenyl)-cyclobutyl]oxy}pyridin-3-yl)isoxazol-3-ol | 337 |

TABLE 1-continued

The compounds of Examples 14-60 were prepared from the appropriate previously
described or commercially available starting materials using procedures similar to those in the Examples herein

| Example | Structure | Name | Exact Mass [M + H]+ |
|---|---|---|---|
| 15 | 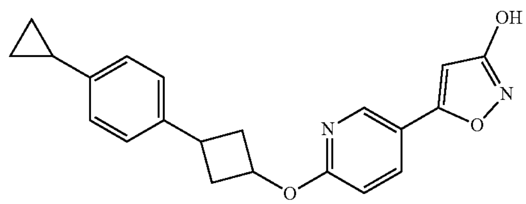 [SMILES: Oc1cc(-c2ccc(OC3CC(c4ccc(C5CC5)cc4)C3)nc2)on1] | 5-(6-{[3-(4-cyclo-propyl-phenyl)cyclobutyl]oxy}pyridin-3-yl)isoxazol-3-ol | 349 |
| 16 | 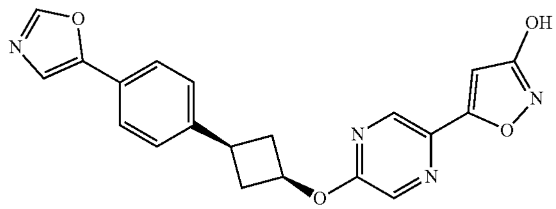 [SMILES: Oc1cc(-c2cnc(O[C@H]3C[C@@H](c4ccc(-c5cnco5)cc4)C3)cn2)on1] | 5-[5-({cis-3-[4-(1,3-oxazol-5-yl)phenyl]cyclobutyl}oxy)pyrazin-2-yl]isoxazol-3-ol | 377 |
| 17 | 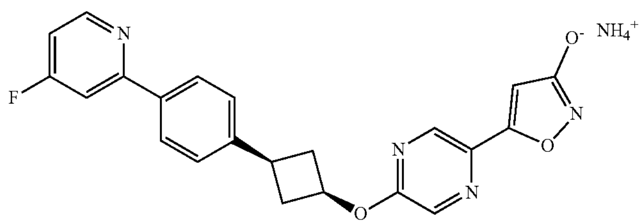 [SMILES: [O-]c1cc(-c2cnc(O[C@H]3C[C@@H](c4ccc(-c5cc(F)ccn5)cc4)C3)cn2)on1 ; [NH4+]] | ammonium 5-[5-({cis-3-[4-(4-fluoropyridin-2-yl)phenyl]cyclobutyl}oxy)pyrazin-2-yl]isoxazol-3-olate | 405 |
| 18 | 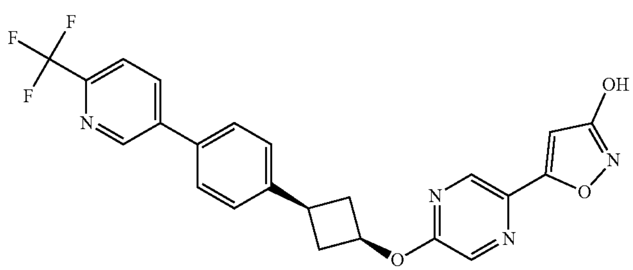 [SMILES: Oc1cc(-c2cnc(O[C@H]3C[C@@H](c4ccc(-c5ccc(C(F)(F)F)nc5)cc4)C3)cn2)on1] | 5-{5-[(cis-3-{4-[6-(trifluoromethyl)pyridin-3-yl]phenyl}cyclobutyl)oxy]pyrazin-2-yl}isoxazol-3-ol | 455 |
| 19 | 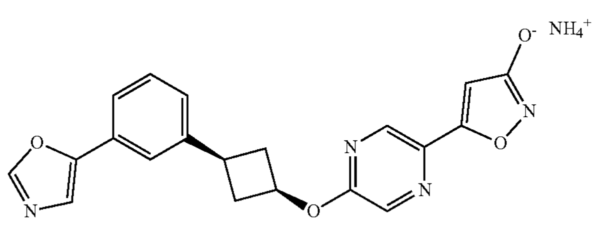 [SMILES: [NH4+] ; [O-]c1cc(-c2cnc(O[C@H]3C[C@@H](c4cccc(-c5cnco5)c4)C3)cn2)on1] | ammonium 5-[5-({cis-3-[3-(1,3-oxazol-5-yl)phenyl]-cyclobutyl}oxy)pyrazin-2-yl]isoxazol-3-olate | 377 |
| 20 | 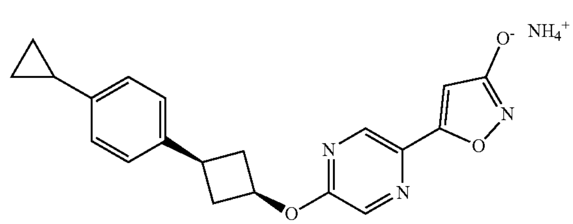 [SMILES: [NH4+] ; [O-]c1cc(-c2cnc(O[C@H]3C[C@@H](c4ccc(C5CC5)cc4)C3)cn2)on1] | ammonium 5-(5-{[cis-3-(4-cyclopropylphenyl)cyclobutyl]oxy}pyrazin-2-yl)isoxazol-3-olate | 350 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 21 | 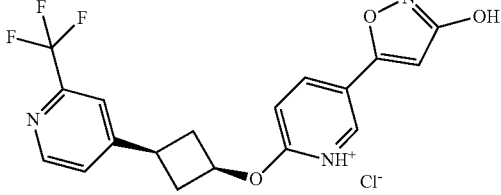 | 5-(3-hydroxyisoxazol-5-yl)-2-({cis-3-[2-(trifluoromethyl)-pyridin-4-yl]cyclobutyl}-oxy)pyridinium chloride | 378 |
| 22 | 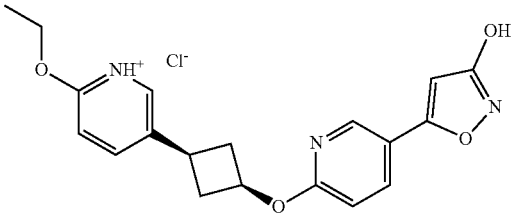 [SMILES: CCOc1ccc([C@H]2C[C@@H](Oc3ccc(-c4cc(O)no4)cn3)C2)c[nH+]1 ; [Cl-]] | 2-ethoxy-5-(cis-3-{[5-(3-hydroxyisoxazol-5-yl)pyridin-2-yl]oxy}cyclobutyl)-pyridinium chloride | 354 |
| 23 | 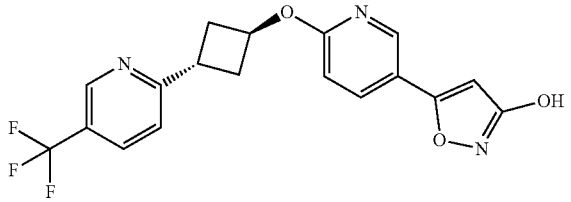 [SMILES: Oc1cc(-c2ccc(O[C@H]3C[C@H](c4ccc(C(F)(F)F)cn4)C3)nc2)on1] | 5-[6-({trans-3-[5-(trifluoromethyl)pyridin-2-yl]cyclobutyl}oxy)pyridin-3-yl]isoxazol-3-ol | 378 |
| 24 | 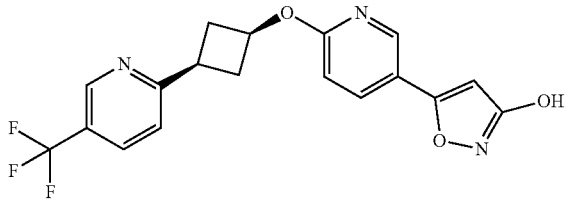 [SMILES: Oc1cc(-c2ccc(O[C@H]3C[C@@H](c4ccc(C(F)(F)F)cn4)C3)nc2)on1] | 5-[6-({cis-3-[5-(trifloromethyl)pyridin-2-yl]cyclobutyl}oxy)pyridin-3-yl]isoxazol-3-ol | 378 |
| 25 | 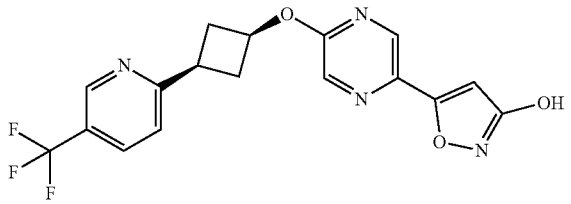 [SMILES: Oc1cc(-c2cnc(O[C@H]3C[C@@H](c4ccc(C(F)(F)F)cn4)C3)cn2)on1] | 5-[5-({cis-3-[5-(trifluoromethyl)pyridin-2-yl]cyclobutyl}oxy)pyrazin-2-yl]isoxazol-3-ol | 379 |
| 26 | 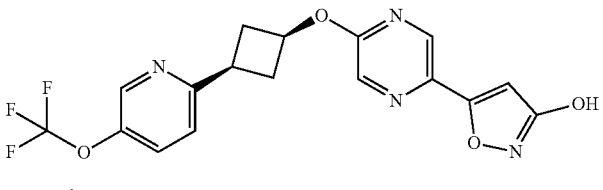 | 5-[5-({cis-3-[5-(trifluoromethoxy)pyridin-2-yl]cyclobutyl}oxy)pyrazin-2-yl]isoxazol-3-ol | 395 |
| 27 | 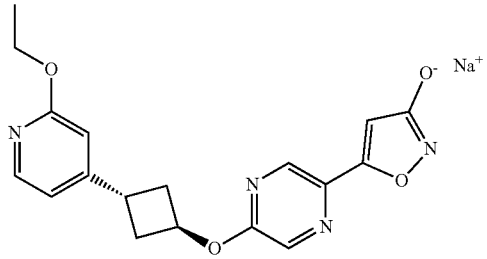 [SMILES: CCOc1cc([C@H]2C[C@H](Oc3cnc(-c4cc([O-])no4)cn3)C2)ccn1 ; [Na+]] | sodium 5-(5-{[trans-3-(2-ethoxypyridin-4-yl)cyclobutyl]oxy}pyrazin-2-yl)isoxazol-3-olate | 355 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 28 | 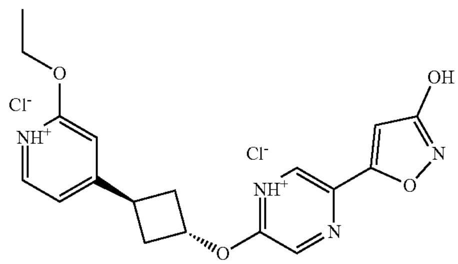 [SMILES: [Cl-] ; CCOc1cc([C@H]2C[C@H](Oc3cnc(-c4cc(O)no4)c[nH+]3)C2)cc[nH+]1 ; [Cl-]] | 2-ethoxy-4-(trans-3-{[5-(3-hydroxyisoxazol-5-yl)pyridinium-2-yl]oxy}cyclobutyl)pyridinium dichloride | 354 |
| 29 | 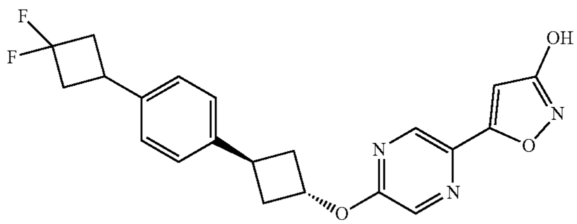 [SMILES: Oc1cc(-c2cnc(O[C@H]3C[C@H](c4ccc(C5CC(F)(F)C5)cc4)C3)cn2)on1] | 5-[5-({trans-3-[4-(3,3-difluorocyclobutyl)phenyl]cyclobutyl}oxy)pyrazin-2-yl]isoxazol-3-ol | 400 |
| 30 | 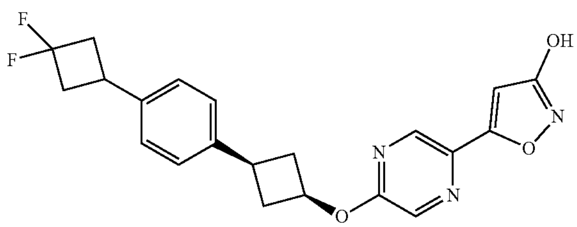 [SMILES: Oc1cc(-c2cnc(O[C@H]3C[C@@H](c4ccc(C5CC(F)(F)C5)cc4)C3)cn2)on1] | 5-[5-({cis-3-[4-(3,3-difluorocyclobutyl)phenyl]cyclobutyl}oxy)pyrazin-2-yl]isoxazol-3-ol | 400 |
| 31 | 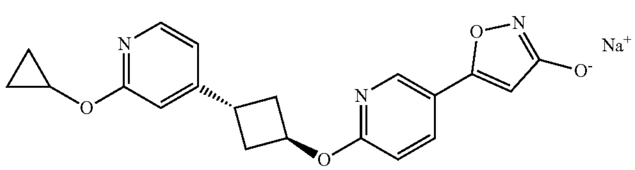 [SMILES: [O-]c1cc(-c2ccc(O[C@H]3C[C@H](c4ccnc(OC5CC5)c4)C3)nc2)on1 ; [Na+]] | sodium 5-[6-({trans-3-[2-(cyclopropyloxy)pyridin-4-yl]cyclobutyl}oxy)pyridin-3-yl]isoxazol-3-olate | 366 |
| 32 | 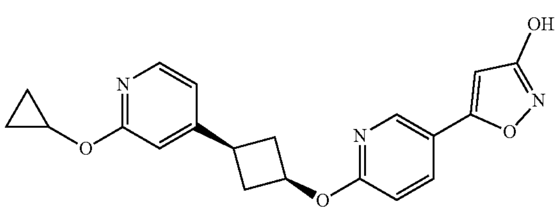 [SMILES: Oc1cc(-c2ccc(O[C@H]3C[C@@H](c4ccnc(OC5CC5)c4)C3)nc2)on1] | 5-[6-({cis-3-[2-(cyclopropyloxy)pyridin-4-yl]cyclobutyl}oxy)pyridin-3-yl]isoxazol-3-ol | 366 |
| 33 | 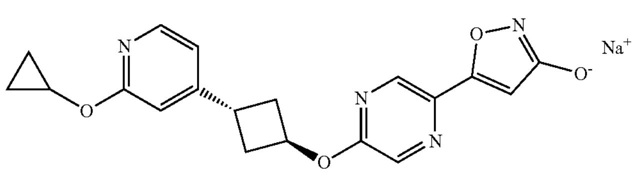 [SMILES: [O-]c1cc(-c2cnc(O[C@H]3C[C@H](c4ccnc(OC5CC5)c4)C3)cn2)on1 ; [Na+]] | sodium 5-[5-({trans-3-[2-(cyclopropyloxy)pyridin-4-yl]cyclobutyl}oxy)pyrazin-2-yl]isoxazol-3-olate | 367 |
| 34 | 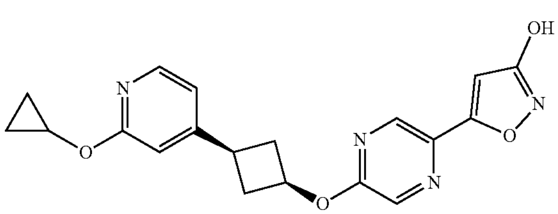 [SMILES: Oc1cc(-c2cnc(O[C@H]3C[C@@H](c4ccnc(OC5CC5)c4)C3)cn2)on1] | 5-[5-({cis-3-[2-(cyclopropyloxy)pyridin-4-yl]cyclobutyl}oxy)pyrazin-2-yl]isoxazol-3-ol | 367 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 35 | 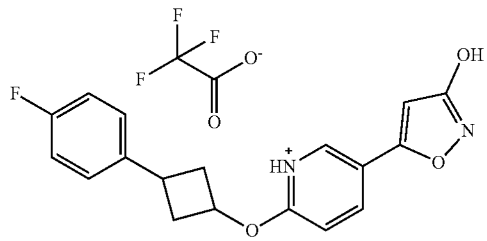 [SMILES: Oc1cc(-c2ccc(OC3CC(c4ccc(F)cc4)C3)[nH+]c2)on1 ; O=C([O-])C(F)(F)F] | 5-(6-{[3-(4-fluorophenyl)cyclobutyl]oxy}pyridin-3-yl)isoxazol-3-ol trifluoroacetate | 327 |
| 36 | 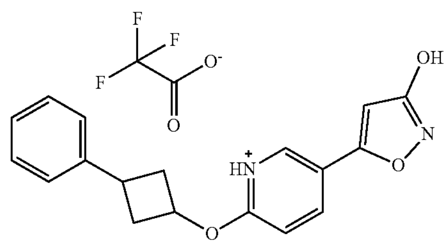 [SMILES: Oc1cc(-c2ccc(OC3CC(c4ccccc4)C3)[nH+]c2)on1 ; O=C([O-])C(F)(F)F] | 5-{6-[(3-phenylcyclobutyl)oxy]pyridin-3-yl}isoxazol-3-ol trifluoroacetate | 309 |
| 37 | 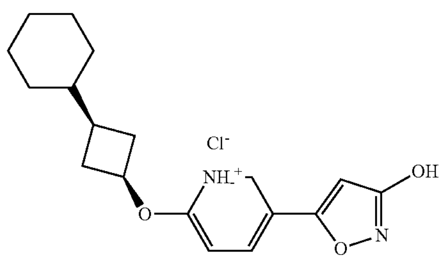 | 2-[(cis-3-cyclohexylcyclobutyl)oxy]-5-(3-hydroxyisoxazol-5-yl)pyridinium chloride | 315 |
| 38 | 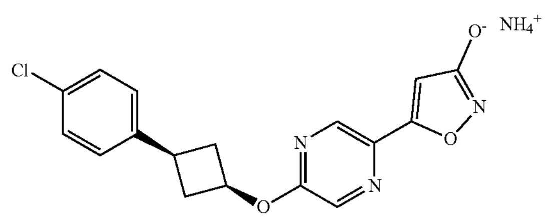 [SMILES: [NH4+] ; [O-]c1cc(-c2cnc(O[C@H]3C[C@@H](c4ccc(Cl)cc4)C3)cn2)on1] | sodium 5-(5-{[cis-3-(4-chlorophenyl)cyclobutyl]oxy}pyrazin-2-yl)isoxazol-3-olate | 344 |
| 39 | 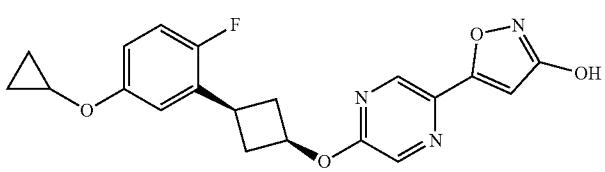 [SMILES: Oc1cc(-c2cnc(O[C@H]3C[C@@H](c4cc(OC5CC5)ccc4F)C3)cn2)on1] | 5-[5-({cis-3-[5-(cyclopropyloxy)-2-fluorophenyl]cyclobutyl}oxy)pyrazin-2-yl]isoxazol-3-ol | 384 |
| 40 | 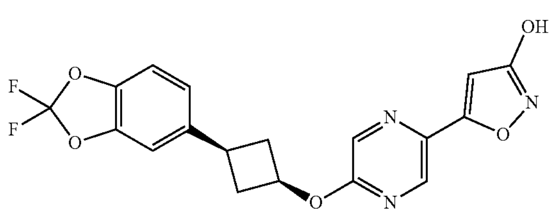 [SMILES: Oc1cc(-c2cnc(O[C@H]3C[C@@H](c4ccc5c(c4)OC(F)(F)O5)C3)cn2)on1] | 5-(5-{[cis-3-(2,2-difluoro-1,3-benzodioxol-5-yl)cyclobutyl]oxy}pyrazin-2-yl)isoxazol-3-ol | 390 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 41 | 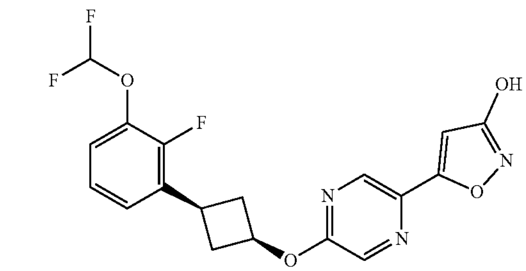 [SMILES: Oc1cc(-c2cnc(O[C@H]3C[C@@H](c4cccc(OC(F)F)c4F)C3)cn2)on1] | 5-[5-({cis-3-[3-(difluoromethoxy)-2-fluorophenyl]cyclobutyl}oxy)pyrazin-2-yl]isoxazol-3-ol | 394 |
| 42 | 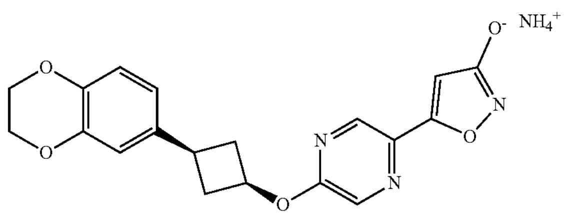 [SMILES: [NH4+] ; [O-]c1cc(-c2cnc(O[C@H]3C[C@@H](c4ccc5c(c4)OCCO5)C3)cn2)on1] | ammonium 5-(5-{[cis-3-(2,3-dihydro-1,4-benzodioxin-6-yl)cyclobutyl]oxy}pyrazin-2-yl)isoxazol-3-olate | 368 |
| 43 | 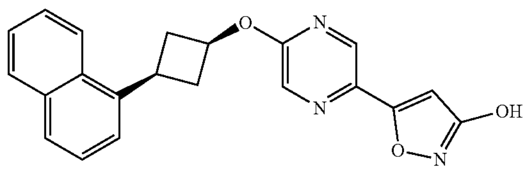 [SMILES: Oc1cc(-c2cnc(O[C@H]3C[C@@H](c4cccc5ccccc54)C3)cn2)on1] | 5-{5-[(cis-3-naphthalen-1-ylcyclobutyl)oxy]pyrazin-2-yl}isoxazol-3-ol | 360 |
| 44 | 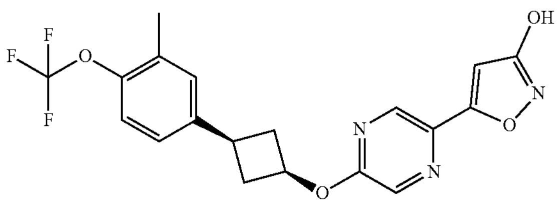 [SMILES: Cc1cc([C@H]2C[C@@H](Oc3cnc(-c4cc(O)no4)cn3)C2)ccc1OC(F)(F)F] | 5-[5-({cis-3-[3-methyl-4-(trifluoromethoxy)phenyl]cyclobutyl}oxy)pyrazin-2-yl]isoxazol-3-ol | 408 |
| 45 | 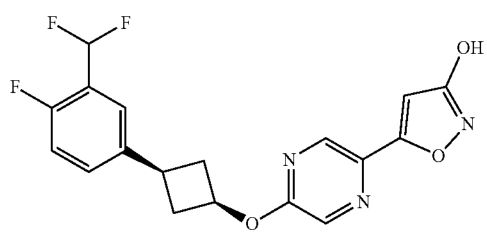 [SMILES: Oc1cc(-c2cnc(O[C@H]3C[C@@H](c4ccc(F)c(C(F)F)c4)C3)cn2)on1] | 5-[5-({cis-3-[3-(difluoromethyl)-4-fluorophenyl]cyclobutyl}oxy)pyrazin-2-yl]isoxazol-3-ol | 378 |
| 46 | 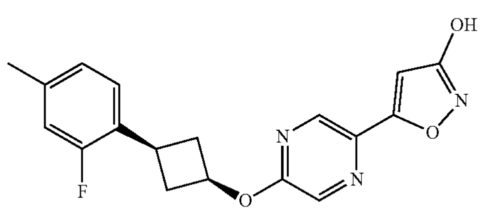 [SMILES: Cc1ccc([C@H]2C[C@@H](Oc3cnc(-c4cc(O)no4)cn3)C2)c(F)c1] | 5-(5-{[cis-3-(2-fluoro-4-methylphenyl)cyclobutyl]oxy}pyrazin-2-yl)isoxazol-3-ol | 342 |
| 47 | 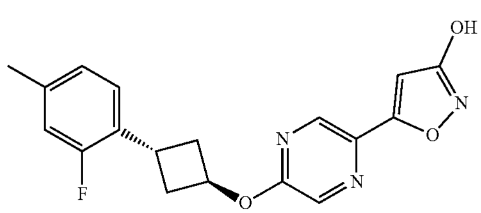 [SMILES: Cc1ccc([C@H]2C[C@H](Oc3cnc(-c4cc(O)no4)cn3)C2)c(F)c1] | 5-(5-{[trans-3-(2-fluoro-4-methylphenyl)cyclobutyl]oxy}pyrazin-2-yl)isoxazol-3-ol | 342 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 48 | 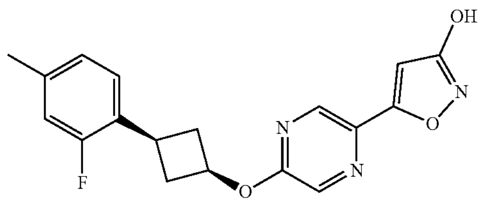 [SMILES: Cc1ccc([C@H]2C[C@@H](Oc3cnc(-c4cc(O)no4)cn3)C2)c(F)c1] | 5-(5-{[cis-3-(2-fluoro-4-methylphenyl)cyclobutyl]oxy}pyrazin-2-yl)isoxazol-3-ol | 342 |
| 49 | 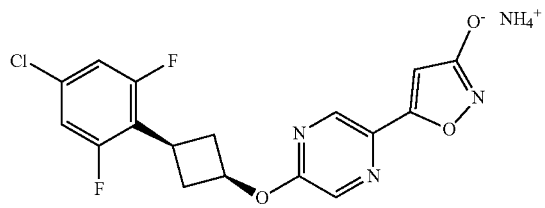 [SMILES: [NH4+] ; [O-]c1cc(-c2cnc(O[C@H]3C[C@@H](c4c(F)cc(Cl)cc4F)C3)cn2)on1] | ammonium 5-(5-{[cis-3-(4-chloro-2,6-difluorophenyl)-cyclobutyl]oxy}pyrazin-2-yl)isoxazol-3-olate | 380 |
| 50 | 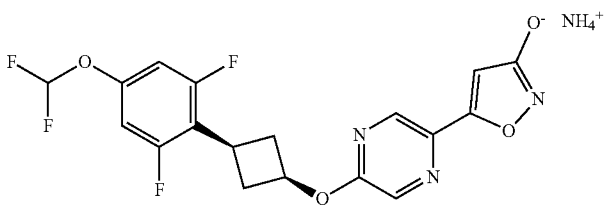 [SMILES: [NH4+] ; [O-]c1cc(-c2cnc(O[C@H]3C[C@@H](c4c(F)cc(OC(F)F)cc4F)C3)cn2)on1] | ammonium 5-[5-({cis-3-[4-(difluoromethoxy)-2,6-difluorophenyl]cyclobutyl}oxy)pyrazin-2-yl]isoxazol-3-olate | 412 |
| 51 | 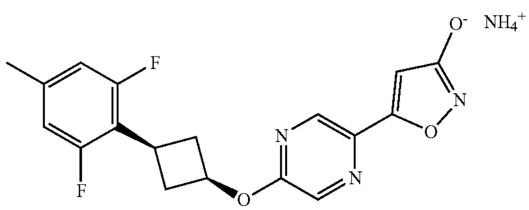 [SMILES: [NH4+] ; Cc1cc(F)c([C@H]2C[C@@H](Oc3cnc(-c4cc([O-])no4)cn3)C2)c(F)c1] | ammonium 5-(5-{[cis-3-(2,6-difluoro-4-methyl-phenyl)-cyclobutyl]oxy}pyrazin-2-yl)isoxazol-3-olate | 360 |
| 52 | 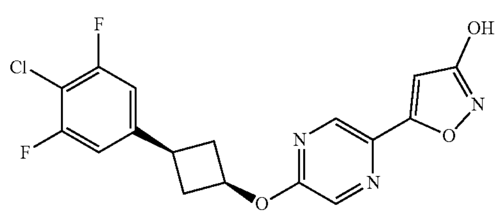 [SMILES: Oc1cc(-c2cnc(O[C@H]3C[C@@H](c4cc(F)c(Cl)c(F)c4)C3)cn2)on1] | 5-(5-{[cis-3-(4-chloro-3,5-difluorophenyl)cyclobutyl]oxy}pyrazin-2-yl)isoxazol-3-ol | 380 |
| 53 | 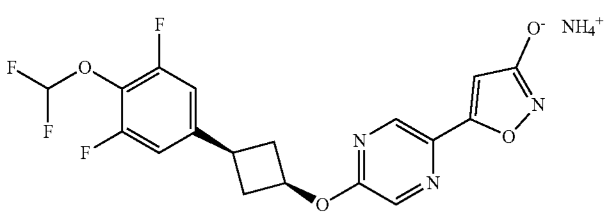 [SMILES: [O-]c1cc(-c2cnc(O[C@H]3C[C@@H](c4cc(F)c(OC(F)F)c(F)c4)C3)cn2)on1 ; [NH4+]] | ammonium 5-[5-({cis-3-[4-(difluoromethoxy)-3,5-difluorophenyl]cyclobutyl}oxy)pyrazin-2-yl]isoxazol-3-olate | 412 |
| 54 | 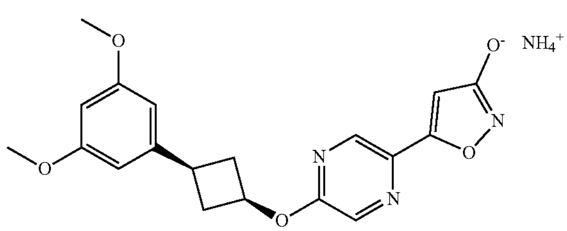 [SMILES: COc1cc(OC)cc([C@H]2C[C@@H](Oc3cnc(-c4cc([O-])no4)cn3)C2)c1 ; [NH4+]] | ammonium 5-(5-{[cis-3-(3,5-dimethoxyphenyl)cyclobutyl]oxy}pyrazin-2-yl)isoxazol-3-olate | 370 |

TABLE 1-continued

The compounds of Examples 14-60 were prepared from the appropriate previously described or commercially available starting materials using procedures similar to those in the Examples herein

| Example | Structure | Name | Exact Mass [M + H]+ |
|---|---|---|---|
| 55 | 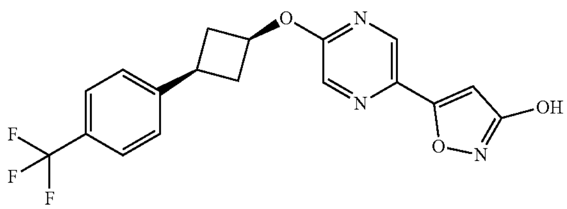 [SMILES: Oc1cc(-c2cnc(O[C@H]3C[C@@H](c4ccc(C(F)(F)F)cc4)C3)cn2)on1] | 5-[5-({cis-3-[4-(trifluoromethyl)phenyl] cyclo butyl}oxy)pyrazin-2-yl]isoxazol-3-ol | 378 |
| 56 | 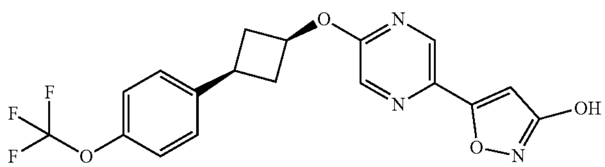 [SMILES: Oc1cc(-c2cnc(O[C@H]3C[C@@H](c4ccc(OC(F)(F)F)cc4)C3)cn2)on1] | 5-[5-({cis-3-[4-(trifluoromethoxy)phenyl] cyclobutyl}oxy)pyrazin-2-yl]isoxazol-3-ol | 394 |
| 57 | 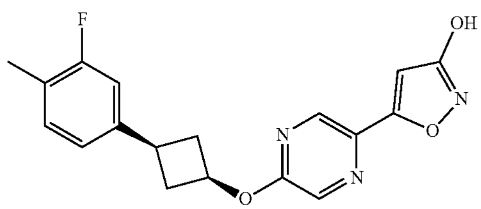 [SMILES: Cc1ccc([C@H]2C[C@@H](Oc3cnc(-c4cc(O)no4)cn3)C2)cc1F] | 5-(5-{[cis-3-(3-fluoro-4-methylphenyl)cyclobutyl] oxy}pyrazin-2-yl)isoxazol-3-ol | 342 |
| 58 | 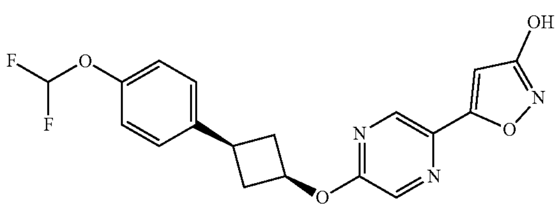 [SMILES: Oc1cc(-c2cnc(O[C@H]3C[C@@H](c4ccc(OC(F)F)cc4)C3)cn2)on1] | 5-[5-({cis-3-[4-(difluoromethoxy)phenyl] cyclobutyl}oxy)pyrazin-2-yl]isoxazol-3-ol | 376 |
| 59 | 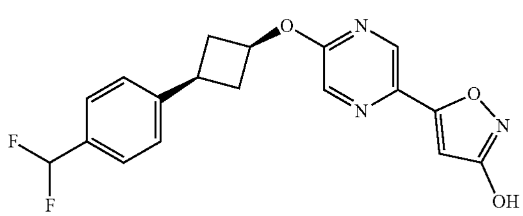 [SMILES: Oc1cc(-c2cnc(O[C@H]3C[C@@H](c4ccc(C(F)F)cc4)C3)cn2)on1] | 5-[5-({cis-3-[4-(difluoromethyl)phenyl] cyclo butyl}oxy)pyrazin-2-yl]isoxazol-3-ol | 360 |
| 60 | 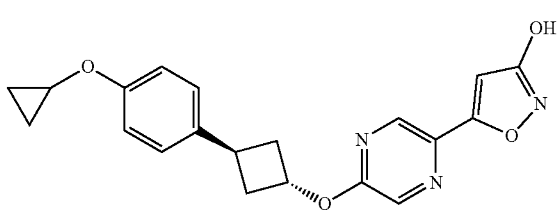 [SMILES: Oc1cc(-c2cnc(O[C@H]3C[C@H](c4ccc(OC5CC5)cc4)C3)cn2)on1] | 5-[5-({trans-3-[4-(cyclopropyloxyl)phenyl]cyclo butyl}oxy)pyrazin-2-yl]isoxazol-3-ol | 366 |

Example 61 sodium 5-[5-({trans-3-[3-(trifluoromethoxy)phenoxy]-cyclobutyl}oxy)pyrazin-2-yl]isoxazol-3-olate

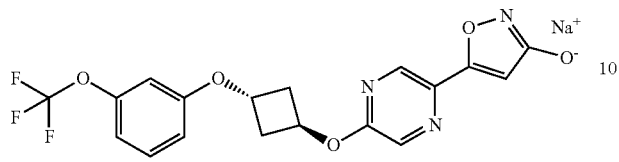

Step A: 1-{[trans-3-(benzyloxy)cyclobutyl]oxy}-3-(trifluoromethoxy)benzene. To a solution of 3-(trifluoromethoxy)phenol (1199 mg, 6.73 mmol), cis-3-(benzyloxy)cyclobutanol (800 mg, 4.49 mmol) and Ph$_3$P (1766 mg, 6.73 mmol) in THF (15 mL) was added dropwise DEAD (1.066 mL, 6.73 mmol) at 0° C. The resulting mixture was stirred at 35° C. under N$_2$ for 12 h, then poured into water (3 mL), extracted with EA (3×10 mL), dried over Na$_2$SO$_4$ and filtered. The filtrate was concentrated, and the resulting residue was purified by flash column (SiO$_2$, PE:EA=5:1) to give the title compound.

Step B: trans-3-[3-(trifluoromethoxy)phenoxy]cyclobutanol. To a solution of 1-{[trans-3-(benzyloxy)cyclobutyl]oxy}-3-(trifluoromethoxy)benzene (1.1 g, 3.25 mmol) in MeOH (20 mL) was added Pd-C(0.035 g, 0.325 mmol). The resulting mixture was stirred at 15° C. under H$_2$ (15 psi) for 2 h. Then the mixture was filtered, poured into water (5 mL), extracted with EA (3×10 mL), dried over Na$_2$SO$_4$, and filtered. The filtrate was concentrated to afford the title compound, which was used in the next step without further purification.

Step C: 2-[3-(methoxymethoxy)isoxazol-5-yl]-5-({trans-3-[3-(trifluoromethoxy)-phenoxy]cyclobutyl}oxy)pyrazine. To a solution of trans-3-[3-(trifluoromethoxy)phenoxy]-cyclobutanol (604 mg, 2.43 mmol) in THF (20 mL) was added 5-(5-bromopyrazin-2-yl)-3-(methoxymethoxy)isoxazole (580 mg, 2.027 mmol) and sodium 2-methylpropan-2-olate (487 mg, 5.07 mmol). The resulting mixture was stirred at 40° C. for 1 h, then poured into water (5 mL), extracted with EA (3×10 mL), dried over Na$_2$SO$_4$, and filtered. The filtrate was concentrated. Petroleum ether was added to the resulting residue and the mixture was stirred at 15° C. for 1 h, followed by filtration to give the title compound. MS (ESI) m/z: 454 [M+H]$^+$.

Step D: 5-[5-({trans-3-[3-(trifluoromethoxy)phenoxy]cyclobutyl}oxy)pyrazin-2-yl]-isoxazol-3-ol. To a solution of 2-[3-(methoxymethoxy)isoxazol-5-yl]-5-({trans-3-[3-(trifluoro-methoxy)phenoxy]-cyclobutyl}oxy)pyrazine (200 mg, 0.44 mmol) in THF (5 mL) was added 3M HCl (1 mL) to adjust the pH to pH 2-3. The resulting mixture was stirred at 40° C. for 1 h, then poured into water (5 mL), extracted with EA (3×10 mL), dried over Na$_2$SO$_4$, and filtered. The filtrate was concentrated. MeOH (10 mL) was added to the resulting residue and the mixture was stirred at 15° C. for 1 h. Then the mixture was filtered to give the title compound as the free form. The free form product was suspended in MeCN (10 mL), and then aqueous NaOH (0.48 mL, 1 g/50 mL water) was added to it dropwise. The mixture was freeze-dried to afford the title compound. $^1$H NMR (400 MHz, CD$_3$OD) δ 8.49 (d, J=0.66 Hz, 1H), 8.24 (d, J=0.88 Hz, 1H), 7.35 (t, J=8.27 Hz, 1H), 6.85 (dd, J=1.65, 8.27 Hz, 2H), 6.74 (m, 1H), 6.18 (s, 1H), 5.48 (q, J=5.95 Hz, 1H), 4.99 (q, J=5.40 Hz, 1H), 2.67-2.74 (m, 4H). MS (ESI) m/z: 410.0 [M+H]$^+$.

Example 62

2-({cis-3-[(3,4-difluorobenzyl)oxy]cyclobutyl}oxy)-5-(3-hydroxy-isoxazol-5-yl)pyridinium trifluoroacetate

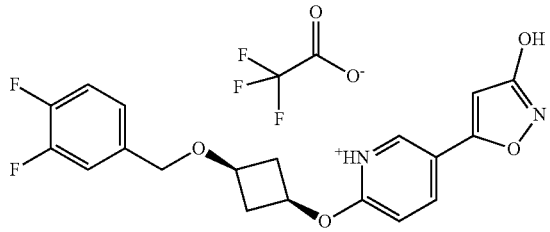 [SMILES: Oc1cc(-c2ccc(O[C@H]3C[C@@H](OCc4ccc(F)c(F)c4)C3)[nH+]c2)on1 ; O=C([O-])C(F)(F)F]

Step A: cis-3-((tert-butyldimethylsilyl)oxy)cyclobutan-1-ol. To a solution of 3-((tert-butyl-dimethylsilyl)oxy)cyclobutanone (5.05 g, 25.2 mmol) in methanol (50 mL) at 0° C. under N$_2$ was added NaBH$_4$ (1.060 g, 27.7 mmol). The reaction mixture was stirred at 0° C. under N$_2$. After 1 h, the reaction mixture was quenched by addition of saturated aqueous NaHCO$_3$ (50 mL) at 0° C. The mixture was stirred at rt for 30 min, then concentrated under vacuum and extracted with EtOAc (3×50 mL). The combined EtOAc extracts were dried over Na$_2$SO$_4$, filtered and concentrated. The resulting residue was purified by column chromatography using EtOAc/hexanes as eluents (RediSep Gold 120 g HP silica gel) to yield the title compound.

Step B: 5-(6-(cis-3-((tert-butyldimethylsilyl)oxy)cyclobutoxy)pyridin-3-yl)-3-(methoxy-methoxy)isoxazole. To a solution of cis-3-((tert-butyldimethylsilyl)oxy)cyclobutanol (1.850 g, 9.14 mmol) and 5-(6-chloropyridin-3-yl)-3-(methoxymethoxy)isoxazole (2 g, 8.31 mmol) in DMF (30 mL) at 0° C. was added NaH (0.399 g, 9.97 mmol). The reaction mixture was allowed to warm slowly to rt and stirred overnight. The reaction mixture was quenched by addition of saturated NaHCO$_3$ (50 mL), then diluted with H$_2$O (50 mL) and extracted with EtOAc (2×50 mL). The organic extracts were combined, washed with H$_2$O (4×50 mL), dried over Na$_2$SO$_4$, filtered and concentrated. The resulting residue was purified by column chromatography using EtOAc/hexanes as eluents (RediSep Gold 80 g HP silica gel) to yield the title compound.

Step C: cis-3-((5-(3-(methoxymethoxy)isoxazol-5-yl)pyridin-2-yl)oxy)cyclobutan-1-ol. To a solution of 5-(6-(cis-3-((tert-butyldimethylsilyl)oxy)cyclobutoxy)pyridin-3-yl)-3-(methoxy-methoxy)isoxazole (1.27 g, 3.12 mmol) in THF (15 mL) was added TBAF (3.75 ml, 3.75 mmol) (1 M solution in THF) at rt. The reaction mixture was stirred at rt for 2 h, then diluted with EtOAc (50 mL) and washed with saturated NaHCO$_3$ (1×50 mL), brine (1×50 mL), dried over Na$_2$SO$_4$, and filtered. The filtrate was concentrated, and the resulting residue was purified by column chromatography using EtOAc/hexanes as eluents (RediSep Gold 40 g HP silica gel) to afford the title compound.

Step D: 5-(6-(cis-3-((3,4-difluorobenzyl)oxy)cyclobutoxy)pyridin-3-yl)-3-(methoxymethoxy)-isoxazole. To an 8 mL reaction vial with 3,4-difluorobenzyl bromide (14.91 mg, 0.137 mmol) in a glove box was added a solution of cis-3-((5-(3-(methoxymethoxy)isoxazol-5-yl)-pyridin-2-yl)

oxy)-cyclobutanol (20 mg, 0.068 mmol) in DMF (1 mL). The reaction mixture was treated with NaH (3.28 mg, 0.082 mmol) in a glove box at rt. The vial was sealed and the reaction mixture was stirred at rt under $N_2$ overnight. Then the reaction mixture was quenched by the addition of 1N aq. HCl (200 µL) and stirred at rt for 10 min. The reaction mixture was concentrated to afford the title compound, which was used in the next step without further purification.

Step E: 2-({cis-3-[(3,4-difluorobenzyl)oxy] cyclobutyl}oxy)-5-(3-hydroxy-isoxazol-5-yl)-pyridinium trifluoroacetate. To a solution of 5-(5-((cis-3-(4-bromophenyl)cyclobutoxy)-pyrazin-2-yl)-3-(methoxymethoxy)isoxazole from Step E (20 mg, 0.068 mmol) in THF (1 mL) and MeOH (250 µL) was added a solution of HCl (116 µL, 0.463 mmol) (4 M in dioxane) at rt. The reaction mixture was stirred at rt for 1 h, then concentrated. The resulting residue was purified by prep-HPLC (TFA modifier) to afford the title compound. $^1$H NMR (500 MHz, DMSO-$d_6$) δ 8.60 (d, J=2.5 Hz, 1H), 8.08 (dd, J=8.7, 2.5 Hz, 1H), 7.37-7.42 (m, 2H), 7.20 (m, 1H), 6.94 (d, J=8.7 Hz, 1H), 6.52 (s, 1H), 4.83-4.89 (m, 1H), 4.39 (s, 2H), 3.81-3.86 (m, 1H), 2.82-2.87 (m, 2H), 1.98-2.03 (m, 2H). MS (ESI) m/z: 375.2 [M+H]$^+$.

Example 63 ammonium 5-(5-{[cis-3-(3-chloro-4-fluorophenoxy) cyclobutyl]-oxy}pyrazin-2-yl)isoxazol-3-olate

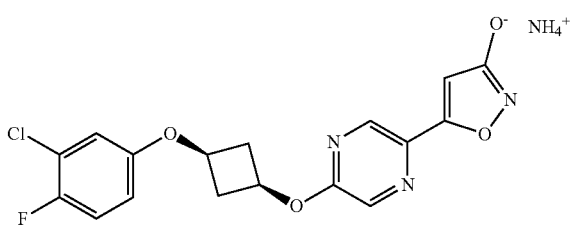 [SMILES: [O-]c1cc(-c2cnc(O[C@H]3C[C@@H](Oc4ccc(F)c(Cl)c4)C3)cn2)on1 ; [NH4+]]

Step A: 5-(5-(cis-3-((tert-butyldimethylsilyl)oxy)cyclobutoxy)pyrazin-2-yl)-3-(methoxy-methoxy)isoxazole. To a solution of cis-3-((tert-butyldimethylsilyl)oxy)cyclobutanol (5.17 g, 25.5 mmol) in DMF (80 ml) at 0° C. was added NaH (1.174 g, 29.4 mmol). The reaction mixture was stirred at 0° C. under $N_2$ for 10 min. Then a solution of 5-(5-bromopyrazin-2-yl)-3-(methoxy-methoxy)isoxazole (4 g, 13.98 mmol) in DMF (20 mL) was added dropwise to the reaction mixture at 0° C. The reaction mixture was stirred at 0° C. under $N_2$ for 5 min, at rt for 1 h, and then quenched by the addition of saturated NaHCO$_3$ (50 mL). The reaction mixture was diluted with H$_2$O (100 mL) and extracted with EtOAc (3×100 mL). The combined organic layers were washed with H$_2$O (4×100 mL), dried over Na$_2$SO$_4$, filtered and concentrated to afford the title compound, which was used in the next step without further purification.

Step B: cis-3-((5-(3-(methoxymethoxy)isoxazol-5-yl) pyrazin-2-yl)oxy)cyclobutan-1-ol. To a solution of 5-(5-(cis-3-((tert-butyldimethylsilyl)oxy)cyclobutoxy)pyrazin-2-yl)-3-(methoxy-methoxy)isoxazole (5.70 g, 13.98 mmol) from Step A in THF (80 mL) was added a solution of TBAF (28.0 ml, 28.0 mmol, 1 M solution in THF) at rt. The reaction mixture was stirred at rt for 1 h, then concentrated and diluted with EtOAc (100 mL) and saturated NaHCO$_3$ (100 mL). The layers were separated and the aqueous layer was extracted with CH$_2$Cl$_2$ (3×100 mL). The combined organic layers were dried over Na$_2$SO$_4$, filtered and concentrated. The resulting residue was purified by column chromatography using EtOAc/dichloromethane as eluents (RediSep Gold 330 g HP silica gel) to afford the title compound.

Step C: trans-3-((5-(3-(methoxymethoxy)isoxazol-5-yl) pyrazin-2-yl)oxy)cyclobutyl benzoate. To a solution of triphenylphosphine (1.341 g, 5.11 mmol) in THF (10 mL) was added DIAD (0.994 mL, 5.11 mmol). The reaction mixture was stirred vigorously until it solidified, then, the reaction mixture was treated with a solution of cis-3-((5-(3-(methoxymethoxy)isoxazol-5-yl)-pyrazin-2-yl)oxy)cyclobutanol (1 g, 3.41 mmol) and benzoic acid (0.625 g, 5.11 mmol) in THF (25 ml). The reaction mixture was stirred at rt overnight, then concentrated, diluted with EtOAc (50 mL), washed with saturated NaHCO$_3$ (2×50 mL), brine (1×50 mL), dried over Na$_2$SO$_4$, and filtered. The filtrate was concentrated, and the resulting residue was purified by column chromatography using EtOAc/hexanes (RediSep Gold 80 g HP silica gel) to afford the title compound.

Step D: trans-3-((5-(3-(methoxymethoxy)isoxazol-5-yl) pyrazin-2-yl)oxy)cyclobutan-1-ol. To a suspension of trans-3-((5-(3-(methoxymethoxy)isoxazol-5-yl)pyrazin-2-yl)oxy) cyclobutyl benzoate (1.1 g, 2.77 mmol) in THF (40 ml) and MeOH (10 mL) was added a solution of NaOH (13.84 ml, 13.84 mmol, 1M in H$_2$O) at rt. The reaction mixture was stirred at rt for 1 h, then concentrated to remove most of the solvent, and diluted with H$_2$O and saturated NaHCO$_3$ (pH of the suspension became pH ~9). The resulting mixture was extracted with EtOAc (3×50 mL). The combined organic extracts were dried over Na$_2$SO$_4$, and filtered. The filtrate was concentrated, and the resulting residue was purified by column chromatography using EtOAc/hexanes as eluents (RediSep Gold 80 g HP silica gel) to yield the title compound.

Step E: 5-(5-(cis-3-(3-chloro-4-fluorophenoxy)cyclobutoxy)pyrazin-2-yl)-3-(methoxy-methoxy)-isoxazole. To a solution of trans-3-((5-(3-(methoxymethoxy)isoxazol-5-yl)-pyrazin-2-yl)oxy)cyclobutanol (150 mg, 0.511 mmol) in 1,4-dioxane (3 ml) were added 3-chloro-4-fluorophenol (150 mg, 1.023 mmol) and cyanomethylenetributylphosphorane (0.424 mL, 1.534 mmol). The reaction mixture was heated at 80° C. overnight. Then the reaction mixture was cooled to rt, quenched by addition of MeOH (5 mL), and stirred at rt under $N_2$ for 10 min. The reaction mixture was concentrated, and the resulting residue was purified by column chromatography using EtOAc/hexanes as eluents (RediSep Gold 24 g HP silica gel) to yield the title compound.

Step F: ammonium 5-(5-{[cis-3-(3-chloro-4-fluorophenoxy)cyclobutyl]oxy}-pyrazin-2-yl)-isoxazol-3-olate. To a solution of 5-(5-(cis-3-(3-chloro-4-fluorophenoxy)cyclobutoxy)-pyrazin-2-yl)-3-(methoxymethoxy)isoxazole (20 mg, 0.068 mmol) in THF (1 mL) and MeOH (250 µL) was added a solution of HCl (170 µL, 0.68 mmol, 4 M in dioxane) at rt. The reaction mixture was stirred at rt for 1 h, then concentrated. The resulting residue was purified by prep HPLC (NH$_4$OH modifier) to yield the title compound. $^1$H NMR (500 MHz, DMSO-$d_6$) δ 8.70 (s, 1H), 8.43 (s, 1H), 7.35 (t, J=9.1 Hz, 1H), 7.12 (dd, J=6.1, 3.0 Hz, 1H), 6.91 (dt, J=9.1, 3.4 Hz, 1H), 6.54 (s, 1H), 4.97-5.03 (m, 1H), 4.55-4.60 (m, 1H), 3.16 (m, 2H), 2.22 (m, 2H). MS (ESI) m/z: 378.1 [M+H]$^+$.

Example 64 ammonium 5-{6-[(3-phenoxycyclobutyl)methoxy]pyridin-3-yl}isoxazol-3-olate

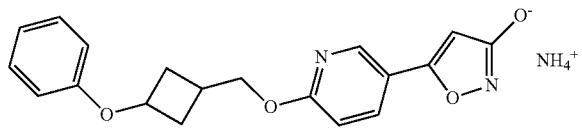 [SMILES: [O-]c1cc(-c2ccc(OCC3CC(Oc4ccccc4)C3)nc2)on1 ; [NH4+]]

Step A: 3-(methoxymethoxy)-5-(6-((3-phenoxycyclobutyl)methoxy)pyridin-3-yl)isoxazole. To a solution of (3-phenoxycyclobutyl)methanol (51.8 mg, 0.291 mmol) in THF (2 mL) was added sodium hydride (21 mg, 0.873 mmol) portionwise. The reaction was stirred at r.t. for 10 min, then a solution of 5-(6-chloropyridin-3-yl)-3-(methoxymethoxy)isoxazole (70 mg, 0.291 mmol) in THF (1 mL) was added. The reaction mixture was stirred at r.t. overnight, then quenched with H$_2$O and extracted with EA. The combined organic layers were dried over Na$_2$SO$_4$, filtered and concentrated to afford the title compound, which was used without further purification in the next step. MS (ESI) m/z: 383 [M+H]$^+$.

Step B: ammonium 5-{6-[(3-phenoxycyclobutyl)methoxy]pyridin-3-yl}isoxazol-3-olate. To a solution of 3-(methoxymethoxy)-5-(6-((3-phenoxycyclobutyl)methoxy)pyridin-3-yl)-isoxazole (111 mg, 0.291 mmol) in MeOH (1 mL) was added 4N HCl in dioxane (1 mL, 4 mmol). Then the mixture was stirred at r.t. for 1 h. Then the reaction was concentrated and the resulting residue was purified by prep-HPLC (NH$_4$OH modifier) to afford the title compound. $^1$H NMR (500 MHz, Acetone-d$_6$) δ 2.05-1.99 (2H, m), 2.58-2.49 (1H, m), 2.72-2.66 (2H, m), 4.43 (2H, d, J=6.2 Hz), 4.72-4.66 (1H, m), 6.45 (1H, s), 6.95-6.87 (4H, m), 7.29-7.26 (2H, m), 8.07 (1H, dd, J=8.7, 2.5 Hz), 8.61 (1H, dd, J=2.5, 0.8 Hz). MS (ESI) m/z: 339 [M+H]$^+$.

Example 65 sodium 5-[5-({cis-3-[(4-fluorophenoxy)methyl]cyclobutyl}oxy)pyrazin-2-yl]isoxazol-3-olate

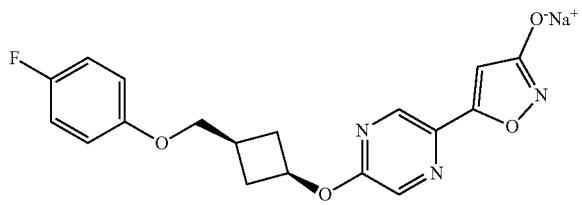

Step A: tert-butyl(cis-3-((4-fluorophenoxy)methyl)cyclobutoxy)dimethylsilane. To a solution of (cis-3-((tert-butyldimethylsilyl)oxy)cyclobutyl)methanol (3.86 g, 17.8 mmol) and 4-fluorophenol (2.00 g, 17.8 mmol) in CH$_2$Cl$_2$ (60 mL) at 0° C. was added polymer bound PPh$_3$ (3 mmol/g, 11.9 g, 35.7 mmol) followed by di-tert-butyl diazene-1,2-dicarboxylate (6.16 g, 26.8 mmol). The reaction mixture was stirred at ambient temperature for 5 h, then the resulting solid was filtered off and the filtrate was concentrated. Then hexanes were added and the resulting solid was filtered off again. The filtrated was concentrated and the resulting residue was purified by silica column chromatography, eluting with 0-10% EtOAc in hexanes, to afford the title compound. MS (ESI) m/z: 311 [M+H]$^+$.

Step B: cis-3-((4-fluorophenoxy)methyl)cyclobutan-1-ol. To tert-butyl(cis-3-((4-fluoro-phenoxy)methyl)cyclobutoxy)dimethylsilane (3.38 g, 10.9 mmol) in THF (40 ml) at ambient temperature was added 1 M TBAF in THF (11.4 mL, 11.4 mmol). The reaction mixture was stirred at ambient temperature for 1.5 h, then the volatiles were removed under vacuum, followed by the addition of ethyl acetate (50 mL) and water (40 mL). The aqueous layer was extracted with ethyl acetate (40 mL), and the combined organic layers were dried over Na$_2$SO$_4$, and filtered. The filtrate was concentrated, and purified via silica column chromatography, eluting with 0-40 then 40% EtOAc in hexanes to afford the title compound. MS (ESI) m/z: 197 [M+H]$^+$.

Step C: 5-(5-(cis-3-((4-fluorophenoxy)methyl)cyclobutoxy)pyrazin-2-yl)-3-(methoxy-methoxy)isoxazole. To cis-3-((4-fluorophenoxy)methyl)cyclobutan-1-ol (1.94 g, 9.89 mmol) in DMF (40 mL) at ambient temperature was added sodium hydride (60%, 0.435 g, 10.9 mmol) in portions. After 15 min, 5-(5-bromopyrazin-2-yl)-3-(methoxymethoxy)isoxazole (2.83 g, 9.89 mmol) was added. The reaction flask was dipped into room temperature water bath to cool the reaction. The reaction mixture was stirred at rt for 5 h then put in refrigerator overnight. Then water (120 ml) was added and the reaction mixture was extracted with a mixture of ether (150 ml) and EtOAc (50 ml). The aqueous layer was separated, and extracted with a mixture of ether (100 ml) and EtOAc (30 ml). The combined organic layers were dried over Na$_2$SO$_4$, and filtered. The filtrate was concentrated, and the solid was recrystallized from EtOAc/ether to afford the title compound. MS (ESI) m/z: 402 [M+H]$^+$.

Step D: Sodium 5-[5-({cis-3-[(4-fluorophenoxy)methyl]cyclobutyl}oxy)pyrazin-2-yl]-isoxazol-3-olate. To a solution of 5-(5-(cis-3-((4-fluorophenoxy)methyl)cyclobutoxy)-pyrazin-2-yl)-3-(methoxymethoxy)isoxazole (1.64 g, 4.09 mmol) in methanol (20 mL) and CH$_2$Cl$_2$ (20 mL) at ambient temperature was added 4M hydrogen chloride in dioxane (8.17 mL, 32.7 mmol). The reaction mixture was stirred at rt for 1 h, then cooled in a refrigerator for 1 h. The resulting solid was collected by filtration, and dried under reduced pressure. To the resulting residue was added CH$_3$CN (30 ml) followed by 1 M sodium hydroxide (33.0 ml, 3.3 mmol). After filtration of the resulting cloudy solution, it was lyophilized overnight to afford the title compound. MS (ESI) m/z: 358 [M+H]$^+$. $^1$H NMR (500 MHz, DMSO-d$_6$) δ 8.38 (d, J=1.4 Hz, 1H), 8.27 (d, J=1.4 Hz, 1H), 7.15-7.06 (m, 2H), 7.00-6.92 (m, 2H), 5.78 (s, 1H), 5.15 (m, 1H), 3.99 (d, J=6.0 Hz, 2H), 2.66-2.57 (m, 2H), 2.43 (m, 1H), 2.00 (m, 2H).

TABLE 2

The compounds of Examples 66-85 were prepared from the appropriate previously described or commercially available starting materials using procedures similar to those in the Examples herein

| Example | Structure | Name | Exact Mass [M + H]+ |
|---|---|---|---|
| 66 | 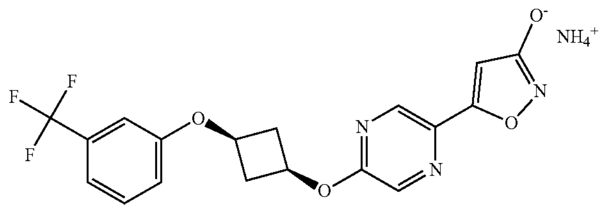 [SMILES: [O-]c1cc(-c2cnc(O[C@H]3C[C@@H](Oc4cccc(C(F)(F)F)c4)C3)cn2)on1 ; [NH4+]] | ammonium 5-[5-({cis-3-[3-(trifluoromethyl)phenoxy]cyclobutyl}oxy)pyrazin-2-yl]isoxazol-3-olate | 394 |
| 67 | 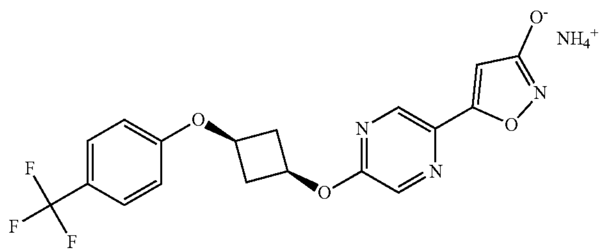 [SMILES: [O-]c1cc(-c2cnc(O[C@H]3C[C@@H](Oc4ccc(C(F)(F)F)cc4)C3)cn2)on1 ; [NH4+]] | ammonium 5-[5-({cis-3-[4-(trifluoromethyl)phenoxy]cyclobutyl}oxy)pyrazin-2-yl]isoxazol-3-olate | 394 |
| 68 | 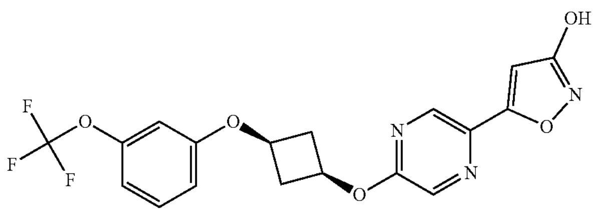 [SMILES: Oc1cc(-c2cnc(O[C@H]3C[C@@H](Oc4cccc(OC(F)(F)F)c4)C3)cn2)on1] | 5-[5-({cis-3-[3-(trifluoromethoxy)phenoxy]cyclobutyl}oxy)pyrazin-2-yl]isoxazol-3-ol | 410 |
| 69 | 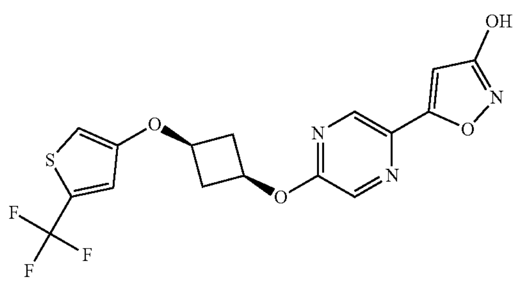 [SMILES: Oc1cc(-c2cnc(O[C@H]3C[C@@H](Oc4csc(C(F)(F)F)c4)C3)cn2)on1] | 5-{5-[(cis-3-{[5-(trifluoromethyl)thiophen-3-yl]oxy}cyclobutyl)oxy]pyrazin-2-yl}isoxazol-3-ol | 400 |
| 70 | 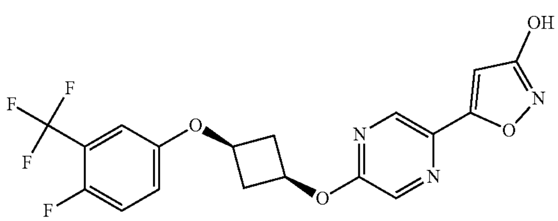 [SMILES: Oc1cc(-c2cnc(O[C@H]3C[C@@H](Oc4ccc(F)c(C(F)(F)F)c4)C3)cn2)on1] | 5-[5-({cis-3-[4-fluoro-3-(trifluoromethyl)phenoxy]cyclobutyl}oxy)pyrazin-2-yl]isoxazol-3-ol | 412 |
| 71 | 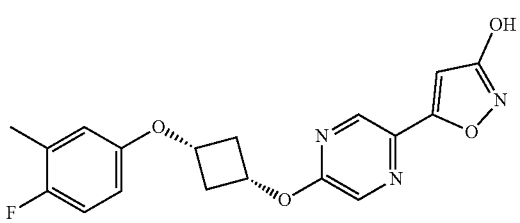 [SMILES: Cc1cc(O[C@H]2C[C@@H](Oc3cnc(-c4cc(O)no4)cn3)C2)ccc1F] | 5-(5-{[cis-3-(4-fluoro-3-methylphenoxy)cyclobutyl]oxy}pyrazin-2-yl)isoxazol-3-ol | 358 |

TABLE 2-continued

The compounds of Examples 66-85 were prepared from the appropriate previously described or commercially available starting materials using procedures similar to those in the Examples herein

| Example | Structure | Name | Exact Mass [M + H]+ |
|---|---|---|---|
| 72 | 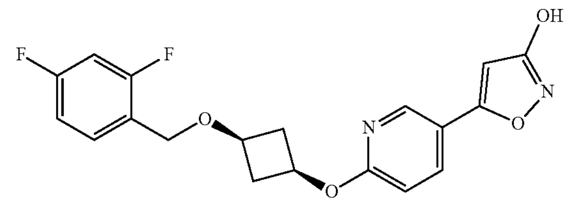 [SMILES: Oc1cc(-c2ccc(O[C@H]3C[C@@H](OCc4ccc(F)cc4F)C3)nc2)on1] | 5-[6-({cis-3-[(2,4-difluorobenzyl)oxy]cyclobutyl}oxy)pyridin-3-yl]isoxazol-3-ol (mixture of isomers predominantly cis) | 375 |
| 73 | 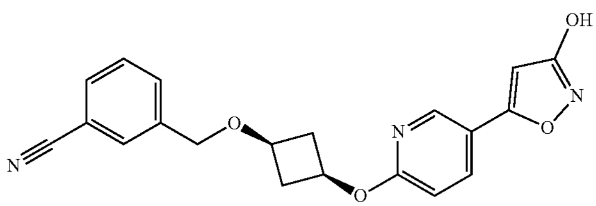 [SMILES: N#Cc1cccc(CO[C@H]2C[C@@H](Oc3ccc(-c4cc(O)no4)cn3)C2)c1] | 3-{[(cis-3-{[5-(3-hydroxyisoxazol-5-yl)pyridin-2-yl]oxy}cyclobutyl)oxy]methyl}benzonitrile (mixture of isomers predominantly cis) | 364 |
| 74 | 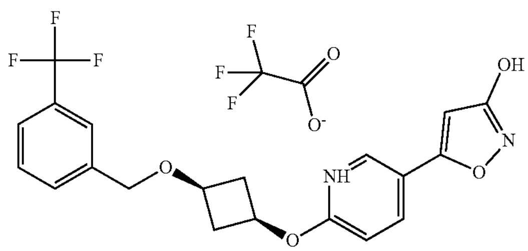 [SMILES: Oc1cc(-c2ccc(O[C@H]3C[C@@H](OCc4cccc(C(F)(F)F)c4)C3)nc2)on1 ; O=C([O-])C(F)(F)F] | 5-(3-hydroxyisoxazol-5-yl)-2-[(cis-3-{[3-(trifluoromethyl)benzyl]oxy}cyclobutyl)oxy]pyridinium trifluoroacetate | 407 |
| 75 | 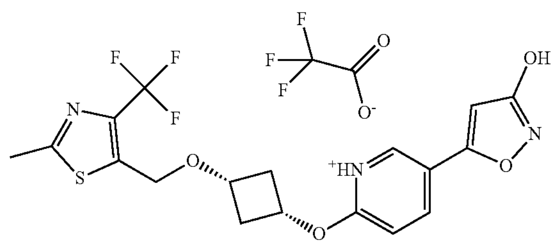 [SMILES: Cc1nc(C(F)(F)F)c(CO[C@H]2C[C@@H](Oc3ccc(-c4cc(O)no4)c[nH+]3)C2)s1 ; O=C([O-])C(F)(F)F] | 5-(3-hydroxyisoxazol-5-yl)-2-[(cis-3-{[2-methyl-4-(trifluoromethyl)-1,3-thiazol-5-yl]methoxy}cyclobutyl)oxy]pyridinium trifluoroacetate | 428 |
| 76 | 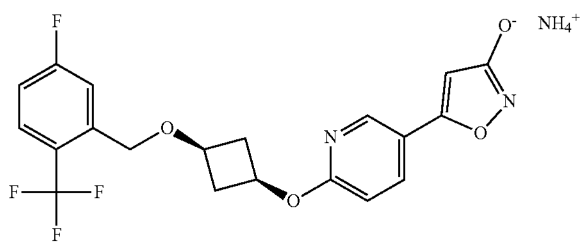 [SMILES: [O-]c1cc(-c2ccc(O[C@H]3C[C@@H](OCc4cc(F)ccc4C(F)(F)F)C3)nc2)on1 ; [NH4+]] | ammonium 5-{6-[(cis-3-{[5-fluoro-2-(trifluoromethyl)benzyl]oxy}cyclobutyl)oxy]pyridin-3-yl}isoxazol-3-olate (mixture of isomers predominantly cis) | 425 |
| 77 | 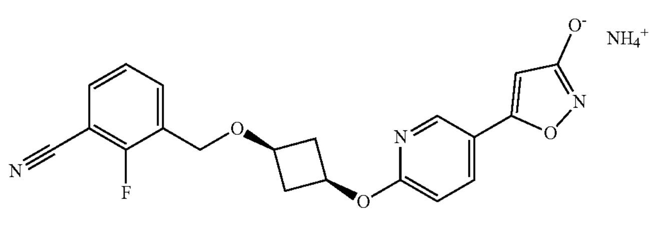 [SMILES: N#Cc1cccc(CO[C@H]2C[C@@H](Oc3ccc(-c4cc([O-])no4)cn3)C2)c1F ; [NH4+]] | ammonium 5-[6-({cis-3-[(3-cyano-2-fluorobenzyl)oxy]cyclobutyl}oxy)pyridin-3-yl]isoxazol-3-olate (mixture of isomers predominantly cis) | 382 |

TABLE 2-continued

The compounds of Examples 66-85 were prepared from the appropriate previously described or commercially available starting materials using procedures similar to those in the Examples herein

| Example | Structure | Name | Exact Mass [M + H]+ |
|---|---|---|---|
| 78 | 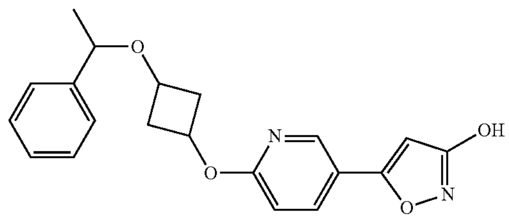 [SMILES: CC(OC1CC(Oc2ccc(-c3cc(O)no3)cn2)C1)c1ccccc1] | 5-(6-{[3-(1-phenylethoxy)cyclobutyl]oxy}pyridin-3-yl)isoxazol-3-ol (mixture of isomers) | 353 |
| 79 | 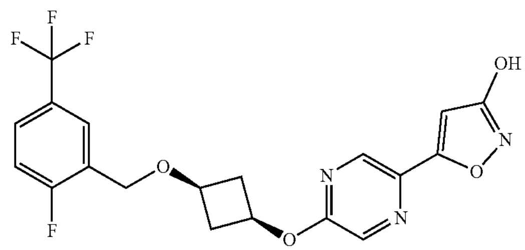 [SMILES: Oc1cc(-c2cnc(O[C@H]3C[C@@H](OCc4cc(C(F)(F)F)ccc4F)C3)cn2)on1] | 5-{5-[(cis-3-{[2-fluoro-5-(trifluoromethyl)benzyl]oxy}cyclobutyl)oxy]pyrazin-2-yl}isoxazol-3-ol (mixture of isomers predominantly cis) | 426 |
| 80 | 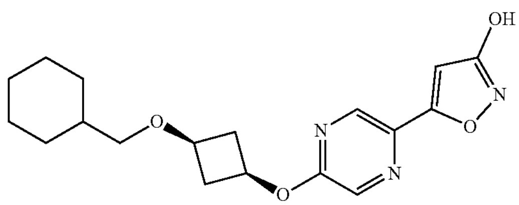 [SMILES: Oc1cc(-c2cnc(O[C@H]3C[C@@H](OCC4CCCCC4)C3)cn2)on1] | 5-(5-{[cis-3-(cyclohexylmethoxy)cyclobutyl]oxy}pyrazin-2-yl)isoxazol-3-ol (mixture of isomers predominantly cis) | 346 |
| 81 | 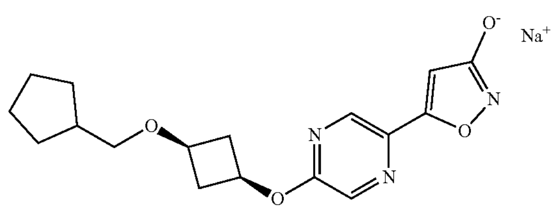 [SMILES: [O-]c1cc(-c2cnc(O[C@H]3C[C@@H](OCC4CCCC4)C3)cn2)on1 ; [Na+]] | sodium 5-(5-{[cis-3-(cyclopentylmethoxy)cyclobutyl]oxy}pyrazin-2-yl)isoxazol-3-olate (mixture of isomers predominantly cis) | 332 |
| 82 | 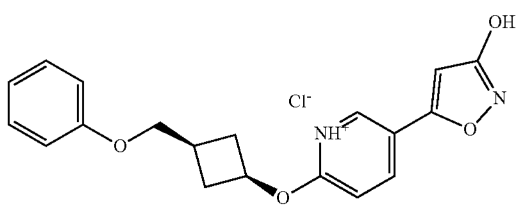 [SMILES: Oc1cc(-c2ccc(O[C@H]3C[C@@H](COc4ccccc4)C3)[nH+]c2)on1 ; [Cl-]] | 5-(3-hydroxyisoxazol-5-yl)-2-{[cis-3-(phenoxymethyl)cyclobutyl]oxy}pyridinium chloride | 339 |
| 83 | 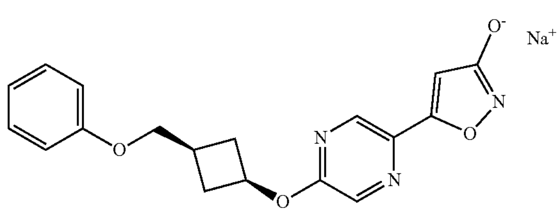 [SMILES: [O-]c1cc(-c2cnc(O[C@H]3C[C@@H](COc4ccccc4)C3)cn2)on1 ; [Na+]] | sodium 5-(5-{[cis-3-(phenoxymethyl)cyclobutyl]oxy}pyrazin-2-yl)isoxazol-3-olate | 340 |
| 84 | 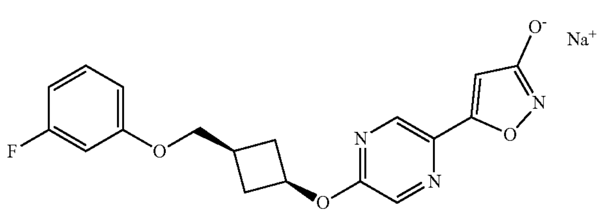 [SMILES: [O-]c1cc(-c2cnc(O[C@H]3C[C@@H](COc4cccc(F)c4)C3)cn2)on1 ; [Na+]] | sodium 5-[5-({cis-3-[(3-fluorophenoxy)methyl]cyclobutyl}oxy)pyrazin-2-yl]isoxazol-3-olate | 358 |

TABLE 2-continued

The compounds of Examples 66-85 were prepared from the appropriate previously described or commercially available starting materials using procedures similar to those in the Examples herein

| Example | Structure | Name | Exact Mass [M + H]+ |
|---|---|---|---|
| 85 | 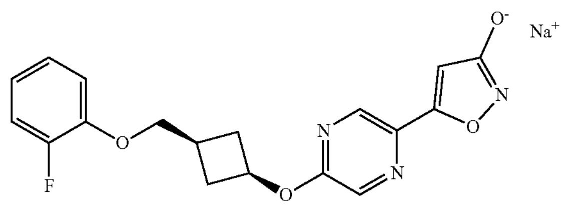 [SMILES: [O-]c1cc(-c2cnc(O[C@H]3C[C@@H](COc4ccccc4F)C3)cn2)on1 ; [Na+]] | sodium 5-[5-({cis-3-[(2-fluorophenoxy)methyl]cyclobutyl}oxy)pyrazin-2-yl]isoxazol-3-olate | 358 |

Example 86 sodium 5-(6-{[cis-3-(2-ethoxypyridin-4-yl)-3-fluoro-cyclobutyl]oxy}pyridin-3-yl)isoxazol-3-olate

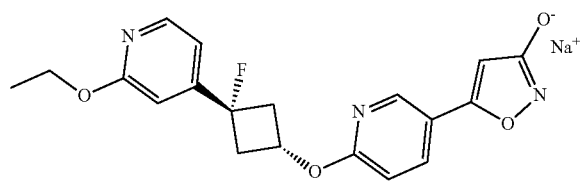 [SMILES: CCOc1cc([C@]2(F)C[C@@H](Oc3ccc(-c4cc([O-])no4)cn3)C2)ccn1 ; [Na+]]

Step A: 3-{[tert-butyl(dimethyl)silyl]oxy}-1-(2-ethoxypyridin-4-yl)cyclobutanol. To a solution of 4-bromo-2-ethoxypyridine (2.64 g, 13.07 mmol) in toluene (65.3 mL) was added nBuLi (1.6 M in Hexanes, 9.80 mL, 15.68 mmol) dropwise at −78° C. The mixture was stirred at −78° C. for 40 min, then 3-{[tert-butyl(dimethyl)silyl]oxy}cyclobutanone (3.40 g, 16.99 mmol) was added dropwise. The reaction mixture was stirred at −78° C. for 1 h, then warmed to 0° C. and quenched with saturated aqueous NH₄Cl. (15 mL). The mixture was extracted with EtOAc (3×10 mL), and the combined organic phase was washed with brine, dried over Na₂SO₄, and filtered. The filtrate was concentrated, and the resulting residue was purified by flash column chromatography on silica gel (ISCO 40 g SiO₂ column, eluting with 0-40% EtOAc/hexanes) to afford the title compound.

Step B: 3-(2-ethoxypyridin-4-yl)-3-fluorocyclobutanol. Diethylaminosulfur trifluoride (1.715 mL, 12.98 mmol) was added to a solution of 3-{[tert-butyl(dimethyl)silyl]oxy}-1-(2-ethoxy-pyridin-4-yl)cyclobutanol (2.1 g, 6.49 mmol) in CH₂Cl₂ (32.5 mL) at −78° C. After stirring for 30 min, the mixture was diluted with water, and extracted with CH₂Cl₂ (3×10 mL). The combined organic layers were washed with brine, dried over Na₂SO₄, and filtered. The filtrate was concentrated, and the resulting residue was purified by flash column chromatography on silica gel (ISCO 40 g column, eluting with EtOAc/hexane (0-80% EtOAc in hexane) to afford the title compound.

Step C: 2-ethoxy-4-[cis-1-fluoro-3-({5-[3-(methoxymethoxy)isoxazol-5-yl]pyridin-2-yl}-oxy)cyclobutyl]pyridine. Into a flask was added 3-(2-ethoxypyridin-4-yl)-3-fluorocyclobutanol (550 mg, 2.60 mmol) in THF (10 mL), followed by the portionwise addition of NaH (312 mg, 7.81 mmol). The reaction was stirred at rt for 15 min, then a solution of 2-chloro-5-[3-(methoxy-methoxy)isoxazol-5-yl]pyridine (627 mg, 2.60 mmol) in THF(1 mL) was added. The reaction mixture was stirred at 50° C. for 30 min, then quenched with water, and extracted with EtOAc (2×15 mL). The organic layer was collected and dried over Na₂SO₄, and filtered. The filtrate was removed under reduced pressure. The resulting residue was purified by flash column chromatography on silica gel (ISCO 80 g column, eluting with EtOAc/hexane (0-80% EtOAc in hexanes) to afford the title compound.

Step D: 5-(6-{[cis-3-(2-ethoxypyridin-4-yl)-3-fluorocyclobutyl]oxy}pyridin-3-yl)isoxazol-3-ol. To a solution of 2-ethoxy-4-[cis-1-fluoro-3-({5-[3-(methoxymethoxy)isoxazol-5-yl]pyridin-2-yl}oxy)cyclobutyl]pyridine (210 mg, 0.506 mmol) in DCM (3159 μL) was added HCl in dioxane (4.0 M, 1264 μL, 5.06 mmol). The mixture was stirred at r.t. overnight. Then the reaction was concentrated and the resulting residue was purified by reverse phase column chromatography to give the title compound.

Step E: sodium 5-(6-{[cis-3-(2-ethoxypyridin-4-yl)-3-fluorocyclobutyl]oxy}pyridin-3-yl)-isoxazol-3-olate. To a solution of 5-(6-{[cis-3-(2-ethoxypyridin-4-yl)-3-fluorocyclobutyl]-oxy}pyridin-3-yl)isoxazol-3-ol (93.6 mg, 0.252 mmol) in acetonitrile (2 mL) was added aqueous NaOH (0.1 M, 2.52 ml, 0.252 mmol). The mixture was stirred at r.t. for 1 h and then the reaction was dried under reduced pressure to afford the title compound. ¹H NMR (500 MHz, CD₃OD) δ 1.41 (3H, t, J=7.1 Hz), 2.92 (2H, d, J=6.4 Hz), 3.17 (2H, d, J=12.3 Hz), 4.38 (2H, q, J=7.1 Hz), 5.23 (1H, t, J=6.7 Hz), 6.28 (1H, s), 6.88 (1H, s), 6.97 (1H, d, J=8.7 Hz), 7.07 (1H, d, J=5.5 Hz), 8.07 (1H, d, J=8.9 Hz), 8.19 (1H, d, J=5.5 Hz), 8.57 (1H, s). MS (ESI) m/z: 372 [M+H]⁺.

Example 87 sodium 5-[6-({cis-3-[2-(cyclobutyloxy)pyridin-4-yl]-3-fluorocyclobutyl}oxy)pyridin-3-yl]isoxazol-3-olate

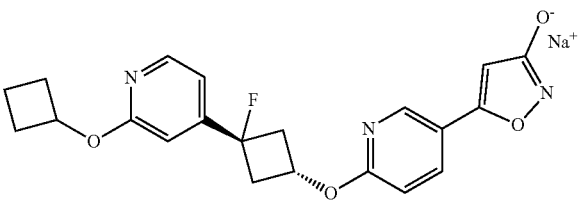 [SMILES: [O-]c1cc(-c2ccc(O[C@H]3C[C@](F)(c4ccnc(OC5CCC5)c4)C3)nc2)on1 ; [Na+]]

Step A: cis-3-(benzyloxy)-1-[2-(cyclobutyloxy)pyridin-4-yl]cyclobutanol. To a solution of 4-bromo-2-cyclobutoxypyridine (3 g, 13.15 mmol) in THF (50 mL) was added dropwise nBuLi (6.31 mL, 15.78 mmol) at −78° C. over 0.5 h. Then 3-(benzyloxy)cyclobutanone (2.78 g, 15.78 mmol) was added and the reaction was stirred at −78° C. for 2 h. The mixture was poured into water (60 mL), and exacted with EA (60 mL). The organic layer was dried over $Na_2SO_4$ and filtered. The filtrate was concentrated, and the resulting residue was purified by flash chromatography ($SiO_2$, eluting with PE:EA=5:1) to afford the title compound.

Step B: 4-[trans-3-(benzyloxy)-1-fluorocyclobutyl]-2-(cyclobutyloxy)pyridine. To a solution of cis-3-(benzyloxy)-1-[2-(cyclobutyloxy)pyridin-4-yl]cyclobutanol (1.6 g, 4.92 mmol) in DCM (30 mL) was added DAST (1.3 mL, 9.83 mmol) at −78° C. The reaction was stirred at −78° C. for 0.5 h, then poured into water (60 mL), extracted with DCM (20 mL), dried over $Na_2SO_4$, and filtered. The filtrate was concentrated, and the resulting residue was purified by flash chromatography ($SiO_2$, eluting with PE:EA=20:1) to afford the title compound.

Step C: trans-3-[2-(cyclobutyloxy)pyridin-4-yl]-3-fluorocyclobutanol. To a solution of 4-[trans-3-(benzyloxy)-1-fluorocyclobutyl]-2-(cyclobutyloxy)pyridine (1.3 g, 3.97 mmol) in DCM (20 mL) was added $BBr_3$ (3.97 mL, 7.94 mmol) in DCM dropwise at −78° C. The reaction was stirred at −78° C. for 0.1 h, then poured into water (30 mL), extracted with DCM (20 mL), dried with $Na_2SO_4$, and filtered. The filtrate was concentrated, and the resulting residue was purified by flash chromatography ($SiO_2$, eluting with PE:EA=5:1) to afford the title compound.

Step D: cis-3-[2-(cyclobutyloxy)pyridin-4-yl]-3-fluorocyclobutyl 4-nitrobenzoate. To a solution of trans-3-[2-(cyclobutyloxy)pyridin-4-yl]-3-fluorocyclobutanol (550 mg, 2.318 mmol), 4-nitrobenzoic acid (581 mg, 3.48 mmol), and $Ph_3P$ (912 mg, 3.48 mmol) in THF (10 mL) was added DEAD (0.550 ml, 3.48 mmol) in portions at 10° C. The reaction was stirred at 40° C. for 12 h and then concentrated. The resulting residue was purified by flash chromatography ($SiO_2$, eluting with PE:EA=20:1), to afford the title compound.

Step E: cis-3-[2-(cyclobutyloxy)pyridin-4-yl]-3-fluorocyclobutanol. To a solution of cis-3-[2-(cyclobutyloxy)pyridin-4-yl]-3-fluorocyclobutyl 4-nitrobenzoate (760 mg, 1.967 mmol) in methanol (10 ml), water (2 mL) was added $K_2CO_3$ (544 mg, 3.93 mmol) in portions. The reaction was stirred at 70° C. for 2 h. Then the mixture was poured into water (30 mL), extracted with EA (40 mL), dried ($Na_2SO_4$), and filtered. The filtrate was concentrated to afford the title compound, which was used without further purification in the next step.

Step F: 2-(cyclobutyloxy)-4-[cis-1-fluoro-3-({5-[3-(methoxymethoxy)isoxazol-5-yl]-pyridin-2-yl}oxy)cyclobutyl]pyridine. To a solution of cis-3-[2-(cyclobutyloxy)pyridin-4-yl]-3-fluorocyclobutanol (400 mg, 1.686 mmol), sodium 2-methylpropan-2-olate (389 mg, 4.05 mmol) in THF (30 ml) was added 5-(6-chloropyridin-3-yl)-3-(methoxymethoxy)isoxazole (426 mg, 1.770 mmol) at 10° C. The reaction was stirred at 40° C. for 4 h, then poured into water (10 mL), extracted with EA (10 mL), dried ($Na_2SO_4$), and filtered. The filtrate was concentrated to afford the title compound, which was used without further purification in the next step. MS (ESI) m/z: 442.3 [M+H]⁺.

Step G: 5-[6-({cis-3-[2-(cyclobutyloxy)pyridin-4-yl]-3-fluorocyclobutyl}oxy)pyridin-3-yl]isoxazol-3-ol. To a solution of 2-(cyclobutyloxy)-4-[cis-1-fluoro-3-({5-[3-(methoxymethoxy)-isoxazol-5-yl]pyridin-2-yl}oxy)cyclobutyl]pyridine (500 mg, 0.566 mmol) in THF (10 mL) was added 3M aqueous HCl (2 mL, 6.00 mmol). The reaction was stirred at 40° C. for 2 h, then poured into water (20 mL), extracted with EA (10 mL), dried ($Na_2SO_4$), filtered and concentrated. The resulting residue was purified by prep-HPLC (TFA modifier) to afford the title compound. ¹H NMR (400 MHz, $CD_3OD$) δ 8.55 (d, J=1.98 Hz, 1H), 8.17 (d, J=5.51 Hz, 1H), 8.02-8.19 (m, 1H), 7.15 (d, J=5.51 Hz, 1H), 6.89-7.00 (m, 2H), 6.31 (s, 1H), 5.61 (s, 1H), 5.11-5.21 (m, 1H), 3.09-3.24 (m, 1H), 2.78-2.93 (m, 2H), 2.42-2.55 (m, 2H), 2.08-2.26 (m, 2H), 1.81-1.95 (m, 1H), 1.66-1.81 (m, 1H). MS (ESI) m/z: 398.3 [M+H]⁺.

Step H: sodium 5-[6-({cis-3-[2-(cyclobutyloxy)pyridin-4-yl]-3-fluorocyclobutyl})-pyridin-3-yl]isoxazol-3-olate. To a solution of 5-[6-({cis-3-[2-(cyclobutyloxy)pyridin-4-yl]-3-fluorocyclobutyl}oxy)pyridin-3-yl]isoxazol-3-ol (180 mg, 0.453 mmol) in acetonitrile (15 ml) and water (10 ml) was added NaOH (0.906 ml, 0.453 mmol). The mixture was stirred at rt. for 1 h and then the reaction mixture was dried under reduced pressure to afford the title compound. MS (ESI) m/z: 398.0 [M+H]⁺.

Example 88

2-(cyclobutyloxy)-4-(trans-1-fluoro-3-{[5-(3-hydroxyisoxazol-5-yl)pyridinium-2-yl]oxy}cyclobutyl) pyridinium bis(trifluoroacetate)

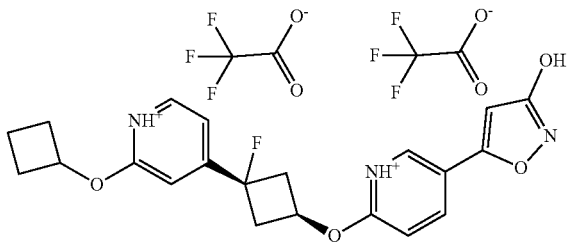 [SMILES: Oc1cc(-c2ccc(O[C@H]3C[C@@](F)(c4cc[nH+]c(OC5CCC5)c4)C3)[nH+]c2)on1 ; O=C([O-])C(F)(F)F ; O=C([O-])C(F)(F)F]

Step A: 2-(cyclobutyloxy)-4-[trans-1-fluoro-3-({5-[3-(methoxymethoxy)isoxazol-5-yl]-pyridin-2-yl}oxy)cyclobutyl]pyridine. To a solution of cis-3-[2-(cyclobutyloxy) pyridin-4-yl]-3-fluorocyclobutanol (40 mg, 0.169 mmol), and sodium 2-methylpropan-2-olate (32.4 mg, 0.337 mmol) in THF (5 mL) was added 5-(6-chloropyridin-3-yl)-3-(methoxymethoxy)isoxazole (38.5 mg, 0.160 mmol) at 10° C. The reaction was stirred at 40° C. for 4 h. The mixture was poured into water (10 mL), extracted with EA (10 mL), dried ($Na_2SO_4$), and filtered. The filtrate was concentrated, and the resulting residue was purified by prep-HPLC (TFA modifier) to afford the title compound.

Step B: 5-[6-({trans-3-[2-(cyclobutyloxy)pyridin-4-yl]-3-fluorocyclobutyl}oxy)pyridin-3-yl]isoxazol-3-ol. To a solution of 2-(cyclobutyloxy)-4-[trans-1-fluoro-3-({5-[3-(methoxy-methoxy)isoxazol-5-yl]pyridin-2-yl}oxy) cyclobutyl]pyridine (40 mg, 0.091 mmol) in THF (2 mL) was added 2 M aqueous HCl (0.5 mL, 1.000 mmol). The reaction was stirred at 40° C. for 2 h, then poured into water (10 mL), extracted with EA (10 mL), dried ($Na_2SO_4$), and filtered. The filtrate was concentrated, and the resulting residue was purified by prep-HPLC (TFA modifier) to afford the title compound. ¹H NMR (400 MHz, $CD_3OD$) 8.57 (d, J=1.98 Hz, 1H), 8.17 (d, J=5.51 Hz, 1H), 8.02-8.10 (m, 1H), 7.16 (d, J=5.51 Hz, 1H), 6.89-7.00 (m, 2H), 6.31 (s, 1H), 5.61 (s, 1H), 5.11-5.21 (m, 1H), 3.09-3.24 (m, 1H), 2.66-

2.83 (m, 2H), 2.42-2.54 (m, 2H), 2.08-2.23 (m, 2H), 1.81-1.94 (m, 1H), 1.66-1.80 (m, 1H). MS (ESI) m/z: 398.3 [M+H]⁺.

Example 89

5-[5-({trans-3-fluoro-3-[2-fluoro-5-(trifluoromethoxy)phenyl]-cyclobutyl}oxy)pyrazin-2-yl]isoxazol-3-ol

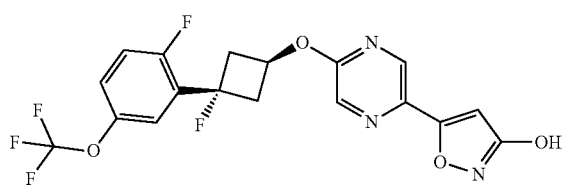 [SMILES: Oc1cc(-c2cnc(O[C@H]3C[C@@](F)(c4cc(OC(F)(F)F)ccc4F)C3)cn2)on1]

Step A: 3-(benzyloxy)-1-(2-fluoro-5-(trifluoromethoxy)phenyl)cyclobutan-1-ol. A solution of 2-bromo-1-fluoro-4-(trifluoromethoxy)benzene (1.295 g, 5 mmol) in THF (10 mL) was purged with $N_2$ for 5 min and isopropylmagnesium lithium chloride (3.85 mL, 5.00 mmol) was added at 0° C. The reaction was kept at 0° C. for 30 min, followed by the dropwise addition of a solution of 3-(benzyloxy)cyclobutanone (0.881 g, 5 mmol) in THF (5 mL). Then the cooling bath was removed and the reaction was allowed to warm to room temperature and stirred overnight. Then the reaction was quenched by addition of a minimum amount of the saturated aqueous $NH_4Cl$. The mixture was dried over $Na_2SO_4$ and concentrated. The resulting residue was purified by normal phase column chromatography ($SiO_2$) using 25% of EtOAc in hexanes to afford the title compound.

Step B: 3-fluoro-3-(2-fluoro-5-(trifluoromethoxy)phenyl)cyclobutan-1-ol. A solution of 3-(benzyloxy)-1-(2-fluoro-5-(trifluoromethoxy)phenyl)cyclobutanol (108 mg, 0.303 mmol) in DCM (3 mL) was treated with DAST (1.0 M in DCM, 0.606 mL) at 0° C. The cooling bath was removed and the reaction was allowed to warm to rt. Then the reaction was quenched with aqueous $NaHCO_3$ at 0° C. and extracted by DCM (3×2 mL). The combined organic layers were dried ($Na_2SO_4$), filtered and concentrated. The resulting residue was purified by normal phase column chromatography ($SiO_2$) using 5% of EtOAc in hexanes to give the title compound, which was used in the next step. To a solution of 2-(3-(benzyloxy)-1-fluorocyclobutyl)-1-fluoro-4-(trifluoromethoxy)benzene in MeOH was added 15% Pd/C (10% on C, 20 mg). The reaction was stirred at 1 atm of $H_2$ for 1 h. Then the reaction was filtered and solvent was removed under reduced pressure to afford the title compound, which was used in the next step without further purification.

Step C: 2-(3-fluoro-3-(2-fluoro-5-(trifluoromethoxy)phenyl)cyclobutoxy)-5-iodopyrazine. A solution of 3-fluoro-3-(2-fluoro-5-(trifluoromethoxy)phenyl)cyclobutanol (160 mg, 0.597 mmol) in THF (6 mL) was purged with $N_2$ for 5 min, then NaHMDS (1.0 M in THF, 0.597 mL) was added at room temperature. After stirring for 10 min, a solution of 2-bromo-5-iodopyrazine (1313 μL, 0.656 mmol) in DMA (1.0 M) was added and the reaction was kept at room temperature overnight. The reaction was quenched with a minimum amount of saturated aqueous $NH_4Cl$ and the solvent was removed under reduced pressure. The resulting residue was purified by normal phase column chromatography ($SiO_2$) using 5% of EtOAc in hexanes to give the title compound.

Step D: ethyl 3-(5-(3-fluoro-3-(2-fluoro-5-(trifluoromethoxy)phenyl)cyclobutoxy)-pyrazin-2-yl)propiolate. A suspension of 2-(-3-fluoro-3-(2-fluoro-5-(trifluoromethoxy)phenyl)-cyclobutoxy)-5-iodopyrazine (85 mg, 0.180 mmol) and copper oxide (25.8 mg, 0.180 mmol) in 1,4-dioxane (1.8 mL) was purged with $N_2$ for 5 min, then ethyl propiolate (18.24 μL, 0.180 mmol) was added at room temperature. The reaction was heated up to 100° C. for 3 days, then filtered and filtrate was removed under reduced pressure. The resulting residue was purified by normal phase column chromatography ($SiO_2$) using 10% EtOAc in hexanes to give the title compound.

Step E: 5-(5-(3-fluoro-3-(2-fluoro-5-(trifluoromethoxy)phenyl)cyclobutoxy)pyrazin-2-yl)-isoxazol-3-ol. A solution of ethyl 3-(5-(3-fluoro-3-(2-fluoro-5-(trifluoromethoxy)phenyl)-cyclobutoxy)pyrazin-2-yl)propiolate (9 mg, 0.020 mmol) and hydroxylamine HCl salt in EtOH (1 mL) was treated with NaOH (1.0 M, 0.244 mL). Then the reaction was stirred at room temperature for 4 h, followed by heating to 50° C. for 2 h. The reaction was carefully neutralized to pH 6-7 using 1 N HCl and extracted with EtOAc (3×2 mL). The combined organic layers were concentrated under reduced pressure and the resulting residue was purified by reverse phase column chromatography (TFA modifier) to give the title compound as a mixture of stereoisomers.

Step F: 5-[5-({trans-3-fluoro-3-[2-fluoro-5-(trifluoromethoxy)phenyl]cyclobutyl}oxy)-pyrazin-2-yl]isoxazol-3-ol.

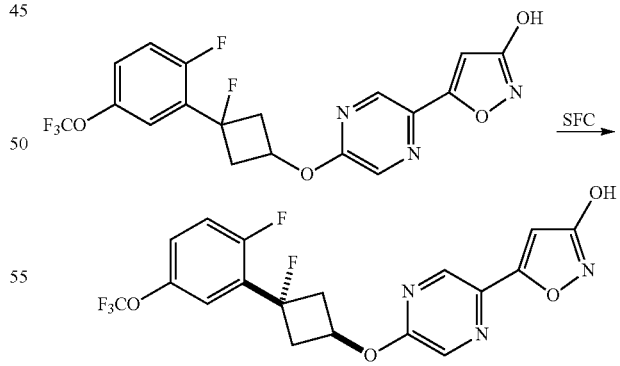

The mixture of stereoisomers from Step E was resolved by SFC using 40% MeOH as co-solvent on AD-H (21×250 mm) column. Peak 1 from SFC afforded the title compound. ¹H NMR (500 MHz, $CD_3OD$) δ 3.01-2.91 (2H, m), 3.30-3.23 (2H, m), 5.70-5.64 (1H, m), 6.41 (1H, s), 7.33-7.29 (1H, m), 7.39 (2H, d, J=6.9 Hz), 8.29 (1H, d, J=1.3 Hz), 8.63 (1H, d, J=1.3 Hz).

Example 90 ammonium 5-[6-({cis-3-[2-(cyclopropyloxy)pyridin-4-yl]-3-fluoro-cyclobutyl})oxy)pyridin-3-yl]isoxazol-3-olate

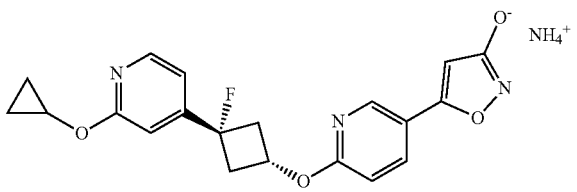 [SMILES: [O-]c1cc(-c2ccc(O[C@H]3C[C@](F)(c4ccnc(OC5CC5)c4)C3)nc2)on1 ; [NH4+]]

Step A: 4-bromo-2-(cyclopropyloxy)pyridine. To a solution of 4-bromo-2-fluoropyridine (3000 mg, 17.05 mmol) and cyclopropanol (1287 mg, 22.16 mmol) in NMP (22.6 mL) was added sodium tert-butoxide (22.7 mL, 22.67 mmol). After 50 min, the reaction mixture was partitioned between ethyl acetate and water (100 mL). The organic layer was separated, washed with water, brine, dried over $Na_2SO_4$, filtered and concentrated. The resulting residue was purified by a flash column chromatography on silica gel (ISCO 40 g $SiO_2$ column, eluting with 0-25% EtOAc/hexanes) to afford the title compound.

Step B: 3-{[tert-butyl(dimethyl)silyl]oxy}-1-[2-(cyclopropyloxy)pyridin-4-yl]cyclobutanol. To a solution of 4-bromo-2-(cyclopropyloxy)pyridine (1010 mg, 4.72 mmol) in toluene (23.6 mL) at −78° C. was added nBuLi (2.5 M, 2359 µL, 5.90 mmol) over 5 min. The reaction mixture was aged for 30 min, then a solution of 3-{[tert-butyl(dimethyl)silyl]oxy}cyclobutanone (1513 mg, 7.55 mmol) in THF (3 mL) was added over 30 min, while maintaining an internal temperature below −55° C. Then the reaction was warmed to rt over 45 min, and water was added. The organic layer was retained, and the aqueous layer was extracted with EtOAc (3×10 mL). The combined organic layers were washed with brine, dried over $MgSO_4$, and concentrated. The resulting residue was purified by flash chromatography (ISCO 80 g $SiO_2$ column, eluting with 0-100% EtOAc/hexanes) to afford the title compound.

Step C: 4-(3-{[tert-butyl(dimethyl)silyl]oxy}-1-fluorocyclobutyl)-2-(cyclopropyloxy)pyridine. Diethylaminosulfur trifluoride (662 µL, 5.01 mmol) was added to a solution of 3-{[tert-butyl-(dimethyl)silyl]oxy}-1-[2-(cyclopropyloxy) pyridin-4-yl]cyclobutanol (840 mg, 2.504 mmol) in $CH_2Cl_2$ (10 mL) at −78° C. After stirring for 30 min, the mixture was diluted with water and extracted with $CH_2Cl_2$ (3×). The combined organic layers were washed with brine, dried over $MgSO_4$, and concentrated. The resulting residue was purified by a flash column chromatography on silica gel (ISCO 40 g $SiO_2$ column, eluting with 0-20% EtOAc/hexanes) to give the title compound.

Step D: 3-[2-(cyclopropyloxy)pyridin-4-yl]-3-fluorocyclobutanol. To a solution of 4-(3-{[tert-butyl-(dimethyl) silyl]oxy}-1-fluorocyclobutyl)-2-(cyclopropyloxy)pyridine (550 mg, 1.630 mmol) in THF (16.3 mL) at rt was added TBAF (1.0 M, 1956 µl, 1.956 mmol). The reaction mixture was stirred at rt overnight. The volatiles were removed, and the resulting residue was purified by flash column chromatography on silica gel (ISCO 40 g $SiO_2$ column, eluting with 0-20% EtOAc/hexanes) to give the title compound.

Step E: 2-(cyclopropyloxy)-4-[cis-1-fluoro-3-({5-[3-(methoxymethoxy)isoxazol-5-yl]pyridin-2-yl}oxy)cyclobutyl]pyridine. To a mixture of 3-[2-(cyclopropyloxy)pyridin-4-yl]-3-fluoro-cyclobutanol (131 mg, 0.587 mmol) and 2-chloro-5-[3-(methoxymethoxy)isoxazol-5-yl]pyridine (141 mg, 0.587 mmol) in THF (5868 µl) was added sodium 2-methylpropan-2-olate (113 mg, 1.174 mmol). The mixture was stirred at 60° C. for 1 h. Then the resulting mixture was quenched with aqueous $NH_4Cl$, and extracted with EtOAc (3×). The combined organic layers were washed with brine, dried over $Na_2SO_4$, and filtered. The filtrate was concentrated, and the resulting residue was purified with preparative TLC (hexanes/EA=3/1) to give a mixture of stereoisomers. The mixture of stereoisomers from was separated by SFC using MeOH as co-solvent on AS-H (4.6×250 mm) column to give peak 1 as the title compound. MS (ESI) m/z: 410.40[M+H]⁺.

Step F: ammonium 5-[6-({cis-3-[2-(cyclopropyloxy)pyridin-4-yl]-3-fluorocyclobutyl}oxy)-pyridin-3-yl]isoxazol-3-olate. To a solution of 2-(cyclopropyloxy)-4-[cis-1-fluoro-3-({5-[3-(methoxymethoxy)isoxazol-5-yl]pyridin-2-yl}oxy)cyclobutyl]pyridine (15 mg, 0.035 mmol) in THF (351 µL) was added HCl (4.0 M, 61.4 µl, 0.246 mmol) in 1,4-dioxane. The mixture was stirred at 60° C. for 2 h, then additional HCl (26.3 µl, 0.105 mmol) was added. The reaction mixture was stirred at 60° C. for 20 min, then concentrated. The resulting residue was purified by reverse phase column chromatography using $NH_4OH$ as the modifier to give the title compound. ¹H NMR (500 MHz, $CD_3OD$) δ 0.87-0.74 (4H, m), 2.92-2.83 (2H, m), 3.21-3.15 (2H, m), 4.19 (1H, tt, J=6.2, 3.0 Hz), 5.24 (1H, h, J=6.7 Hz), 6.29 (1H, s), 6.96 (1H, dd, J=8.7, 0.7 Hz), 7.01 (1H, s), 7.15 (1H, dd, J=5.4, 1.5 Hz), 8.06 (1H, dd, J=8.7, 2.4 Hz), 8.23 (1H, d, J=5.4 Hz), 8.56 (1H, dd, J=2.4, 0.7 Hz). ESI m/z: 384.2 [M+H]⁺.

Example 91 ammonium 5-[5-({cis-3-[2-(cyclopropyloxy)pyridin-4-yl]-3-fluoro-cyclobutyl}oxy)pyrazin-2-yl]isoxazol-3-olate

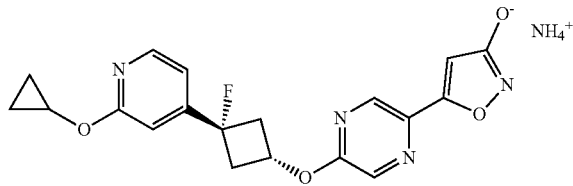 [SMILES: [O-]c1cc(-c2cnc(O[C@H]3C[C@](F)(c4ccnc(OC5CC5)c4)C3)cn2)on1 ; [NH4+]]

Step A: 4-bromo-2-(cyclopropyloxy)pyridine. To a solution of 4-bromo-2-fluoropyridine (3000 mg, 17.05 mmol) and cyclopropanol (1287 mg, 22.16 mmol) in NMP (22.6 mL) was added sodium tert-butoxide (22.7 mL, 22.67 mmol). The reaction mixture was stirred 50 min, then partitioned between ethyl acetate and water (100 mL). The organic layer was separated, washed with water, brine, dried over $Na_2SO_4$, filtered and concentrated. The resulting residue was purified by a flash column chromatography on silica gel (ISCO 40 g $SiO_2$ column, eluting with 0-25% EtOAc/hexanes) to afford the title compound.

Step B: 3-{[tert-butyl(dimethyl)silyl]oxy}-1-[2-(cyclopropyloxy)pyridin-4-yl]cyclobutanol. To a solution of 4-bromo-2-(cyclopropyloxy)pyridine (1010 mg, 4.72 mmol) in toluene (23.6 mL) at −78° C. was added nBuLi (2.5 M, 2359 µL, 5.90 mmol) over 5 min. The reaction mixture was stirred for 30 min, then a solution of 3-{[tert-butyl(dimethyl)silyl]oxy}cyclobutanone (1513 mg, 7.55 mmol) in THF (3 mL) was added over 30 min while maintaining the internal temperature below −55° C. The reaction was warmed to rt over 45 min, and water was added. The organic layer was retained, and the aqueous layer was extracted with EtOAc (3×10 mL). The combined organic layers were washed with brine, dried over MgSO$_4$, and concentrated. The resulting residue was purified by flash chromatography (ISCO 80 g SiO$_2$ column, eluting with 0-100% EtOAc/hexanes) to afford the title compound.

Step C: 4-(3-{[tert-butyl(dimethyl)silyl]oxy}-1-fluorocyclobutyl)-2-(cyclopropyloxy)pyridine. Diethylaminosulfur trifluoride (662 μL, 5.01 mmol) was added to a solution of 3-{[tert-butyl-(dimethyl)silyl]oxy}-1-[2-(cyclopropyloxy)pyridin-4-yl]cyclobutanol (840 mg, 2.504 mmol) in CH$_2$Cl$_2$ (10 mL) at −78° C. After stirring for 30 min, the mixture was diluted with water and extracted with CH$_2$Cl$_2$ (3×). The combined organic layers were washed with brine, dried over MgSO$_4$, and concentrated. The resulting residue was purified by a flash column chromatography on silica gel (ISCO 40 g SiO$_2$ column, eluting with 0-20% EtOAc/hexanes) to afford the title compound.

Step D: 3-[2-(cyclopropyloxy)pyridin-4-yl]-3-fluorocyclobutanol. To a solution of 4-(3-{[tert-butyl(dimethyl)silyl]oxy}-1-fluorocyclobutyl)-2-(cyclopropyloxy)pyridine (550 mg, 1.630 mmol) in THF (16.3 mL) at rt was added TBAF (1.0 M, 1956 μL, 1.956 mmol). The reaction mixture was stirred at rt overnight. After removal of volatiles, the residue was purified by flash column chromatography on silica gel (ISCO 40 g SiO$_2$ column, eluting with 0-20% EtOAc/hexanes) to give the title compound.

Step E: 2-({cis-3-[2-(cyclopropyloxy)pyridin-4-yl]-3-fluorocyclobutyl}oxy)-5-[3-(methoxy-methoxy)isoxazol-5-yl]pyrazine. To a mixture of 3-[2-(cyclopropyloxy)pyridin-4-yl]-3-fluoro-cyclobutanol (120 mg, 0.538 mmol) and 2-bromo-5-[3-(methoxymethoxy)isoxazol-5-yl]pyrazine (169 mg, 0.591 mmol) in THF (5375 μL) was added sodium 2-methylpropan-2-olate (103 mg, 1.075 mmol). The reaction mixture was stirred at 60° C. for 1 h, then quenched with aqueous NH$_4$Cl, and extracted with EtOAc (3×). The combined organic layers were washed with brine, dried over Na$_2$SO$_4$, filtered and concentrated. The resulting residue was purified by a flash column chromatography on silica gel (ISCO 24 g SiO$_2$ column, eluting with 0-70% EtOAc/hexanes) to give a mixture of products of cis and trans stereoisomers. The mixture of stereoisomers was separated by SFC to give the title compound. LCMS (MS (ESI) m/z: 429.2[M+H]$^+$.

Step F: ammonium 5-[5-({cis-3-[2-(cyclopropyloxy)pyridin-4-yl]-3-fluorocyclobutyl}oxy)-pyrazin-2-yl]isoxazol-3-olate. To a solution of 2-({cis-3-[2-(cyclopropyloxy)pyridin-4-yl]-3-fluorocyclobutyl}oxy)-5-[3-(methoxymethoxy)isoxazol-5-yl]pyrazine from Step E (25 mg, 0.058 mmol) in THF (584 μL) was added HCl (102 μL, 0.408 mmol). The reaction mixture was stirred at 60° C. for 1 h, then concentrated. The resulting residue was purified by reverse phase column chromatography using NH$_4$OH as the modifier to give the title compound. $^1$H NMR (500 MHz, CD$_3$OD) δ 0.86-0.73 (4H, m), 2.98-2.89 (2H, m), 3.23-3.17 (2H, m), 4.19 (1H, tt, J=6.2, 3.0 Hz), 5.31-5.24 (1H, m), 6.32 (1H, s), 7.01 (1H, d, J=1.4 Hz), 7.15 (1H, dd, J=5.4, 1.5 Hz), 8.23 (1H, d, J=5.4 Hz), 8.33 (1H, d, J=1.4 Hz), 8.56 (1H, d, J=1.3 Hz). MS (ESI) m/z: 385.4 [M+H]$^+$.

TABLE 3

The compounds of Examples 92-108 were prepared from the appropriate previously described or commercially available starting materials using procedures similar to those in the Examples herein

| Example | Structure | Name | Exact Mass [M + H]$^+$ |
|---|---|---|---|
| 92 | 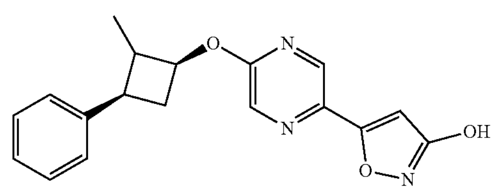 [SMILES: CC1[C@@H](Oc2cnc(-c3cc(O)no3)cn2)C[C@H]1c1ccccc1] | 5-(5-{[(1S,3R)-2-methyl-3-phenylcyclobutyl]oxy}pyrazin-2-yl)isoxazol-3-ol | 324 |
| 93 | 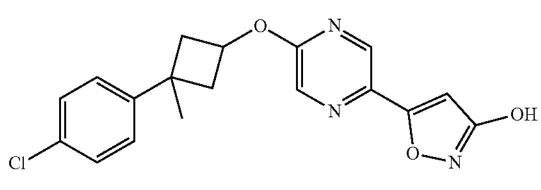 [SMILES: CC1(c2ccc(Cl)cc2)CC(Oc2cnc(-c3cc(O)no3)cn2)C1] | 5-(5-{[3-(4-chlorophenyl)-3-methylcyclobutyl]oxy}pyrazin-2-yl)isoxazol-3-ol | 358 |
| 94 | 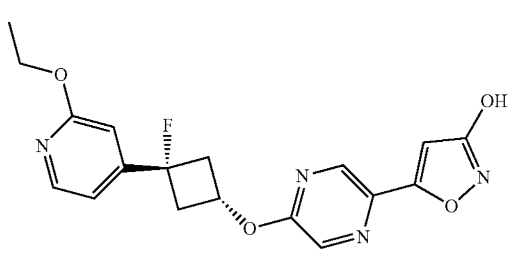 [SMILES: CCOc1cc([C@]2(F)C[C@@H](Oc3cnc(-c4cc(O)no4)cn3)C2)ccn1] | 5-(5-{[cis-3-(2-ethoxypyridin-4-yl)-3-fluorocyclobutyl]oxy}pyrazin-2-yl)isoxazol-3-ol | 373 |

TABLE 3-continued

The compounds of Examples 92-108 were prepared from the appropriate previously described or commercially available starting materials using procedures similar to those in the Examples herein

| Example | Structure | Name | Exact Mass [M + H]+ |
|---|---|---|---|
| 95 | 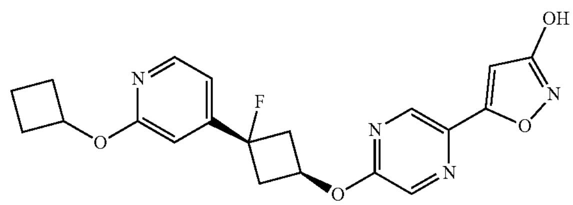 [SMILES: Oc1cc(-c2cnc(O[C@H]3C[C@@](F)(c4ccnc(OC5CCC5)c4)C3)cn2)on1] | 5-[5-({trans-3-[2-(cyclobutyloxy)pyridin-4-yl]-3-fluorocyclobutyl}oxy)pyrazin-2-yl]isoxazol-3-ol | 399 |
| 96 | 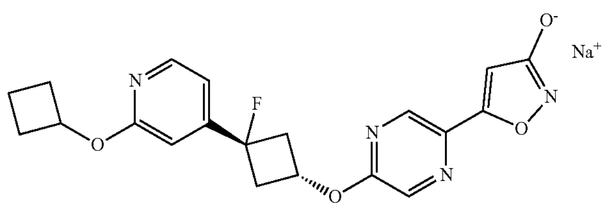 [SMILES: [O-]c1cc(-c2cnc(O[C@H]3C[C@](F)(c4ccnc(OC5CCC5)c4)C3)cn2)on1 ; [Na+]] | sodium 5-[5-({cis-3-[2-(cyclobutyloxy)pyridin-4-yl]-3-fluorocyclobutyl}oxy)pyrazin-2-yl]isoxazol-3-olate | 399 |
| 97 | 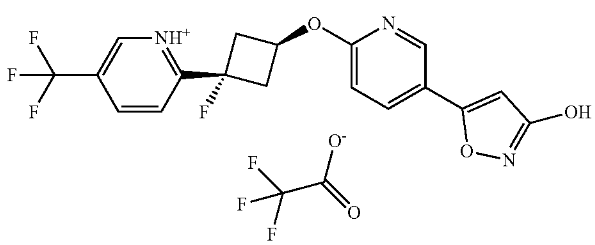 [SMILES: Oc1cc(-c2ccc(O[C@H]3C[C@@](F)(c4ccc(C(F)(F)F)c[nH+]4)C3)nc2)on1 ; O=C([O-])C(F)(F)F] | 2-(trans-1-fluoro-3-{[5-(3-hydroxyisoxazol-5-yl)pyridin-2-yl]oxy}cyclobutyl)-5-(trifluoromethyl)pyridinium trifluoroacetate | 396 |
| 98 | 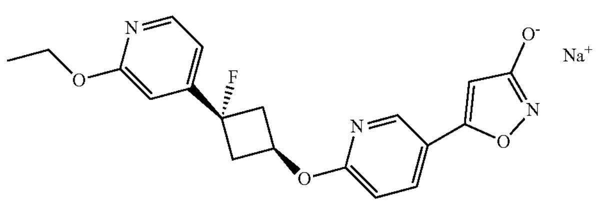 [SMILES: CCOc1cc([C@]2(F)C[C@H](Oc3ccc(-c4cc([O-])no4)cn3)C2)ccn1 ; [Na+]] | Sodium 5-(6-{[trans-3-(2-ethoxypyridin-4-yl)-3-fluorocyclobutyl]oxy}pyridin-3-yl)isoxazol-3-olate | 372 |
| 99 | 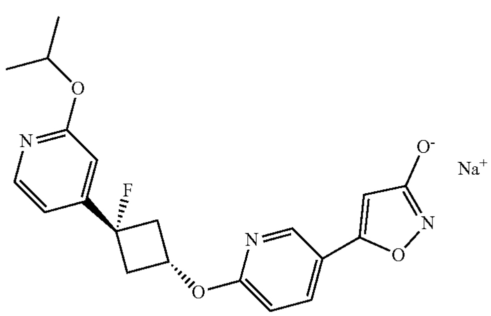 [SMILES: CC(C)Oc1cc([C@]2(F)C[C@@H](Oc3ccc(-c4cc([O-])no4)cn3)C2)ccn1 ; [Na+]] | sodium 5-[6-({cis-3-fluoro-3-[2-(propan-2-yloxy)pyridin-4-yl]cyclobutyl}oxy)pyridin-3-yl]isoxazol-3-olate | 386 |
| 100 | 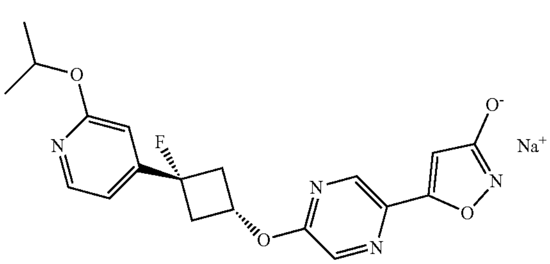 [SMILES: CC(C)Oc1cc([C@]2(F)C[C@@H](Oc3cnc(-c4cc([O-])no4)cn3)C2)ccn1 ; [Na+]] | sodium 5-[5-({cis-3-fluoro-3-[2-(propan-2-yloxy)pyridin-4-yl]cyclobutyl}oxy)pyrazin-2-yl]isoxazol-3-olate | 387 |

TABLE 3-continued

The compounds of Examples 92-108 were prepared from the appropriate previously
described or commercially available starting materials using procedures similar to those in the Examples herein

| Example | Structure | Name | Exact Mass [M + H]+ |
|---|---|---|---|
| 101 | 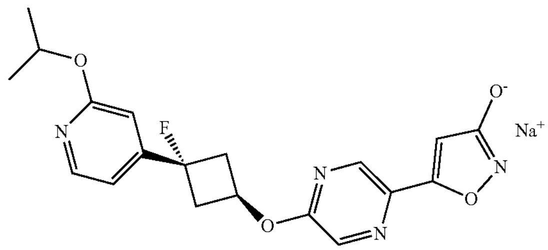 [SMILES: CC(C)Oc1cc([C@]2(F)C[C@H](Oc3cnc(-c4cc([O-])no4)cn3)C2)ccn1 ; [Na+]] | sodium 5-[5-({trans-3-fluoro-3-[2-(propan-2-yloxy)pyridin-4-yl]cyclobutyl}oxy)pyrazin-2-yl]isoxazol-3-olate | 387 |
| 102 | 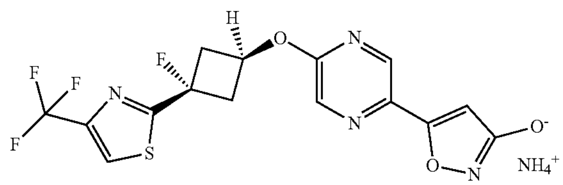 [SMILES: [O-]c1cc(-c2cnc(O[C@H]3C[C@@](F)(c4nc(C(F)(F)F)cs4)C3)cn2)on1 ; [NH4+]] | ammonium 5-[5-({trans-3-fluoro-3-[4-(trifluoromethyl)-1,3-thiazol-2-yl]cyclobutyl}oxy)pyrazin-2-yl]isoxazol-3-olate | 403 |
| 103 | 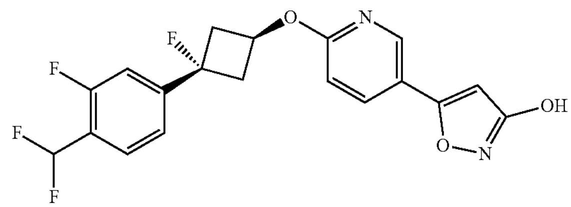 [SMILES: Oc1cc(-c2ccc(O[C@H]3C[C@@](F)(c4ccc(C(F)F)c(F)c4)C3)nc2)on1] | 5-[6-({trans-3-[4-(difluoromethyl)-3-fluorophenyl]-3-fluorocyclobutyl}oxy)pyridin-3-yl]isoxazol-3-ol | 395 |
| 104 | 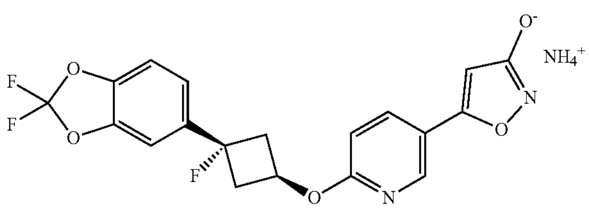 [SMILES: [O-]c1cc(-c2ccc(O[C@H]3C[C@@](F)(c4ccc5c(c4)OC(F)(F)O5)C3)nc2)on1 ; [NH4+]] | ammonium 5-(6-{[trans-3-(2,2-difluoro-1,3-benzodioxol-5-yl)-3-fluorocyclobutyl]oxy}pyridin-3-yl)isoxazol-3-olate | 407 |
| 105 | 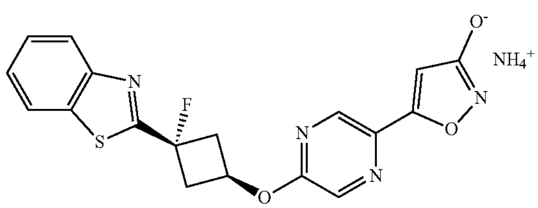 [SMILES: [O-]c1cc(-c2cnc(O[C@H]3C[C@@](F)(c4nc5ccccc5s4)C3)cn2)on1 ; [NH4+]] | ammonium 5-(5-{[trans-3-(1,3-benzothiazol-2-yl)-3-fluorocyclobutyl]oxy}pyrazin-2-yl)isoxazol-3-olate | 385 |
| 106 | 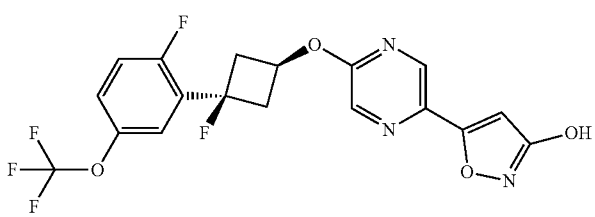 [SMILES: Oc1cc(-c2cnc(O[C@H]3C[C@](F)(c4cc(OC(F)(F)F)ccc4F)C3)cn2)on1] | 5-[5-({cis-3-fluoro-3-[2-fluoro-5-(trifluoromethoxy)phenyl]cyclobutyl}oxy)pyrazin-2-yl]isoxazol-3-ol | 430 |
| 107 | 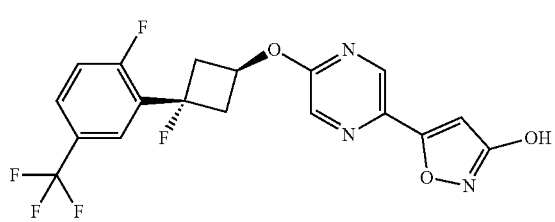 [SMILES: Oc1cc(-c2cnc(O[C@H]3C[C@@](F)(c4cc(C(F)(F)F)ccc4F)C3)cn2)on1] | 5-[5-({trans-3-fluoro-3-[2-fluoro-5-(trifluoromethyl)phenyl]cyclobutyl}oxy)pyrazin-2-yl]isoxazol-3-ol | 414 |

TABLE 3-continued

The compounds of Examples 92-108 were prepared from the appropriate previously described or commercially available starting materials using procedures similar to those in the Examples herein

| Example | Structure | Name | Exact Mass [M + H]+ |
|---|---|---|---|
| 108 | 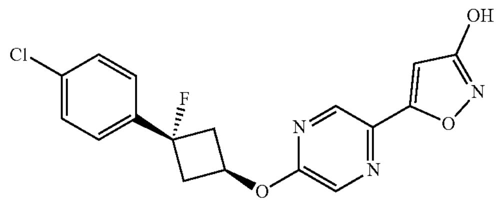 [SMILES: Oc1cc(-c2cnc(O[C@H]3C[C@@](F)(c4ccc(Cl)cc4)C3)cn2)on1] | 5-(5-{[trans-3-(4-chlorophenyl)-3-fluorocyclobutyl]oxy}pyrazin-2-yl)isoxazol-3-ol | 362 |

Example 109

5-(2-{[cis-3-(4-chlorophenyl)cyclobutyl]oxy}pyrimidin-5-yl)isoxazol-3-ol

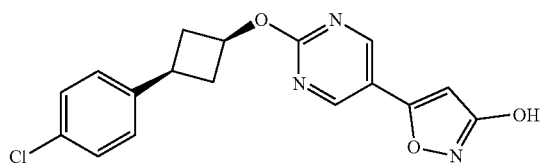 [SMILES: Oc1cc(-c2cnc(O[C@H]3C[C@@H](c4ccc(Cl)cc4)C3)nc2)on1]

Step A: 2-{[cis-3-4(4-chlorophenyl)cyclobutyl]oxy}-5-iodopyrimidine. To a solution of cis-3-(4-chlorophenyl)cyclobutanol (2.297 g, 12.58 mmol) and 2-chloro-5-iodopyrimidine (2.52 g, 10.48 mmol) in anhydrous THF (60 mL) was added sodium 2-methylpropan-2-olate (1.007 g, 10.48 mmol). The resulting mixture was stirred at 40° C. under $N_2$ for 3 h, then poured into water (50 mL) and extracted with EA (3×40 mL). The combined organic layers were washed with brine (3×10 mL), and dried over $Na_2SO_4$. After filtration and concentration, the resulting residue was purified by column chromatography ($SiO_2$, PE:EA=10:1) to afford the title compound. $^1H$ NMR (400 MHz, $CDCl_3$) 8.62 (s, 2H), 7.27 (s, 2H), 7.13-7.19 (m, 2H), 5.14 (q, J=7.43 Hz, 1H), 3.04-3.19 (m, 1H), 2.84-2.97 (m, 1H), 2.19-2.36 (m, 1H).

Step B: ethyl 3-(2-{[cis-3-(4-chlorophenyl)cyclobutyl]oxy}pyrimidin-5-yl)prop-2-ynoate. To a solution of 2-{[cis-3-(4-chlorophenyl)cyclobutyl]oxy}-5-iodopyrimidine (1.25 g, 3.23 mmol) in anhydrous DMF (40 mL) was added copper(I) oxide (0.463 g, 3.23 mmol) and ethyl propiolate (0.634 g, 6.47 mmol). The resulting mixture was stirred at 100° C. under $N_2$ for 12 h, then poured into water (60 mL) and extracted with EA (3×40 mL). The combined organic layer were washed with brine (3×10 mL), and dried over $Na_2SO_4$. After filtration and concentration, the resulting residue was purified by column chromatography ($SiO_2$, PE:EA=10:1) to afford the title compound. $^1H$ NMR (400 MHz, $CDCl_3$) δ 8.68 (s, 2H), 7.25-7.29 (m, 2H), 7.16 (d, J=8.22 Hz, 2H), 5.23 (q, J=7.43 Hz, 1H), 4.29 (q, J=7.04 Hz, 2H), 3.06-3.22 (m, 1H), 2.86-3.00 (m, 2H), 2.21-2.37 (m, 2H), 1.34 (t, J=7.24 Hz, 3H).

Step C: 5-(2-{[cis-3-(4-chlorophenyl)cyclobutyl]oxy}pyrimidin-5-yl)isoxazol-3-ol. To a solution of ethyl 3-(2-{[cis-3-(4-chlorophenyl)cyclobutyl]oxy}pyrimidin-5-yl)prop-2-ynoate (700 mg, 1.962 mmol) in EtOH (20 mL) was added dropwise a solution of NaOH (392 mg, 9.81 mmol) and hydroxylamine hydrochloride (409 mg, 5.89 mmol) in water (1 mL) at 0° C. The reaction was stirred for 30 min at 0° C., then stirred at 40° C. for 12 h. The reaction mixture was poured in to water (40 mL), and HCl (3 M) was added to adjust the pH to 5-6. The mixture was extracted with EtOAc (3×55 mL). The combined organic layer was washed with water (3×10 mL), and dried over $Na_2SO_4$. After filtration and concentration, the resulting residue was purified by prep-HPLC (TFA modifier) to give the title compound. $^1H$ NMR (400 MHz, $CD_3OD$) δ 8.83 (s, 2H), 7.22-7.30 (m, 4H), 6.07 (s, 1H), 5.27 (q, J=7.34 Hz, 1H), 3.14-3.26 (m, 1H), 2.89-3.03 (m, 2H), 2.14-2.33 (m, 2H). MS (ESI) m/z: 344.1 [M+H]+.

Example 110

5-{[trans-3-(4-chlorophenyl)cyclobutyl]oxy}-2-(3-hydroxyisoxazol-5-yl)pyridinium trifluoroacetate

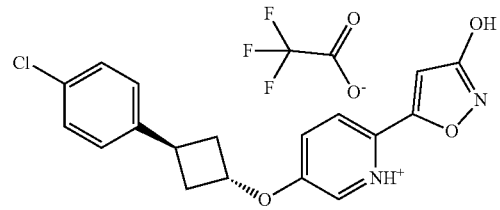 [SMILES: Oc1cc(-c2ccc(O[C@H]3C[C@H](c4ccc(Cl)cc4)C3)c[nH+]2)on1 ; O=C([O-])C(F)(F)F]

Step A: 2-bromo-5-{[trans-3-(4-chlorophenyl)cyclobutyl]oxy}pyridine. To a solution of cis-3-(4-chlorophenyl)cyclobutanol (682 mg, 3.74 mmol) in anhydrous THF (40 mL) were added 6-bromopyridin-3-ol (500 mg, 2.87 mmol), triphenylphosphine (904 mg, 3.45 mmol) and DEAD (0.910 mL, 5.75 mmol) at 25° C. The resulting mixture was stirred at 40° C. under $N_2$ for 8 h. Then the reaction mixture was poured into water (10 mL), extracted with EA (3×20 mL) and dried over $Na_2SO_4$. After filtration and concentration, the resulting residue was purified by flash column ($SiO_2$, PE:EA=10:1) to afford the title compound. $^1H$ NMR (400 MHz, $CDCl_3$) δ 7.94 (d, J=3.13 Hz, 1H), 7.26-7.38 (m, 3H), 7.13-7.21 (m, 2H), 6.99 (dd, J=8.61, 3.13 Hz, 1H), 4.78-4.88 (m, 1H), 3.66-3.81 (m, 1H), 2.49-2.73 (m, 4H).

Step B: 5-{[trans-3-(4-chlorophenyl)cyclobutyl]oxy}-2-iodopyridine. To a solution of 2-bromo-5-{[trans-3-(4-chlorophenyl)cyclobutyl]oxy}pyridine (400 mg, 1.181 mmol) in anhydrous 1,4-dioxane (20 mL) were added sodium iodide (97 mg, 0.650 mmol), N,N-dimethylethane-1,2-diamine (521 mg, 5.9 mmol), and copper(I) iodide (90 mg, 0.472 mmol) at 25° C. The resulting mixture was stirred at 110° C.

under N₂ for 10 h, then poured into water (10 mL), extracted with EA (3×20 mL), and dried over Na₂SO₄. After filtration and concentration, the resulting residue was purified by flash column (SiO₂, PE:EA=5:1) to afford the title compound. MS (ESI) m/z: 385.8 [M+H]⁺.

Step C: ethyl 3-(5-{[trans-3-(4-chlorophenyl)cyclobutyl]oxy}pyridin-2-yl)prop-2-ynoate. To a solution of 5-{[trans-3-(4-chlorophenyl)cyclobutyl]oxy}-2-iodopyridine (190 mg, 0.493 mmol) in anhydrous 1,4-dioxane (10 mL) were added copper(II) oxide (78 mg, 0.985 mmol), ethyl propiolate (193 mg, 1.971 mmol) at 25° C. The resulting mixture was stirred at 100° C. under N₂ for 10 h. Then the reaction mixture was poured into water (10 mL), extracted with EA (3×20 mL), and dried over Na₂SO₄. After filtration and concentration, the resulting residue was purified by flash column (SiO₂, PE:EA=5:1) to give the title compound. MS (ESI) m/z: 355.9 [M+H]⁺.

Step D: 5-{[trans-3-(4-chlorophenyl)cyclobutyl]oxy}-2-(3-hydroxyisoxazol-5-yl)pyridinium trifluoroacetate. To a solution of ethyl 3-(5-{[trans-3-(4-chlorophenyl)cyclobutyl]oxy}-pyridin-2-yl)prop-2-ynoate (25 mg, 0.070 mmol) in anhydrous EtOH (5 mL) and water (1 mL) was added hydroxylamine hydrochloride (14.65 mg, 0.211 mmol) and NaOH (16.86 mg, 0.422 mmol) at 25° C. The resulting mixture was stirred at 40° C. under N₂ for 10 h, then poured into water (10 mL), extracted with EA (3×20 mL), and dried over Na₂SO₄. After filtration and concentration, the resulting residue was purified by prep-HPLC (TFA modifier) to afford the title compound. ¹H NMR (400 MHz, CD₃OD) δ 8.24-8.29 (m, 1H), 7.79-7.86 (m, 1H), 7.37-7.43 (m, 1H), 7.32 (m, 4H), 6.37-6.42 (m, 1H), 5.02-5.09 (m, 1H), 3.72-3.82 (m, 1H), 2.68 (m, 4H). MS (ESI) m/z: 342.9 [M+H]⁺.

TABLE 4

The compounds of Examples 111-115 were prepared from the appropriate previously described or commercially available starting materials using procedures similar to those in the Examples herein

| Example | Structure | Name | Exact Mass [M + H]⁺ |
|---|---|---|---|
| 111 | 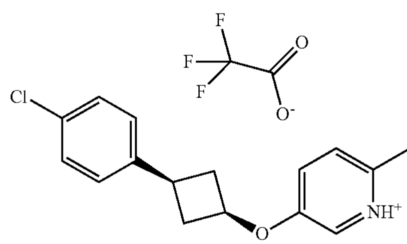 | 5-{[cis-3-(4-chlorophenyl)cyclobutyl]oxy}-2-(3-hydroxyisoxazol-5-yl)pyridinium trifluoroacetate | 343 |
| 112 | 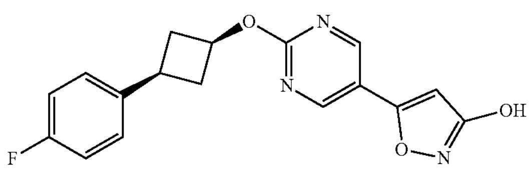 [SMILES: Oc1cc(-c2cnc(O[C@H]3C[C@@H](c4ccc(F)cc4)C3)nc2)on1] | 5-(2-{[cis-3-(4-fluorophenyl)cyclobutyl]oxy}pyrimidin-5-yl)isoxazol-3-ol | 328 |
| 113 | 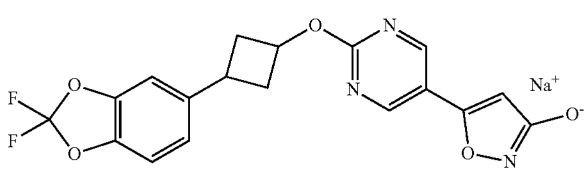 [SMILES: [O-]c1cc(-c2cnc(OC3CC(c4ccc5c(c4)OC(F)(F)O5)C3)nc2)on1 ; [Na+]] | sodium 5-(2-{[3-(2,2-difluoro-1,3-benzodioxol-5-yl)cyclobutyl]oxy}pyrimidin-5-yl)isoxazol-3-olate | 390 |
| 114 | 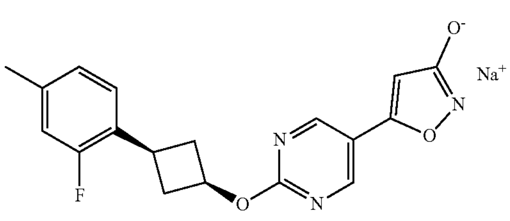 [SMILES: Cc1ccc([C@H]2C[C@@H](Oc3ncc(-c4cc([O-])no4)cn3)C2)c(F)c1 ; [Na+]] | sodium 5-(2-{[cis-3-(2-fluoro-4-methylphenyl)cyclobutyl]oxy}pyrimidin-5-yl)isoxazol-3-olate | 342 |
| 115 | 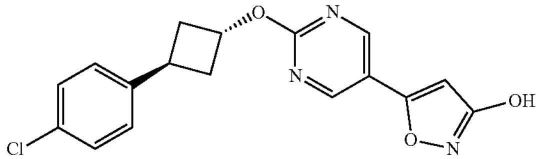 [SMILES: Oc1cc(-c2cnc(O[C@H]3C[C@H](c4ccc(Cl)cc4)C3)nc2)on1] | 5-(2-{[trans-3-(4-chlorophenyl)cyclobutyl]oxy}pyrimidin-5-yl)isoxazol-3-ol | 344 |

Examples 116-119

5-(3-hydroxyisoxazol-5-yl)-2-({3-[3-(trifluoromethoxy)-phenyl]cyclopentyl}oxy)pyridinium trifluoroacetate

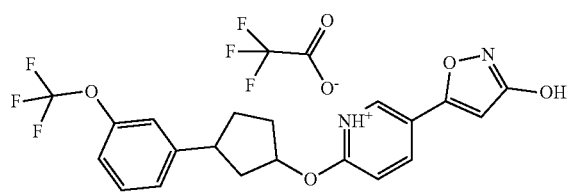 [SMILES: Oc1cc(-c2ccc(OC3CCC(c4cccc(OC(F)(F)F)c4)C3)[nH+]c2)on1 ; O=C([O-])C(F)(F)F]

Step A: 3-(3-(trifluoromethoxy)phenyl)cyclopentan-1-ol. In a 2-dram vial, 4,4,5,5-tetra-methyl-2-(3-(trifluoromethoxy)phenyl)-1,3,2-dioxaborolane (288 mg, 1.00 mmol), (rac)-BINAP (62.3 mg, 0.100 mmol) and Rh(acac)(C$_2$H$_4$) (25.8 mg, 0.100 mmol) were weighed out in a glove box. A degassed solution of cyclopent-2-enone (0.082 g, 1 mmol) in 1,4-dioxane (1.8 mL) was added, followed by the addition of degassed water (0.2 mL). The reaction was heated up to 100° C. overnight, then the solvent was removed under reduced pressure and the resulting residue was purified by normal phase column chromatography (SiO$_2$) using 10%-20% EtOAc in hexanes to give the ketone. To the ketone was added MeOH (3 mL) and a solution of NaBH$_4$ in diglyme (0.5 M, 2 mL, 1.0 mmol). The reaction was stirred at rt for 30 min, then quenched with 1 N HCl and the aqueous layer was extracted by EtOAc (3×2 mL). The combined organic layers were dried over Na$_2$SO$_4$ and concentrated. The resulting residue was used in the next step without further purification.

Step B: 3-(methoxymethoxy)-5-(6-((3-(3-(trifluoromethoxy)phenyl)cyclopentyl)oxy)pyridin-3-yl)isoxazole. To 3-[3-(trifluoromethoxy)phenyl]cyclopentan-1l-ol (Step A, 246 mg, 1.0 mmol) was added DMA (1.0 mL). The mixture was purged with N$_2$ for 5 min, followed by the addition of NaHMDS (1.0 M in THF, 1.2 mL) at room temperature. After 10 min, a solution of 2-chloro-5-[3-(methoxymethoxy)isoxazol-5-yl]pyridine in DMA (1.0 M, 1.0 mmol) was added and the reaction was heated to 100° C. overnight. Then the reaction was quenched by the addition of a minimum amount of pH 7 buffer solution. The solvent was removed under reduced pressure and the resulting residue was purified by normal phase column chromatography (SiO$_2$) using 15%-25% EtOAc in hexanes to give a mixture of stereoisomers. The mixture of stereoisomers was separated by SFC using EtOAc as co-solvent on a OD-H (21×250 mm) column to give 4 peaks.

Step C: 5-(3-hydroxyisoxazol-5-yl)-2-({3-[3-(trifluoromethoxy)phenyl]cyclopentyl}oxy)-pyridinium trifluoroacetate. Each separated stereoisomer from Step B (27 mg, Peak 1, 2 3 or 4 from SFC) was dissolved in 1,4-dioxane (1 mL), treated with 4 N HCl in 1,4-dioxane respectively (0.15 mL, 4.0 M, 10 mmol) and stirred overnight. Then the solvent was removed under reduced pressure. The resulting residue was purified by reverse phase column chromatography using acidic condition (TFA modifier) to afford the title compounds in Examples 117-120.

Example 117

5-(3-hydroxyisoxazol-5-yl)-2-({3-[3-(trifluoromethoxy)phenyl]cyclopentyl}oxy)pyridinium trifluoroacetate

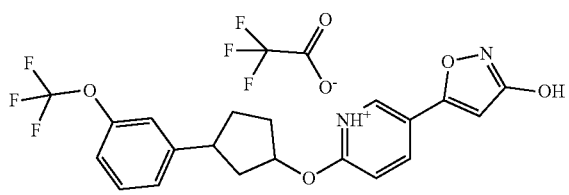 [SMILES: Oc1cc(-c2ccc(OC3CCC(c4cccc(OC(F)(F)F)c4)C3)[nH+]c2)on1 ; O=C([O-])C(F)(F)F]

The title compound isolated as Peak 1 by SFC: $^1$H NMR (500 MHz, DMSO-d$_6$) δ 1.84-1.72 (2H, m), 1.95 (1H, m), 2.15-2.06 (2H, m), 2.71-2.65 (1H, m), 3.27-3.20 (1H, m), 5.52 (2H, m), 6.53 (1H, s), 6.95 (1H, dd, J=8.7, 0.8 Hz), 7.19 (1H, dd, J=8.1, 2.2 Hz), 7.27 (1H, s), 7.36 (1H, d, J=7.8 Hz), 7.44 (1H, t, J=7.9 Hz), 8.10 (1H, dd, J=8.7, 2.5 Hz), 8.64 (1H, dd, J=2.5, 0.7 Hz), 11.41 (1H, s).

Example 118

5-(6-((3-(3-(trifluoromethoxy)phenyl)cyclopentyl)oxy)pyridin-3-yl isoxazol-3-ol

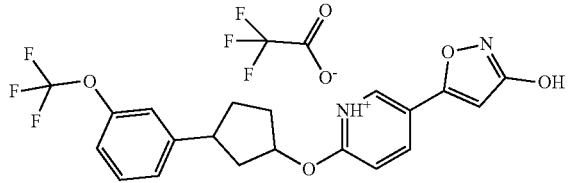 [SMILES: Oc1cc(-c2ccc(OC3CCC(c4cccc(OC(F)(F)F)c4)C3)[nH+]c2)on1 ; O=C([O-])C(F)(F)F]

The title compound isolated as Peak 2 by SFC: $^1$H NMR (500 MHz, DMSO-d$_6$) δ 1.70-1.62 (1H, m), 1.86-1.80 (1H, m), 2.04 (1H, ddd, J=13.9, 11.3, 6.3 Hz), 2.25-2.21 (2H, m), 2.42-2.35 (1H, m), 5.59 (1H, m), 6.53 (1H, s), 6.95 (1H, dd, J=8.7, 0.8 Hz), 7.20 (1H, d, J=7.9 Hz), 7.30 (1H, s), 7.37 (1H, d, J=7.8 Hz), 7.45 (1H, t, J=7.9 Hz), 8.09 (1H, dd, J=8.7, 2.5 Hz), 8.64 (1H, dd, J=2.5, 0.8 Hz), 11.41 (1H, s).

Example 119

5-(6-((3-(3-(trifluoromethoxy)phenyl)cyclopentyl)oxy)pyridin-3-yl)isoxazol-3-ol

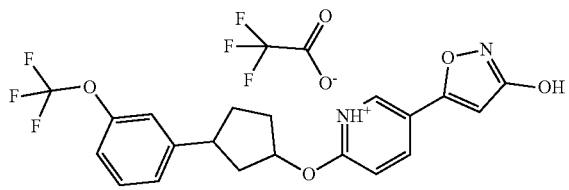 [SMILES: Oc1cc(-c2ccc(OC3CCC(c4cccc(OC(F)(F)F)c4)C3)[nH+]c2)on1 ; O=C([O-])C(F)(F)F]

The title compound isolated as Peak 3 by SFC: $^1$H NMR (500 MHz, CD$_3$OD) δ 1.20 (1H, m), 1.74 (1H, m), 2.02 (2H, m), 2.39 (2H, m), 3.47 (1H, m), 5.63 (1H, m), 6.32 (1H, s), 7.40-6.90 (5H, m), 8.04-8.04 (1H, m), 8.57-8.56 (1H, m).

Example 120

5-(6-((3-(3-(trifluoromethoxy)phenyl)cyclopentyl)oxy)pyridin-3 yl)isoxazol-3-ol

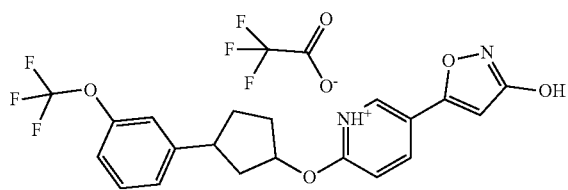 [SMILES: Oc1cc(-c2ccc(OC3CCC(c4cccc(OC(F)(F)F)c4)C3)[nH+]c2)on1 ; O=C([O-])C(F)(F)F]

The title compound isolated as Peak 4 by SFC: H NMR (500 MHz, CD$_3$OD) δ 1.95-1.83 (2H, m), 2.22-2.07 (3H, m), 2.77-2.71 (1H, m), 3.31-3.23 (1H, m), 5.60-5.57 (1H, m), 6.32 (1H, s), 6.92 (1H, dd, J=8.7, 0.8 Hz), 7.11-7.09 (1H, m), 7.23 (1H, s), 7.33 (1H, d, J=7.8 Hz), 7.40 (1H, t, J=7.9 Hz), 8.05 (1H, dd, J=8.7, 2.5 Hz), 8.58-8.57 (1H, m).

BIOLOGICAL ASSAYS

The usefulness of the compound encompassed by formula (I) for a medicament is shown in tests described below.

Human and Rat GPR120 IP1 Assay Principle

The binding of small molecule agonists to the G-protein-coupled receptor GPR120 activates phospholipase C, and leads to the generation of inositol 1,4,5-trisphosphate (InsP3 or IP3). IP3 is subsequently de-phosphorylated to IP1, which accumulates in cells and is stable in the presence of lithium chloride.

In the present method, agonist-induced activation of the human and rat GPR120 receptor was monitored by measuring the accumulation of IP1 in CHO-K1 cells that were stably expressing the short form of human GPR120 (Accession #NM_001195755) or HEK293 cells stably expressing rat GPR120 (Accession #NM_001047088). Following agonist addition, GPR120 activation and subsequent accumulation of IP1 was measured using a homogeneous Time Resolved Fluorescence-based ELISA commercially available from CisBio (IP-one ELISA Kit). The IP-One ELISA was a competitive immunoassay which uses IP1 labeled with HRP and a terbium cryptate-labeled anti-IP1 monoclonal antibody. Accumulation of unlabeled IP1 following GPR120 activation resulted in a loss of signal in the ELISA. The signal loss was then back calculated to IP1 concentration using an IP1 standard curve. Determination of IP1 concentration was a direct measure of GPR120 activation and was used to determine compound potency (EC$_{50}$).

Generation of GPR120-Expressing Cells

Human GPR120 stable cell-lines were generated in CHO cells. The expression plasmids were transfected using lipofectamine (Life Technologies) following manufacturer's instructions. Stable cell-lines were generated following drug selection and single cell cloning. Rat GPR120 stable cell-lines were generated in HEK cells using the Jump-In™ cell engineering platform (Life Technologies) following manufacturer's instructions. Stable cell-lines were generated following drug selection and single cell cloning.

Inositol Phosphate Turnover (IP1) Assay

The assay was performed in 384-well format. CHO cells stably expressing human GPR120 were plated at 20,000 cells per well in growth medium (DMEM/F12, 10% fetal calf serum). HEK293 cells stably expressing rat GPR120 were plated at 15,00 cells per well in growth medium (DMEM, 10% fetal calf serum). Cell plates were then incubated 16 hours at 37 degrees in a 5% CO2 incubator. Measurement of Inositol Phosphate Turnover (IP1) was performed using the CisBio IP-One kit (Part number 62IPA-PEB). After the 16 hour incubation, the growth media was removed by centrifugation using the BlueWasher (Aus-Washer GUI Ver. v1.0.1.8) Protocol #21-"Light Dry" and 10 µl of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% CO2 incubator. 10 µl of detection buffer (also prepared as described in the IP-One kit) was added to each well and the plates were incubated at room temperature for 60 minutes in the dark. The plates were then read in a Perkin ElmerEnVision or equivalent reader able to measure FRET. Fluorescent ratio of emission at 665 and 620 nm was then converted to the IP1 concentration by back calculating from an IP1 standard curve prepared at the time of the assay. The data was normalized to % activity using a reference compound, and the EC$_{50}$ values were determined using a standard 4-parameter fit.

The compounds of the present invention, including the compounds in Examples 1-120, have EC$_{50}$ values <10,000 nanomolar (nM) in the Human or rat GPR120 IP1 assays described above.

TABLE I

Specific EC$_{50}$ values in the Human or Rat GPR120 IP1 Assays (nM)

| Example | Human GPR120 IP1 | Rat GPR120 IP1 |
|---|---|---|
| 1 | 8.7 | |
| 2 | 178 | |
| 3 | 102 | |
| 4 | 83 | |
| 5 | 82 | |
| 6 | 129 | |
| 7 | 11 | |
| 8 | 303 | |
| 9 | 23 | |
| 10 | 34 | |
| 11 | 112 | |
| 12 | | 1.5 |
| 13 | 181 | |
| 14 | 19 | |
| 15 | 41 | |
| 16 | 64 | |
| 17 | 86 | |
| 18 | 134 | |
| 19 | 75 | |
| 20 | 42 | |
| 21 | 254 | |
| 22 | 92 | |
| 23 | | 100 |
| 24 | 19 | |
| 25 | 46 | |
| 26 | 86 | |
| 27 | 177 | |
| 28 | 28 | |
| 29 | 171 | |
| 30 | 155 | |
| 31 | 62 | |
| 32 | 16 | |
| 33 | 320 | |
| 34 | 25 | |
| 35 | 10 | |
| 36 | 41 | |
| 37 | 161 | |
| 38 | 17 | |

TABLE I-continued

Specific EC$_{50}$ values in the Human or Rat GPR120 IP1 Assays (nM)

| Example | Human GPR120 IP1 | Rat GPR120 IP1 |
|---|---|---|
| 39 | 48 | |
| 40 | 16 | |
| 41 | 17 | |
| 42 | 85 | |
| 43 | 130 | |
| 44 | 60 | |
| 45 | 24 | |
| 46 | 36 | |
| 47 | 104 | |
| 48 | 24 | |
| 49 | 9.7 | |
| 50 | 23 | |
| 51 | 16 | |
| 52 | 28 | |
| 53 | 14 | |
| 54 | 99 | |
| 55 | 11 | |
| 56 | 49 | |
| 57 | 23 | |
| 58 | 104 | |
| 59 | 8.0 | |
| 60 | 13 | |
| 61 | | 1.8 |
| 62 | 40 | |
| 63 | 53 | |
| 64 | 1990 | |
| 65 | 5.8 | |
| 66 | 37 | |
| 67 | 47 | |
| 68 | 52 | |
| 69 | 25 | |
| 70 | 24 | |
| 71 | 38 | |
| 72 | 29 | |
| 73 | 166 | |
| 74 | 11 | |
| 75 | 149 | |
| 76 | 138 | |
| 77 | 388 | |
| 78 | 305 | |
| 79 | 13 | |
| 80 | 23 | |
| 81 | 31 | |
| 82 | 7.1 | |
| 83 | 17 | |
| 84 | 12 | |
| 85 | 25 | |
| 86 | 26 | |
| 87 | | 4.7 |
| 88 | | 42.2 |
| 89 | 51 | |
| 90 | 22 | |
| 91 | | 36 |
| 92 | 17 | |
| 93 | 215 | |
| 94 | | 890 |
| 95 | | 18 |
| 96 | | 33 |
| 97 | 22 | |
| 98 | 15 | |
| 99 | 17 | |
| 100 | 153 | |
| 101 | 538 | |
| 102 | | 1160 |
| 103 | 40 | |
| 104 | 60 | |
| 105 | 237 | |
| 106 | 91 | |
| 107 | 215 | |
| 108 | 14 | |
| 109 | 11 | |
| 110 | | 1.1 |
| 111 | | 0.8 |
| 112 | 647 | |
| 113 | 41 | |
| 114 | 191 | |

TABLE I-continued

Specific EC$_{50}$ values in the Human or Rat GPR120 IP1 Assays (nM)

| Example | Human GPR120 IP1 | Rat GPR120 IP1 |
|---|---|---|
| 115 | | 5.8 |
| 116 | 18 | |
| 117 | 59 | |
| 118 | 34 | |
| 119 | 12 | |

EXAMPLE OF A PHARMACEUTICAL FORMULATION

As a specific embodiment of an oral composition of a compound of the present invention, 50 mg of any of the examples is formulated with sufficient finely divided lactose to provide a total amount of 580 to 590 mg to fill a size O hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound according to the formula I:

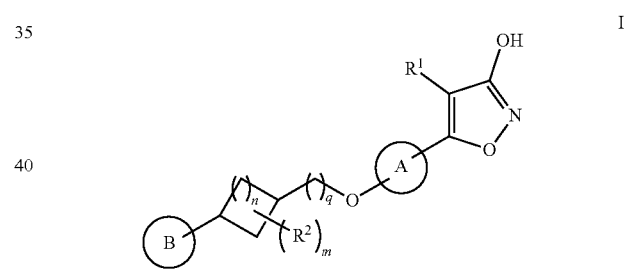

or a pharmaceutically acceptable salt thereof, wherein:

A is selected from:
  (1) aryl and
  (2) heteroaryl,
wherein each aryl and heteroaryl is unsubstituted or substituted with 1, 2, 3 or 4 substituents selected from $R^a$;

B is selected from:
  (1) aryl,
  (2) —O-aryl,
  (3) —(CH$_2$)$_p$—O-aryl,
  (4) —O—(CH$_2$)$_p$-aryl,
  (5) heteroaryl,
  (6) —O-heteroaryl,
  (7) —(CH$_2$)$_p$—O-heteroaryl,
  (8) —O—(CH$_2$)$_p$-heteroaryl,
  (9) —C$_{3-10}$cycloalkyl,
  (10) —(CH$_2$)$_p$—O—C$_{3-10}$cycloalkyl,
  (11) —O—(CH$_2$)$_p$—C$_{3-10}$cycloalkyl,
  (12) —C$_{2-10}$cycloheteroalkyl,
  (13) —(CH$_2$)$_p$—O—C$_{2-10}$cycloheteroalkyl, and
  (14) —O—(CH$_2$)$_p$—C$_{3-10}$cycloheteroalkyl, wherein each —CH₂, cycloalkyl, cycloheteroalkyl, aryl, and heteroaryl is unsubstituted or substituted with 1, 2 or 3 or 4 substituents selected from $R^b$;

$R^1$ is selected from:
(1) hydrogen, and
(2) halogen;

$R^2$ is selected from:
(1) halogen,
(2) —$C_{1-6}$alkyl,
(3) —$C_{2-6}$alkenyl,
(4) —$C_{2-6}$alkynyl, and
(5) —CN, wherein each alkyl, alkenyl and alkynyl is unsubstituted or substituted with 1-3 substituents selected from: halogen, OH, —NH₂, —NH($C_{1-6}$alkyl), —N($C_{1-6}$alkyl)₂ and —O$C_{1-6}$alkyl;

each $R^a$ is independently selected from:
(1) halogen, and
(2) —$C_{1-6}$alkyl, wherein each alkyl is unsubstituted or substituted with 1-3 substituents selected from: —$C_{1-6}$alkyl and halogen;

each $R^b$ is independently selected from:
(1) halogen,
(2) —CN,
(3) —OH,
(4) —$C_{1-6}$alkyl,
(5) —$C_{2-6}$alkenyl,
(6) —$C_{2-6}$alkynyl,
(7) —O—$C_{1-6}$alkyl,
(8) —O—$C_{2-6}$alkenyl,
(9) —O—$C_{2-6}$alkynyl,
(10) —$C_{3-10}$ cycloalkyl,
(11) —$C_{3-10}$cycloalkenyl,
(12) aryl,
(13) heteroaryl,
(14) —O$C_{3-10}$cycloalkyl,
(15) —O$C_{3-6}$cycloheteroalkyl,
(16) —O-aryl,
(17) —O-heteroaryl,
(18) —NH₂,
(19) —NH$C_{1-6}$alkyl,
(20) —N($C_{1-6}$alkyl)₂,
(21) —S$C_{1-6}$alkyl,
(22) —SO$C_{1-6}$alkyl, and
(23) —SO₂$C_{1-6}$alkyl, wherein each alkyl, alkenyl, alkynyl, cycloalkyl, cycloalkenyl, cycloheteroalkyl, aryl and heteroaryl is unsubstituted or substituted with 1-3 substituents selected from: —$C_{1-6}$alkyl, —O$C_{1-6}$alkyl, —CF₃, —OCF₃, and halogen;

n is 1 or 2;
m is 0, 1, or 2;
p is 1, 2, or 3; and
q is 0 or 1.

2. The compound of claim 1 wherein A is aryl, wherein aryl is unsubstituted or substituted with 1, 2, 3 or 4 substituents selected from $R^a$; or a pharmaceutically acceptable salt thereof.

3. The compound of claim 1 wherein A is heteroaryl, wherein heteroaryl is unsubstituted or substituted with 1, 2, 3 or 4 substituents selected from $R^a$; or a pharmaceutically acceptable salt thereof.

4. The compound of claim 1 wherein B is selected from:
(1) aryl,
(2) —O-aryl,
(3) —(CH₂)$_p$—O-aryl,
(4) —O—(CH₂)$_p$-aryl,
(5) heteroaryl,
(6) —O-heteroaryl,
(7) —O—(CH₂)$_p$-heteroaryl,
(8) —$C_{3-10}$cycloalkyl, and
(9) —O—(CH₂)$_p$—$C_{3-10}$cycloalkyl, wherein B is unsubstituted or substituted with 1, 2 or 3 or 4 substituents selected from $R^b$;
or a pharmaceutically acceptable salt thereof.

5. The compound of claim 1 wherein B is selected from:
(1) aryl,
(2) —O-aryl,
(3) —O—(CH₂)$_p$-aryl, and
(4) heteroaryl,
wherein B is unsubstituted or substituted with 1, 2 or 3 substituents selected from $R^b$; or a pharmaceutically acceptable salt thereof.

6. The compound of claim 1 wherein $R^1$ is halogen; or a pharmaceutically acceptable salt thereof.

7. The compound of claim 1 wherein $R^1$ is hydrogen; or a pharmaceutically acceptable salt thereof.

8. The compound of claim 1 wherein $R^2$ is selected from:
(1) halogen, and
(2) —$C_{1-6}$alkyl, wherein each alkyl is unsubstituted or substituted with 1-3 substituents selected from: halogen, OH, —NH₂, —NH($C_{1-6}$alkyl), —N($C_{1-6}$alkyl)₂ and —O$C_{1-6}$alkyl; or a pharmaceutically acceptable salt thereof.

9. The compound of claim 1 wherein $R^2$ is halogen; or a pharmaceutically acceptable salt thereof.

10. The compound of claim 1 wherein
A is selected from:
(1) aryl, and
(2) heteroaryl,
wherein each aryl and heteroaryl is unsubstituted or substituted with 1, 2, 3 or 4 substituents selected from $R^a$;

B is selected from:
(1) aryl,
(2) —O-aryl,
(3) —(CH₂)$_p$—O-aryl,
(4) —O—(CH₂)$_p$-aryl,
(5) heteroaryl,
(6) —O-heteroaryl,
(7) —O—(CH₂)$_p$-heteroaryl,
(8) —$C_{3-10}$cycloalkyl, and
(9) —O—(CH₂)$_p$—$C_{3-10}$cycloalkyl,
wherein B is unsubstituted or substituted with 1, 2 or 3 or 4 substituents selected from $R^b$;

$R^1$ is selected from:
(1) hydrogen, and
(2) halogen;

$R^2$ is selected from:
(1) halogen, and
(2) —$C_{1-6}$alkyl, wherein each alkyl is unsubstituted or substituted with 1-3 substituents selected from:
halogen, OH, —NH₂, —NH($C_{1-6}$alkyl), —N($C_{1-6}$alkyl)₂ and —O$C_{1-6}$alkyl;

n is 1 or 2;
m is 0, 1, or 2;
p is 1, 2, or 3; and
q is 0 or 1;
or a pharmaceutically acceptable salt thereof.

11. The compound of claim 1 wherein
A is selected from:
 (1) aryl, and
 (2) heteroaryl,
wherein each aryl and heteroaryl is unsubstituted or substituted with 1, 2, 3 or 4 substituents selected from $R^a$;
B is selected from:
 (1) aryl,
 (2) —O-aryl,
 (3) —O—$(CH_2)_p$-aryl, and
 (4) heteroaryl,
wherein B is unsubstituted or substituted with 1, 2 or 3 substituents selected from $R^b$;
$R^1$ is hydrogen;
$R^2$ is halogen;
n is 1;
m is 0, or 1;
p is 1, 2, or 3; and
q is 0 or 1;
or a pharmaceutically acceptable salt thereof.

12. A compound of claim 1 selected from:

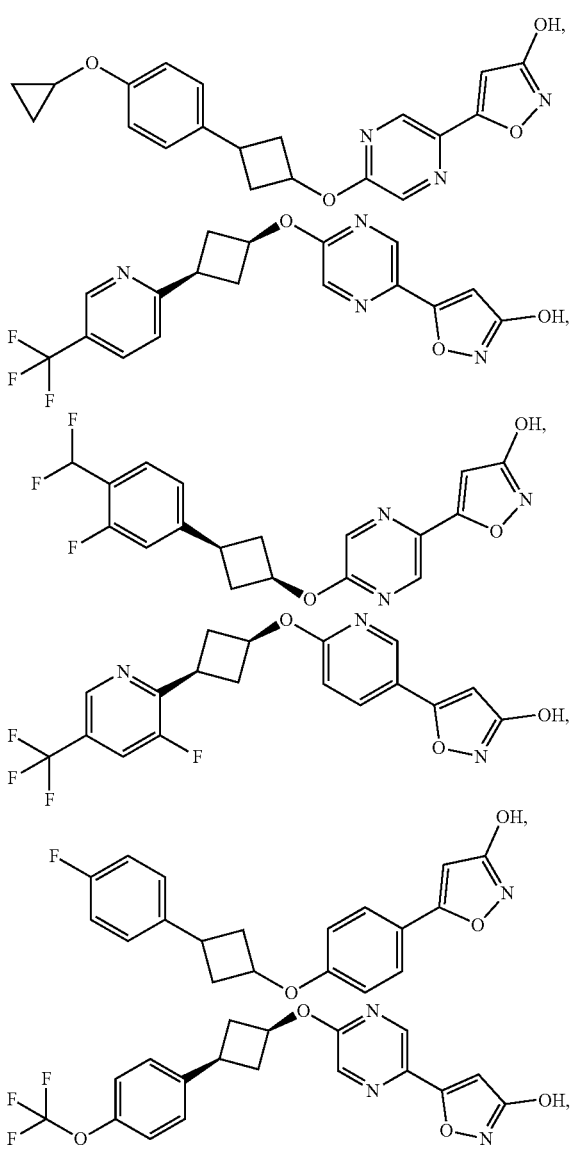

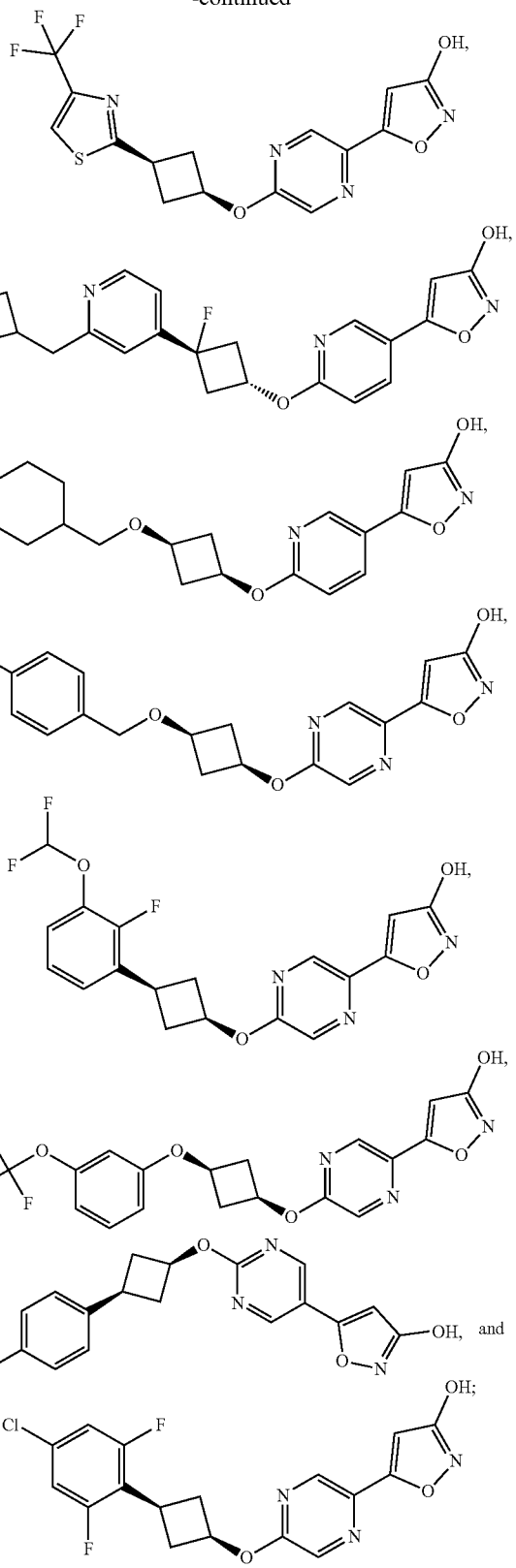

or a pharmaceutically acceptable salt thereof.

13. A pharmaceutical composition comprising a compound of claim 1 in combination with a pharmaceutically acceptable carrier.

14. A method for the treatment of a condition selected from the group consisting of diabetes, hyperlipidemia, obesity, and inflammation related disorders comprising administering to an individual a pharmaceutical composition comprising the compound of claim 1.

* * * * *